(12) United States Patent
Lin et al.

(10) Patent No.: US 12,144,247 B2
(45) Date of Patent: Nov. 12, 2024

(54) ORGANIC COMPOUND AND ELECTRONIC DEVICE AND ELECTRONIC APPARATUS THEREOF

(71) Applicant: SHAANXI LIGHTE OPTOELECTRONICS MATERIAL CO., LTD., Xi'an (CN)

(72) Inventors: Ziwei Lin, Xi'an (CN); Yingwen Li, Xi'an (CN); Xinxuan Li, Xi'an (CN); Youngkook Kim, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 18/003,849

(22) PCT Filed: Mar. 17, 2022

(86) PCT No.: PCT/CN2022/081310
§ 371 (c)(1),
(2) Date: Dec. 29, 2022

(87) PCT Pub. No.: WO2022/199449
PCT Pub. Date: Sep. 29, 2022

(65) Prior Publication Data
US 2023/0189638 A1 Jun. 15, 2023

(30) Foreign Application Priority Data
Mar. 24, 2021 (CN) .......................... 202110315561.0

(51) Int. Cl.
C07D 209/86 (2006.01)
C07D 403/12 (2006.01)
C07D 405/12 (2006.01)
C07D 409/04 (2006.01)
C07D 409/12 (2006.01)
H10K 85/60 (2023.01)
H10K 50/18 (2023.01)

(52) U.S. Cl.
CPC ......... *H10K 85/636* (2023.02); *C07D 209/86* (2013.01); *C07D 403/12* (2013.01); *C07D 405/12* (2013.01); *C07D 409/04* (2013.01); *C07D 409/12* (2013.01); *H10K 85/633* (2023.02); *H10K 50/181* (2023.02); *H10K 85/615* (2023.02); *H10K 85/6572* (2023.02); *H10K 85/6574* (2023.02); *H10K 85/6576* (2023.02)

(58) Field of Classification Search
CPC .. C07D 209/86; C07D 403/12; C07D 405/12; C07D 409/12
See application file for complete search history.

(56) References Cited

U.S. PATENT DOCUMENTS

2020/0119282 A1 4/2020 Sakuma
2020/0259104 A1 8/2020 Sakuma

FOREIGN PATENT DOCUMENTS

| CN | 105503622 A | 4/2016 |
|---|---|---|
| CN | 111039799 A | 4/2020 |
| CN | 111548277 A | 8/2020 |
| CN | 111909043 A | 11/2020 |
| CN | 112110849 A | 12/2020 |
| CN | 112430225 A | 3/2021 |
| CN | 113683603 A | 11/2021 |
| KR | 20150006374 A | 1/2015 |
| WO | WO 2021/025372 | * 2/2021 |
| WO | WO 2022/010305 | * 1/2022 |

OTHER PUBLICATIONS

The World Intellectual Property Organization (WIPO) International Search Report for PCT/CN2022/081310 May 26, 2022 7 Pages (with translation).
China National Intellectual Property Administration (CNIPA) First Office Action and Search Report for CN202110315561.0 Apr. 15, 2022 11 Pages (with translation).

* cited by examiner

*Primary Examiner* — Brian E McDowell
(74) *Attorney, Agent, or Firm* — ANOVA LAW GROUP, PLLC

(57) ABSTRACT

The present application relates to an organic compound, and an electronic device and electronic apparatus thereof. The organic compound of the present application has a structural formula shown in formula 1. When used in an electronic device, the organic compound of the present application can significantly improve the performance of the electronic device.

3 Claims, 1 Drawing Sheet

ORGANIC COMPOUND AND ELECTRONIC DEVICE AND ELECTRONIC APPARATUS THEREOF

CROSS REFERENCE TO RELATED APPLICATION

The present application is a national phase entry under 35 U.S.C § 371 of International Application No. PCT/CN2022/081310, filed on Mar. 17, 2022, which claims priority to Chinese Patent Application 202110315561.0 filed on Mar. 24, 2021, all of which is incorporated into the present application by reference in their entirety.

TECHNICAL FIELD

The present application belongs to the technical field of organic materials, and in particular relates to an organic compound, and an electronic device and electronic apparatus having the same.

BACKGROUND

With the development of electronic technology and the progress of material science, electronic devices for realizing electroluminescence or photoelectric conversion are more and more extensively used. Such an electronic device usually includes: a cathode and an anode that are arranged oppositely, and a functional layer arranged between the cathode and the anode. The functional layer includes a plurality of organic or inorganic film layers, and generally includes an energy conversion layer, a hole transport layer (HTL) arranged between the energy conversion layer and the anode, and an electron transport layer (ETL) arranged between the energy conversion layer and the cathode.

For example, an OLED generally includes an anode, an HTL, an organic light-emitting layer as an energy conversion layer, an ETL, and a cathode that are successively stacked. When a voltage is applied to the cathode and the anode, an electric field is generated at each of the two electrodes; and under the action of the electric field, both electrons at a cathode side and holes at an anode side move towards the organic light-emitting layer and are combined in the organic light-emitting layer to form excitons, and the excitons in an excited state release energy outwards, thereby causing the organic light-emitting layer to emit light.

In the prior art, for example, U.S.20200119282A1 discloses a hole transport material that can be used in an OLED, but an OLED fabricated with the hole transport material exhibits poor performance, life span, or efficiency. Therefore, in order to further improve the performance of electronic devices, it is still necessary to further develop new materials.

SUMMARY

The present application is intended to provide an organic compound, and an electronic device and electronic apparatus thereof. When used in an OLED, the organic compound can prolong a life span of the OLED.

In the first aspect of the present application, an organic compound with a structure shown in formula 1 is provided:

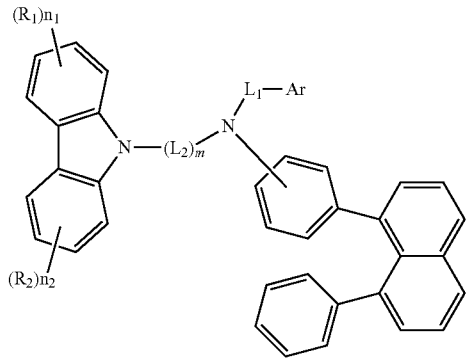

formula 1 wherein Ar is selected from the group consisting of substituted or unsubstituted aryl with 6 to 40 carbon atoms and substituted or unsubstituted heteroaryl with 3 to 40 carbon atoms;

$L_1$ is selected from the group consisting of a single bond, substituted or unsubstituted arylene with 6 to 30 carbon atoms, and substituted or unsubstituted heteroarylene with 3 to 30 carbon atoms;

$L_2$ is selected from the group consisting of substituted or unsubstituted arylene with 6 to 30 carbon atoms and substituted or unsubstituted heteroarylene with 3 to 30 carbon atoms;

m indicates the number of $L_2$, and m is 1 or 2; and when m is 2, any two $L_2$ are the same or different;

$R_1$ and $R_2$ are the same or different, and are each independently selected from the group consisting of deuterium, halogen, cyano, alkyl with 1 to 5 carbon atoms, and aryl with 6 to 12 carbon atoms;

$n_1$ and $n_2$ are collectively represented by $n_t$, and $R_1$ and $R_2$ are collectively represented by $R_t$; t is a variable of 1 or 2; $n_t$, indicates the number of $R_t$; when t is 1 or 2, $n_t$, is selected from the group consisting of 0, 1, 2, 3, and 4; and when $n_t$, is greater than 1, any two $R_t$ are the same or different;

substituents in Ar, $L_1$, and $L_2$ are the same or different, and are each independently selected from the group consisting of deuterium, halogen, cyano, alkyl with 1 to 10 carbon atoms, haloalkyl with 1 to 10 carbon atoms, trialkylsilyl with 3 to 10 carbon atoms, aryl with 6 to 20 carbon atoms, and heteroaryl with 5 to 20 carbon atoms; or, any two adjacent substituents in Ar form a 6-15 membered unsaturated ring.

In the second aspect of the present application, an electronic device is provided, including: an anode and a cathode that are arranged oppositely, and a functional layer arranged between the anode and the cathode, wherein the functional layer includes the organic compound described above.

In the third aspect of the present application, an electronic apparatus is provided, including the electronic device described above.

The organic compound of the present application has a triarylamine structure, which enables the hole transport or electron blocking performance. 1,8-diphenyl-substituted naphthyl can not only improve the hole mobility, but also adjust a three-dimensional configuration of the material, which can improve the film formation performance to improve the stability of the material in a device. In addition, the 9-position-carbazolyl has a high T1 value, and can effectively block the diffusion of excitons in a light-emitting layer, thereby increasing the light-emitting efficiency, external quantum efficiency (EQE), and service life of a device and significantly improving the performance of an OLED.

Other features and advantages of the present application will be described in detail in the following DETAILED DESCRIPTION section.

BRIEF DESCRIPTION OF THE DRAWINGS

The accompanying drawings are provided for further understanding the present application, and constitute a part of the specification. The accompanying drawings and the following specific embodiments are intended to explain the present application, but do not limit the present application.

REFERENCE NUMERALS

Figure 1:
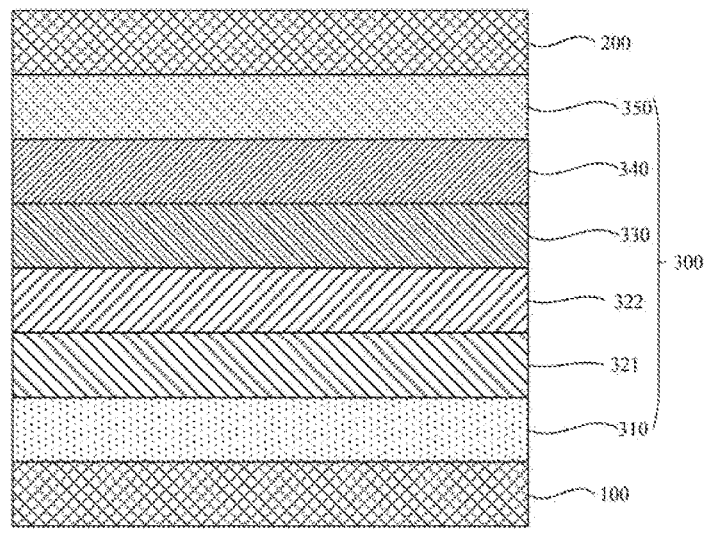
FIG. 1 is a schematic structural diagram of an OLED according to an embodiment of the present application.

100 anode; 200 cathode; 300 functional layer; 310 hole injection layer (HIL); 321 HTL; 322 electron blocking layer (EBL); 330 organic light-emitting layer; 340 ETL; 350 electron injection layer (EIL); and 400 electronic apparatus.

DETAILED DESCRIPTION

Exemplary embodiments will be described below comprehensively with reference to the accompanying drawings. However, the exemplary embodiments can be implemented in various forms and should not be construed as being limited to examples described herein. On the contrary, these embodiments are provided such that the present application is comprehensive and complete, and fully conveys the concept of the exemplary embodiments to those skilled in the art. The described features, structures, or characteristics may be incorporated into one or more embodiments in any suitable manner. In the following description, many specific details are provided to give a full understanding of the embodiments of the present application.

In the first aspect, the present application provides an organic compound with a structure shown in formula 1:

formula 1

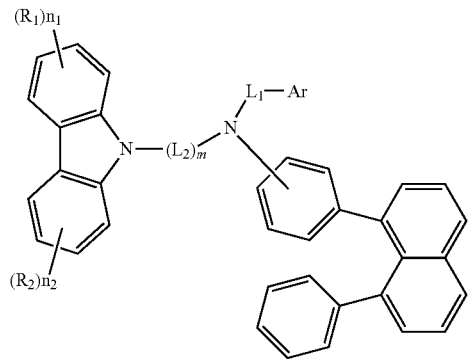

wherein Ar is selected from the group consisting of substituted or unsubstituted aryl with 6 to 40 carbon atoms and substituted or unsubstituted heteroaryl with 3 to 40 carbon atoms;

$L_1$ is selected from the group consisting of a single bond, substituted or unsubstituted arylene with 6 to 30 carbon atoms, and substituted or unsubstituted heteroarylene with 3 to 30 carbon atoms;

$L_2$ is selected from the group consisting of substituted or unsubstituted arylene with 6 to 30 carbon atoms and substituted or unsubstituted heteroarylene with 3 to 30 carbon atoms;

m indicates a number of $L_2$, and m is 1 or 2; and when m is 2, any two $L_2$ are the same or different;

$R_1$ and $R_2$ are the same or different, and are each independently selected from the group consisting of deuterium, halogen, cyano, alkyl with 1 to 5 carbon atoms, and aryl with 6 to 12 carbon atoms;

$n_1$ and $n_2$ are collectively represented by $n_t$, and $R_1$ and $R_2$ are collectively represented by $R_1$; t is a variable of 1 or 2; $n_t$, indicates the number of $R_t$; when t is 1 or 2, $n_t$, is selected from 0, 1, 2, 3, and 4; and when $n_t$ is greater than 1, any two $R_t$ are the same or different;

substituents in Ar, $L_1$, and $L_2$ are the same or different, and are each independently selected from the group consisting of deuterium, halogen, cyano, alkyl with 1 to 10 carbon atoms, haloalkyl with 1 to 10 carbon atoms, trialkylsilyl with 3 to 10 carbon atoms, aryl with 6 to 20 carbon atoms, and heteroaryl with 5 to 20 carbon atoms; or, any two adjacent substituents in Ar form a 6-15 membered unsaturated ring, for example, any two adjacent substituents form a fluorene ring.

In the present application,

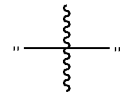

refers to a position attached to other substituents or binding sites.

The description manners used in the present application such as " . . . is (are) each independently", "each of . . . is independently selected from" and " . . . each is (are) independently selected from the group consisting of" can be used interchangeably, and should be understood in a broad sense, which can mean that, in different groups, specific options expressed by the same symbol do not affect each other; or in the same group, specific options expressed by the same symbol do not affect each other. For example,

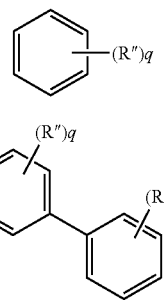

"wherein q is each independently 0, 1, 2, or 3 and substituents R" each are independently selected from the group consisting of hydrogen, deuterium, fluorine, and chlorine" means that, in formula Q-1, there are q substituents R" on the benzene ring, the substituents R″ can be the same or different, and options for each substituent R″ do not affect each other; and in formula Q-2, there are q substituents R″ on each benzene ring of the biphenyl, the numbers q of substituents R″ on the two benzene rings can be the same or different, the substituents R″ can be the same or different, and options for each substituent R″ do not affect each other.

In the present application, the term "substituted or unsubstituted" means that a functional group after the term may have or may not have a substituent (hereinafter, for ease of description, substituents are collectively referred to as Rc). For example, the "substituted or unsubstituted aryl" refers to Rc-substituted aryl or unsubstituted aryl. The substituents Rc may include, for example, deuterium, halogen, cyano, alkyl, haloalkyl, trialkylsilyl, aryl, and heteroaryl; or, any two of the substituents are linked to form a 6-15 membered unsaturated ring together with atoms attached to the two. In the present application, a substituted functional group may have one or more of the above-mentioned substituents Rc, wherein when two substituents Rc are attached to the same atom, these two substituents Rc may exist independently or are linked to form a ring with the atom; and when there are two adjacent substituents Rc on the functional group, the two adjacent substituents Rc may exist independently or may be fused with the functional group to form a ring.

In the present application, the number of carbon atoms in a substituted or unsubstituted functional group refers to the number of all carbon atoms. For example, if $L_2$ is substituted arylene with 12 carbon atoms, the number of all carbon atoms in the arylene and substituents thereon is 12. For example, if Ar is

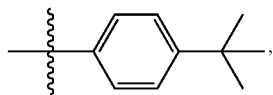 [SMILES: *c1ccc(C(C)(C)C)cc1]

the number of carbon atoms in Ar is 10; and if $L_2$ is

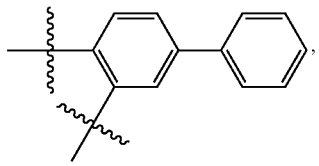 [SMILES: *c1ccc(-c2ccccc2)cc1*]

the number of carbon atoms in $L_2$ is 12.

In the present application, unless otherwise specifically defined, the term "hetero" means that a functional group includes at least one heteroatom such as B, N, O, S, P, Si, or Se, and the rest atoms in the functional group are carbon and hydrogen.

In the present application, the alkyl may include linear alkyl or branched alkyl. The alkyl may have 1 to 5 carbon atoms. In the present application, a numerical range such as "1 to 5" refers to each integer in the range. For example, "alkyl with 1 to 5 carbon atoms" refers to alkyl with 1 carbon atom, 2 carbon atoms, 3 carbon atoms, 4 carbon atoms, or 5 carbon atoms. Specific examples of the alkyl may include, but are not limited to, methyl, ethyl, propyl, isopropyl, n-butyl, isobutyl, sec-butyl, tert-butyl, and pentyl.

In the present application, the aryl refers to any functional group or substituent derived from an aromatic carbocyclic ring. The aryl may refer to a monocyclic aryl group (such as phenyl) or a polycyclic aryl group. In other words, the aryl may refer a monocyclic aryl group, a fused-ring aryl group, two or more monocyclic aryl groups that are conjugated through carbon-carbon bonds, a monocyclic aryl group and a fused-ring aryl group that are conjugated through carbon-carbon bonds, and two or more fused-ring aryl groups that are conjugated through carbon-carbon bonds. That is, unless otherwise specified, two or more aromatic groups that are conjugated through carbon-carbon bonds can also be regarded as the aryl of the present application. For example, the fused-ring aryl group may include a bicyclic fused aryl group (such as naphthyl) and a tricyclic fused aryl group (such as phenanthryl, fluorenyl, and anthracenyl). Examples of the aryl may include, but are not limited to, phenyl, naphthyl, fluorenyl, anthracenyl, phenanthryl, biphenyl, terphenyl, tetraphenyl, pentaphenyl, benzo[9,10]phenanthryl, pyrenyl, benzofluoranthenyl, and chrysenyl. In the present application, the biphenyl can be construed as phenyl-substituted aryl, and can also be construed as unsubstituted aryl.

The arylene involved in the present application refers to a divalent group obtained after one hydrogen atom is further removed from aryl.

In the present application, the substituted aryl may refer to aryl in which one or more hydrogen atoms are substituted by a group such as deuterium, halogen, cyano, alkyl, trifluoromethyl, trimethylsilyl, aryl, or heteroaryl. It should be understood that the number of carbon atoms in the substituted aryl refers to the total number of carbon atoms in the aryl and substituents thereon. For example, in substituted aryl with 18 carbon atoms, there are a total of 18 carbon atoms in the aryl and substituents thereon.

In the present application, the heteroaryl refers to a monovalent aromatic ring with 1, 2, 3, 4, 5, 6, or 7 heteroatoms or a derivative thereof. The heteroatoms may be one or more selected from the group consisting of B, O, N, P, Si, Se, and S. The heteroaryl can be monocyclic heteroaryl or polycyclic heteroaryl. In other words, the heteroaryl may refer to a single aromatic ring system or multiple aromatic ring systems conjugated through carbon-carbon bonds, wherein each aromatic ring system is an aromatic monocyclic ring or an aromatic fused ring. For example, the heteroaryl may include, but is not limited to, thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, silylfluorenyl, dibenzofuranyl, N-phenylcarbazolyl, N-pyridylcarbazolyl, and N-methylcarbazolyl. The thienyl, furyl, phenanthrolinyl, and the like are heteroaryl with a single aromatic ring system; and the N-arylcarbazolyl, N-heteroarylcarbazolyl, and the like are heteroaryl with multiple ring systems conjugated through carbon-carbon bonds.

The heteroarylene involved in the present application refers to a divalent group obtained after one hydrogen atom is further removed from heteroaryl.

In the present application, substituted heteroaryl refers to heteroaryl in which one or more hydrogen atoms are substituted by a group such as deuterium, halogen, cyano, alkyl, aryl, heteroaryl, trimethylsilyl, trifluoromethyl, or alkyl. It should be understood that the number of carbon atoms in the substituted heteroaryl refers to the total number of carbon atoms in the heteroaryl and substituents thereon.

In the present application, specific examples of aryl as a substituent may include, but are not limited to, phenyl, biphenyl, naphthyl, anthracenyl, phenanthryl, and chrysenyl.

In the present application, specific examples of heteroaryl as a substituent may include, but are not limited to, pyridyl, carbazolyl, dibenzofuranyl, dibenzothienyl, quinolinyl, quinazolinyl, quinoxalinyl, and isoquinolinyl.

In the present application, the halogen may include fluorine, iodine, bromine, chlorine, or the like.

In the present application, specific examples of trialkylsilyl may include, but are not limited to, trimethylsilyl and triethylsilyl.

In the present application, specific examples of haloalkyl may include, but are not limited to, trifluoromethyl.

In the present application, a non-positional bond refers to a single bond " -$\overset{\xi}{\underset{\xi}{-}}$- " extending from a ring system, which means that one end of the bond can be attached to any position in the ring system through which the bond penetrates, and the other end is attached to the remaining part in the compound molecule.

For example, as shown in the following formula (f), the naphthyl represented by the formula (f) is attached to the remaining part in the molecule through two non-positional bonds that penetrate through the bicyclic ring, which indicates any possible attachment modes shown in formula (f-1) to formula (f-10).

(f)

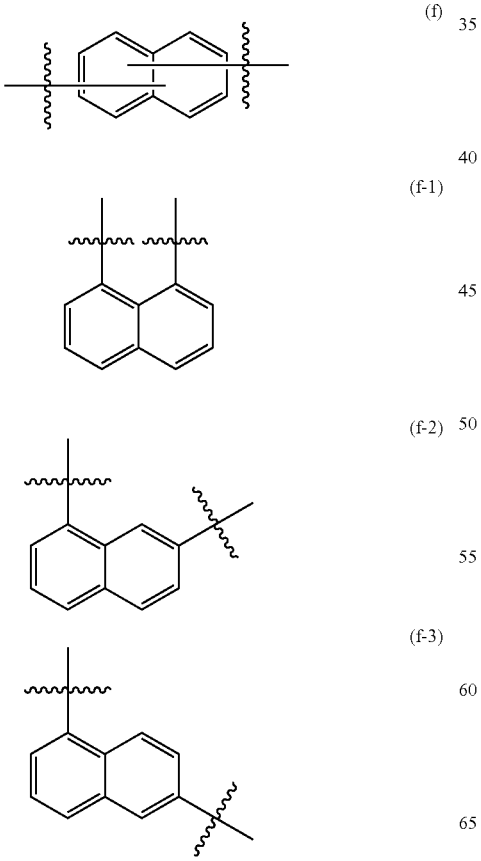

(f-1)

(f-2)

(f-3)

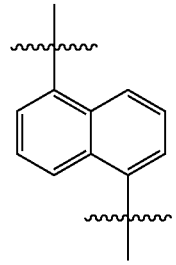

(f-4)

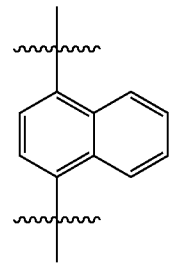

(f-5)

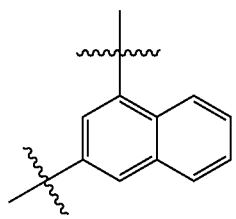

(f-6)

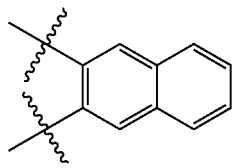

(f-7)

(f-8)

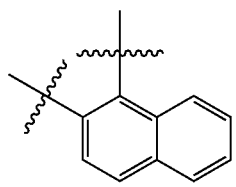

(f-9)

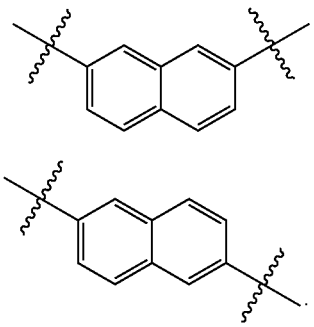

(f-10)

For example, as shown in the following formula (X'), the dibenzofuranyl represented by the formula (X') is attached to the remaining part of the molecule through a non-positional bond extending from the middle of a benzene ring at a side, which indicates any possible attachment modes shown in formula (X'-1) to formula (X'-4).

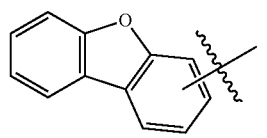
(X')

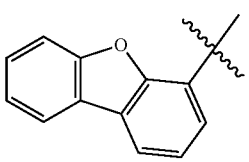
(X'-1)

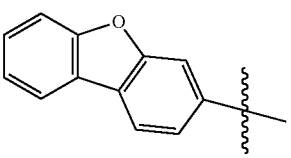
(X'-2)

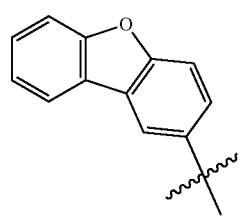
(X'-3)

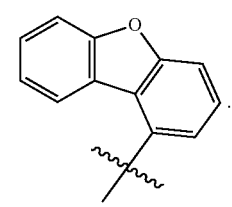
(X'-4)

In an embodiment of the present application, $R_1$ and $R_2$ are each independently selected from the group consisting of deuterium, fluorine, cyano, methyl, ethyl, isopropyl, tert-butyl, phenyl, naphthyl, and biphenyl.

In an embodiment of the present application, Ar is selected from the group consisting of substituted or unsubstituted aryl with 6 to 25 carbon atoms and substituted or unsubstituted heteroaryl with 3 to 24 carbon atoms. For example, Ar is selected from the group consisting of substituted or unsubstituted aryl with 6, 7, 8, 9, 10, 11, 12, 13, 14, 15, 16, 17, 18, 19, 20, 21, 22, 23, 24, or 25 carbon atoms and substituted or unsubstituted heteroaryl with 3, 4, 5, 6, 7, 8, 9, 10, 11, 12, 13, 14, 15, 16, 17, 18, 19, 20, 21, 22, 23, or 24 carbon atoms.

Optionally, Ar is selected from the group consisting of substituted or unsubstituted aryl with 6 to 25 carbon atoms and substituted or unsubstituted heteroaryl with 12 to 18 carbon atoms;

when Ar has one or more substituents, the one or more substituents may be the same or different, and are each independently selected from the group consisting of deuterium, halogen, cyano, alkyl with 1 to 5 carbon atoms, haloalkyl with 1 to 5 carbon atoms, trialkylsilyl with 3 to 6 carbon atoms, aryl with 6 to 12 carbon atoms, and heteroaryl with 5 to 12 carbon atoms; or, any two adjacent substituents in Ar may form a fluorene ring.

Optionally, Ar is selected from the group consisting of substituted or unsubstituted phenyl, substituted or unsubstituted biphenyl, substituted or unsubstituted terphenyl, substituted or unsubstituted naphthyl, substituted or unsubstituted phenanthryl, substituted or unsubstituted anthracenyl, substituted or unsubstituted dibenzofuranyl, substituted or unsubstituted dibenzothienyl, substituted or unsubstituted carbazolyl, substituted or unsubstituted fluorenyl, and spirobifluorenyl.

Preferably, when Ar has one or more substituents, the one or more substituents may be the same or different, and are each independently selected from the group consisting of deuterium, fluorine, chlorine, cyano, trifluoromethyl, trimethylsilyl, methyl, ethyl, isopropyl, tert-butyl, phenyl, biphenyl, naphthyl, pyridyl, and carbazolyl.

Optionally, Ar is a substituted or unsubstituted group W; an unsubstituted group W is selected from the group consisting of the following groups:

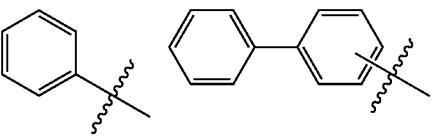

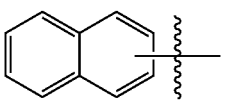

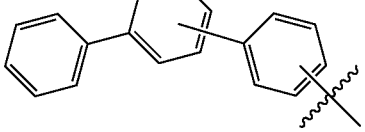

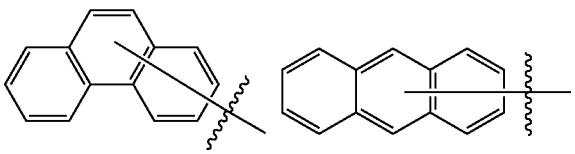

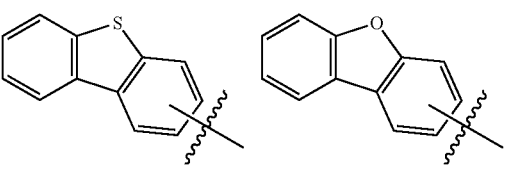

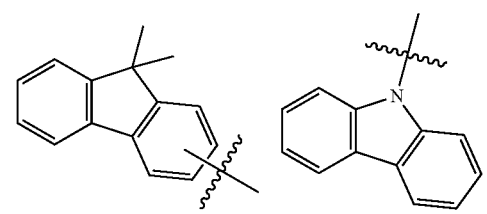

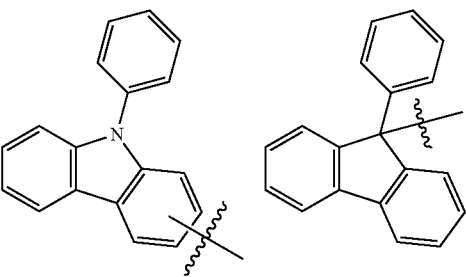

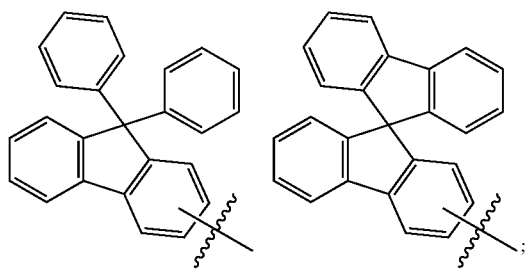

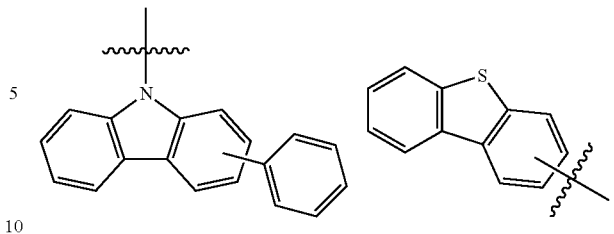

a substituted group W may have one or more substituents, and the one or more substituents are each independently selected from the group consisting of deuterium, fluorine, chlorine, cyano, trifluoromethyl, trimethylsilyl, methyl, ethyl, isopropyl, tert-butyl, phenyl, biphenyl, naphthyl, pyridyl, and carbazolyl; and when the substituted group W has two or more substituents, the two or more substituents are the same or different.

Optionally, Ar is selected from the group consisting of the following groups:

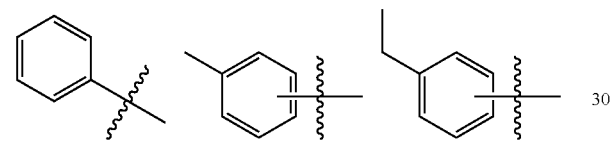

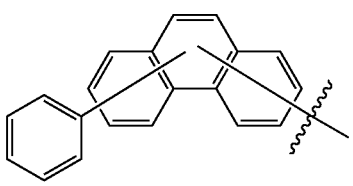

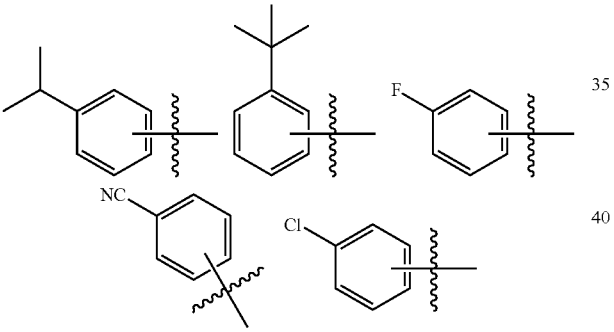

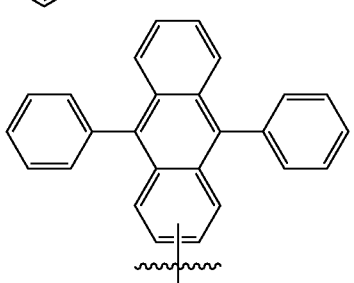

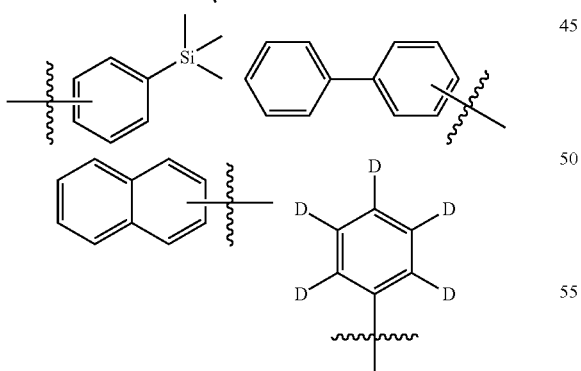

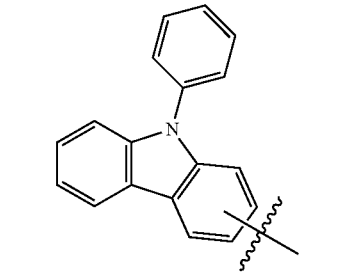

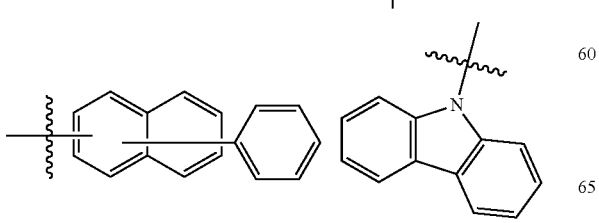

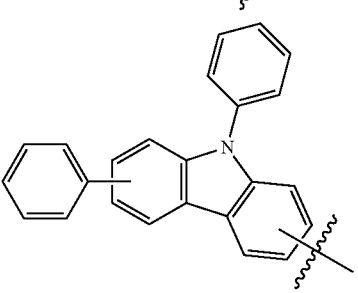

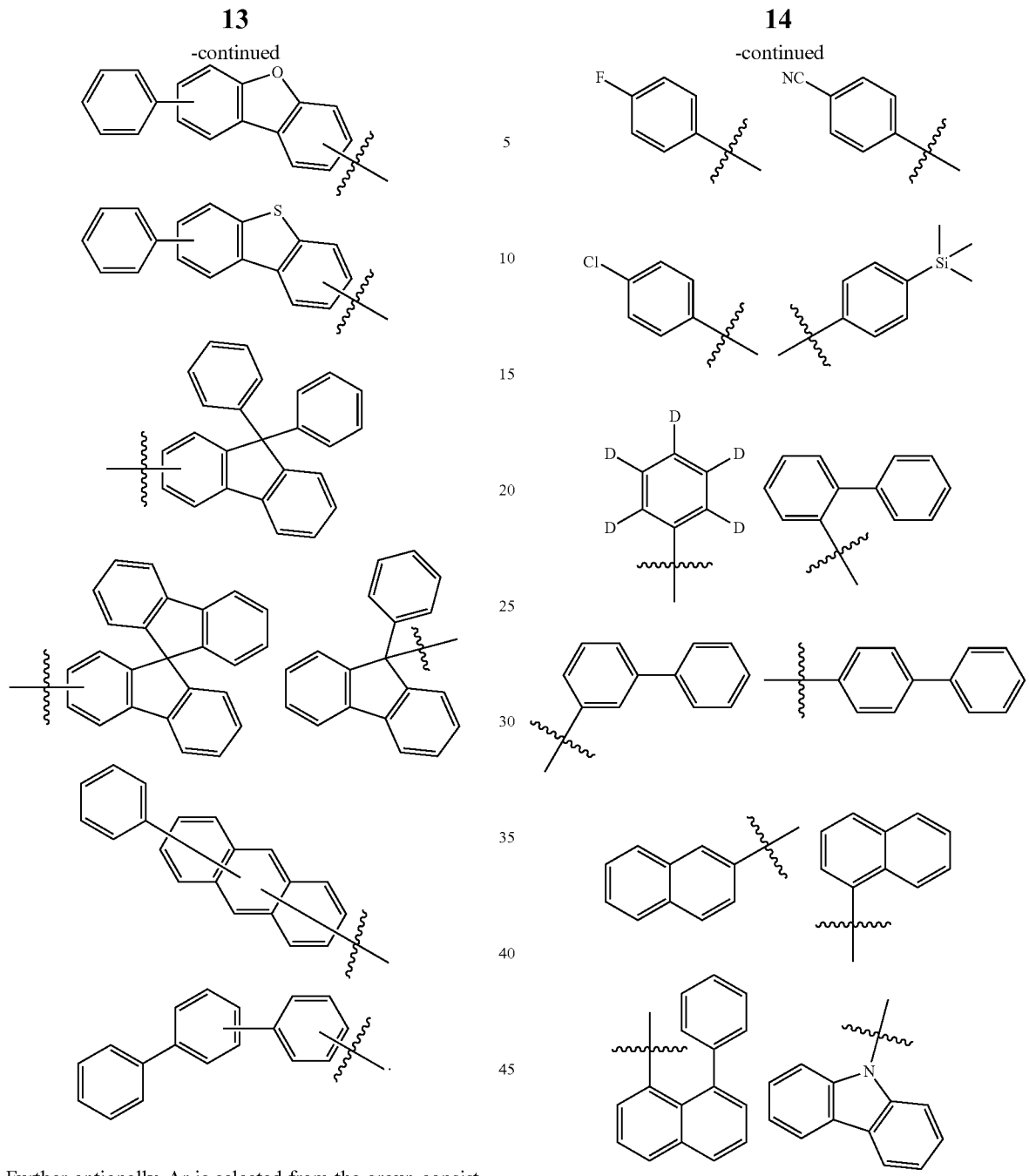
Further optionally, Ar is selected from the group consisting of the following groups:
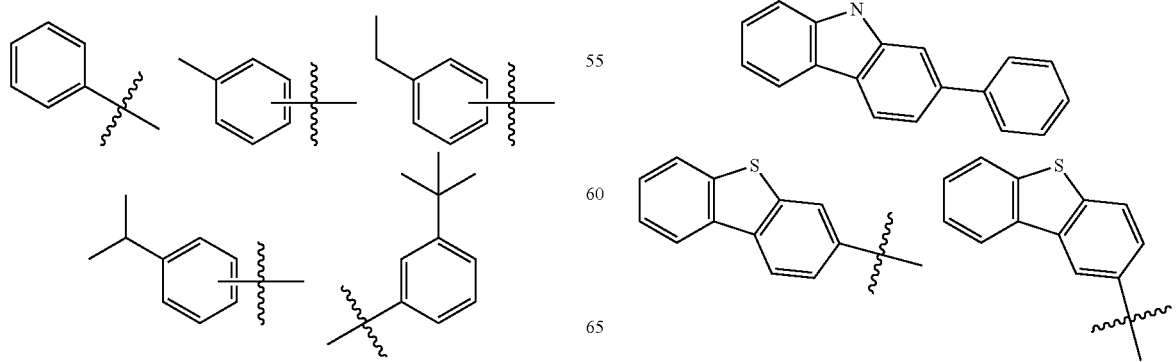

-continued
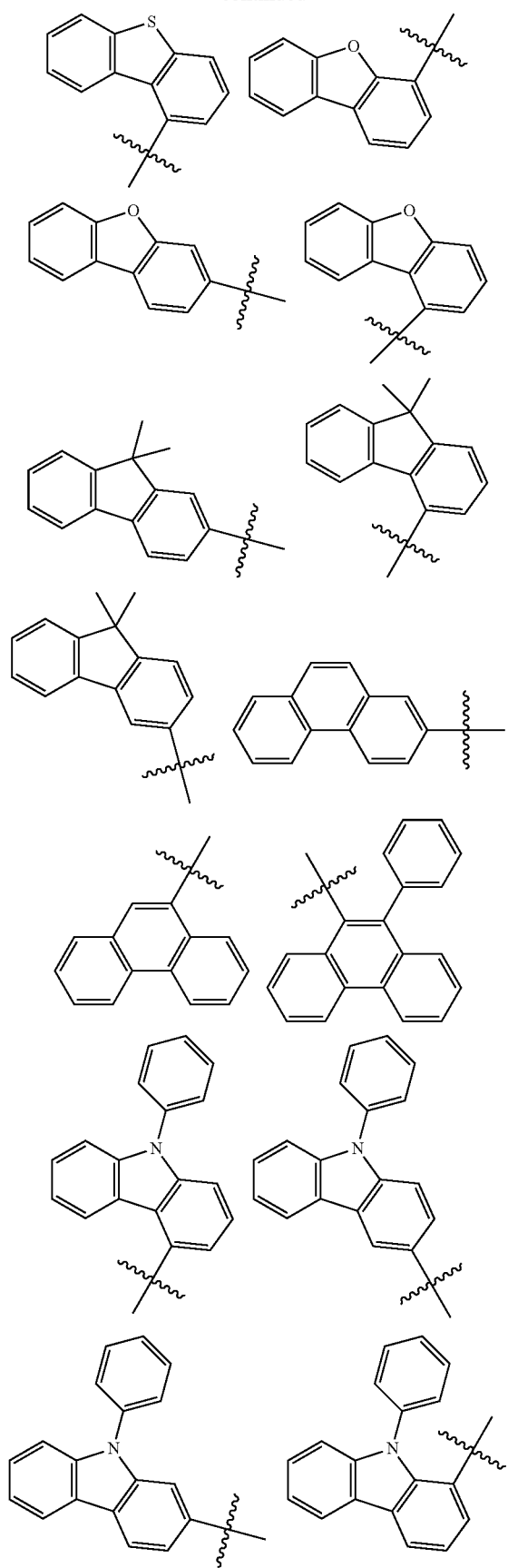
-continued
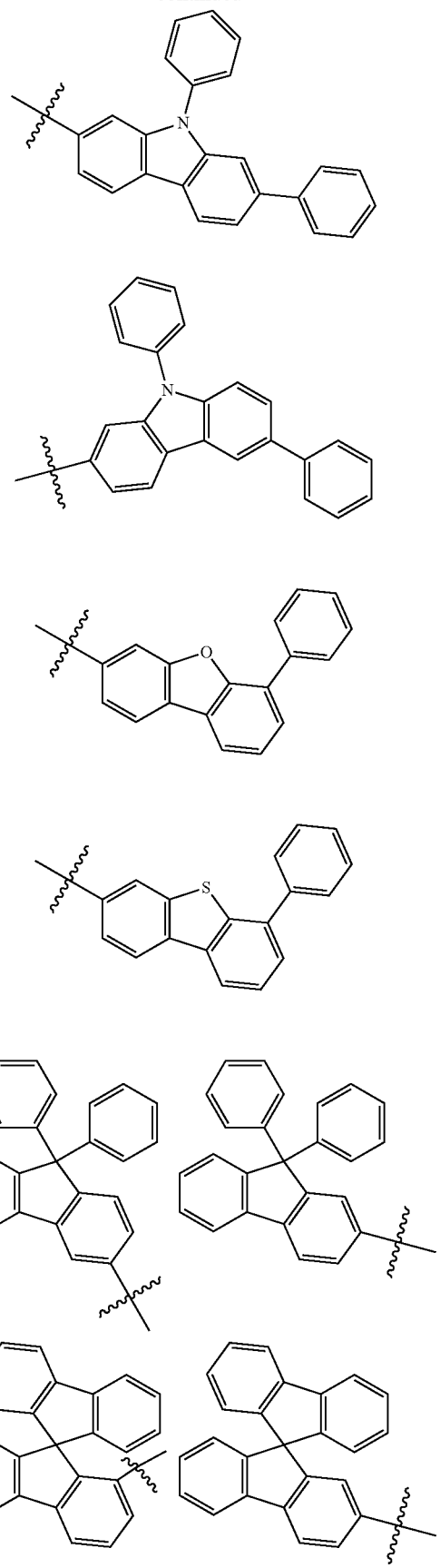

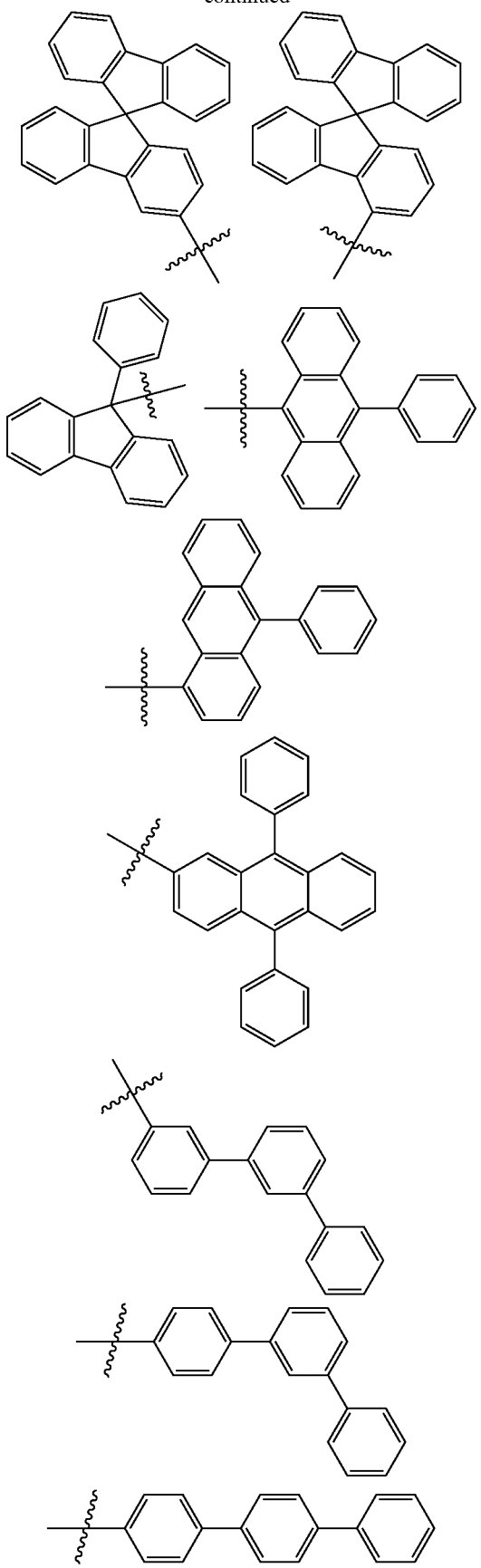

In an embodiment of the present application, $L_1$ is selected from the group consisting of a single bond, substituted or unsubstituted arylene with 6 to 20 carbon atoms, and substituted or unsubstituted heteroarylene with 3 to 12 carbon atoms; and $L_2$ is selected from the group consisting of substituted or unsubstituted arylene with 6 to 20 carbon atoms and substituted or unsubstituted heteroarylene with 3 to 12 carbon atoms. For example, $L_1$ is selected from the group consisting of a single bond, substituted or unsubstituted arylene with 6, 7, 8, 9, 10, 11, 12, 13, 14, 15, 16, 17, 18, 19, or 20 carbon atoms and substituted or unsubstituted heteroarylene with 3, 4, 5, 6, 7, 8, 9, 10, 11, or 12 carbon atoms; and $L_2$ is selected from the group consisting of substituted or unsubstituted arylene with 6, 7, 8, 9, 10, 11, 12, 13, 14, 15, 16, 17, 18, 19, or 20 carbon atoms and substituted or unsubstituted heteroarylene with 3, 4, 5, 6, 7, 8, 9, 10, 11, or 12 carbon atoms.

Preferably, substituents in $L_1$ and $L_2$ are each independently selected from the group consisting of deuterium, halogen, cyano, alkyl with 1 to 5 carbon atoms, and aryl with 6 to 12 carbon atoms.

Optionally, $L_1$ is selected from the group consisting of a single bond, substituted or unsubstituted phenylene, substituted or unsubstituted naphthylene, substituted or unsubstituted phenanthrylene, substituted or unsubstituted biphenylene, substituted or unsubstituted terphenylene, substituted or unsubstituted fluorenylene, substituted or unsubstituted dibenzofuranylene, and substituted or unsubstituted dibenzothienylene; and $L_2$ is selected from the group consisting of substituted or unsubstituted phenylene, substituted or unsubstituted naphthylene, substituted or unsubstituted phenanthrylene, substituted or unsubstituted biphenylene, substituted or unsubstituted terphenylene, substituted or unsubstituted fluorenylene, substituted or unsubstituted dibenzofuranylene, and substituted or unsubstituted dibenzothienylene.

Preferably, substituents in $L_1$ and $L_2$ are each independently selected from the group consisting of deuterium, fluorine, chlorine, cyano, methyl, ethyl, isopropyl, tert-butyl, phenyl, naphthyl, and biphenyl.

Optionally, $L_1$ is selected from the group consisting of a single bond and a substituted or unsubstituted group V; $L_2$ is a substituted or unsubstituted group V; an unsubstituted group V is selected from the group consisting of the following groups:

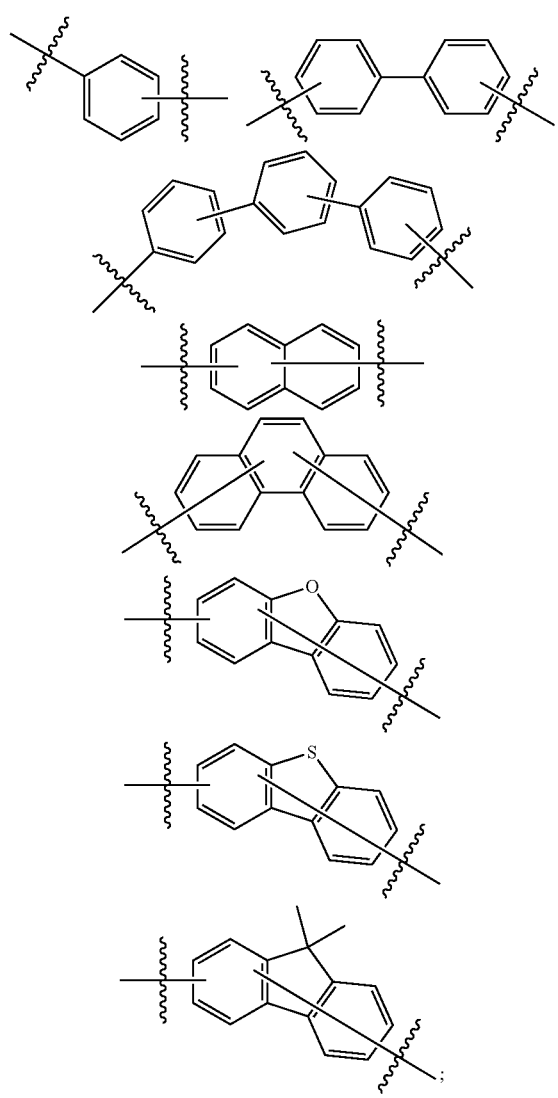

wherein a substituted group V may have one or more substituents, and the one or more substituents are each independently selected from the group consisting of deuterium, fluorine, chlorine, cyano, methyl, ethyl, isopropyl, ter-butyl, phenyl, naphthyl, and biphenyl; and when the substituted group V has two or more substituents, the two or more substituents are the same or different.

Further optionally, L₁ is selected from the group consisting of a single bond and the following groups:

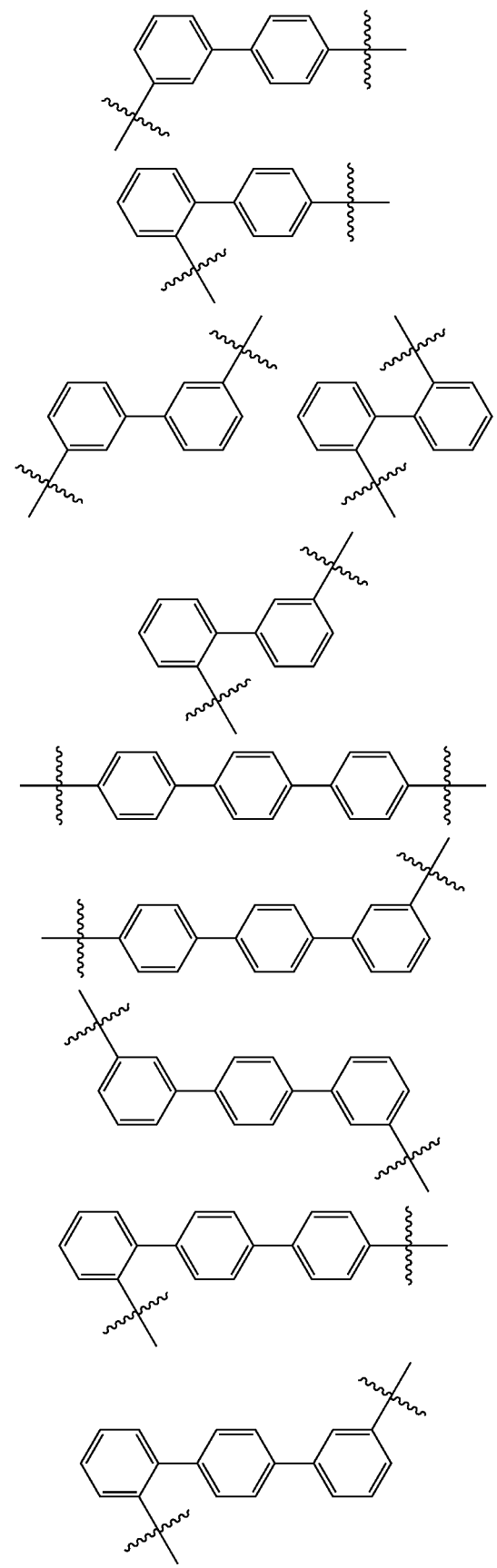

-continued
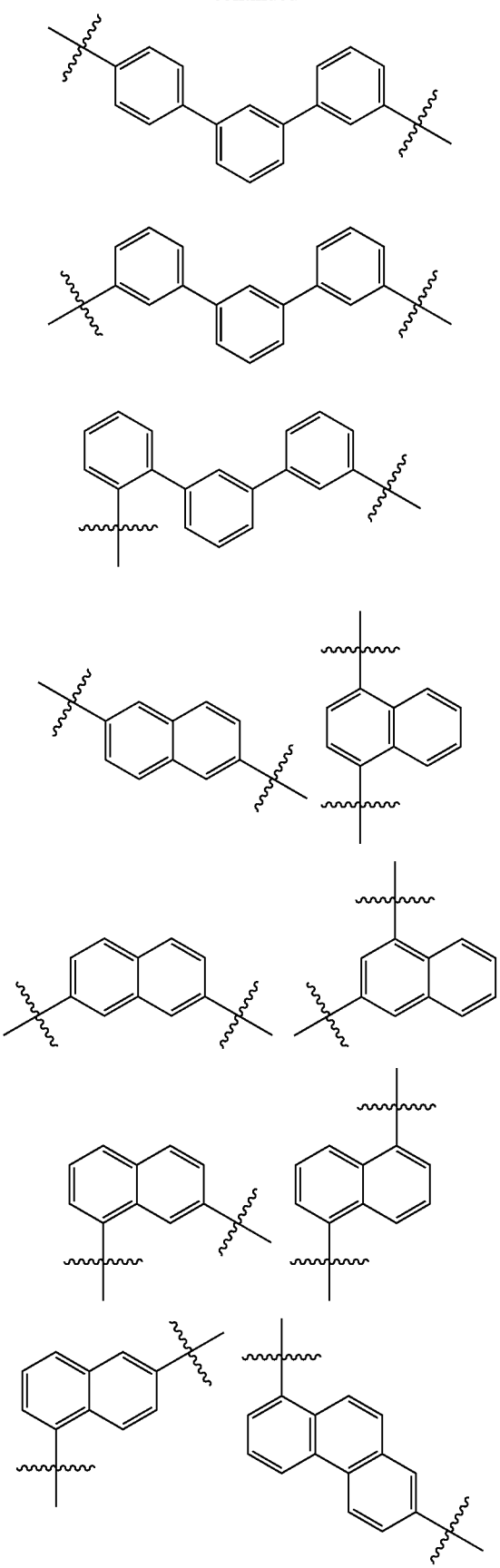
-continued
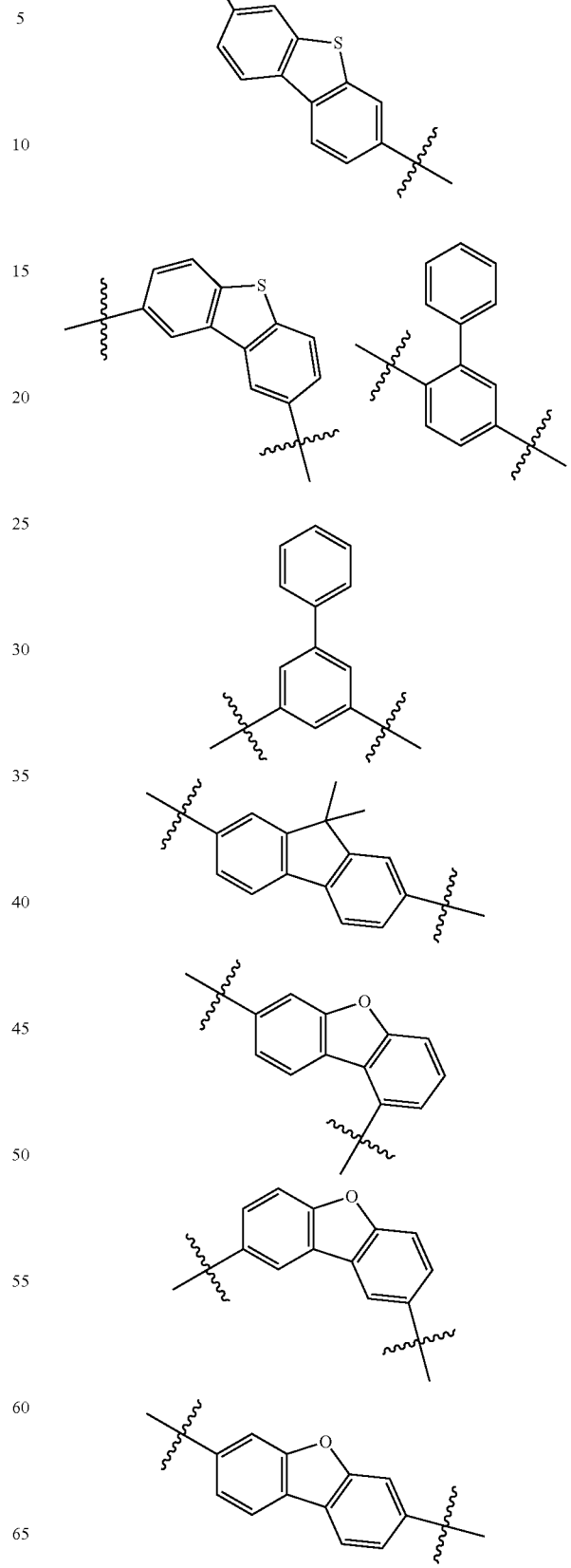

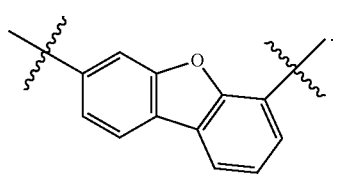
Further optionally, L₂ is selected from the group consisting of the following groups:
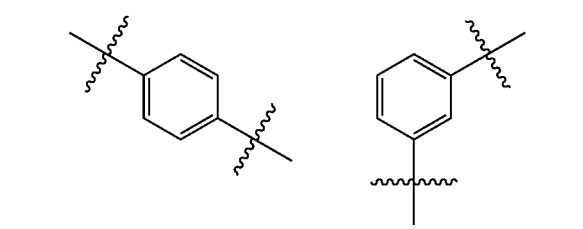
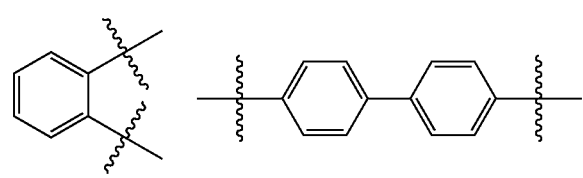
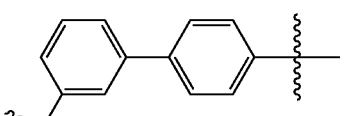
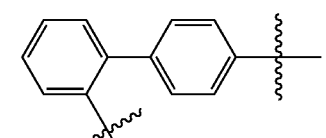
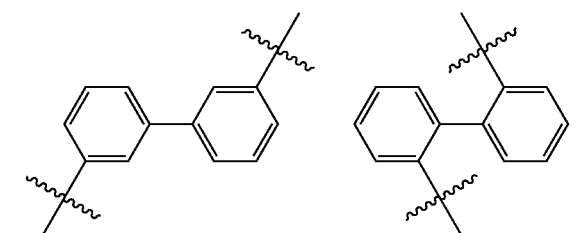
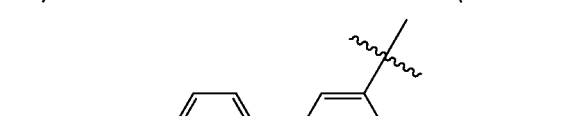
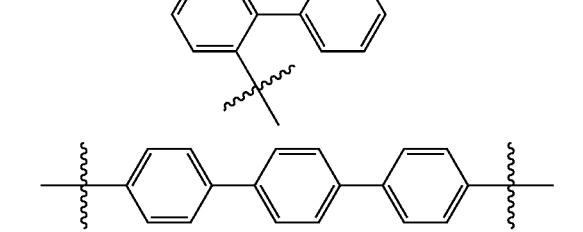
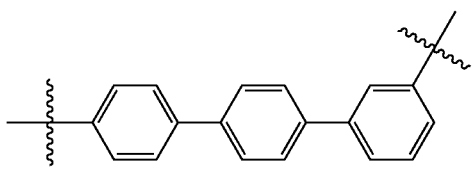
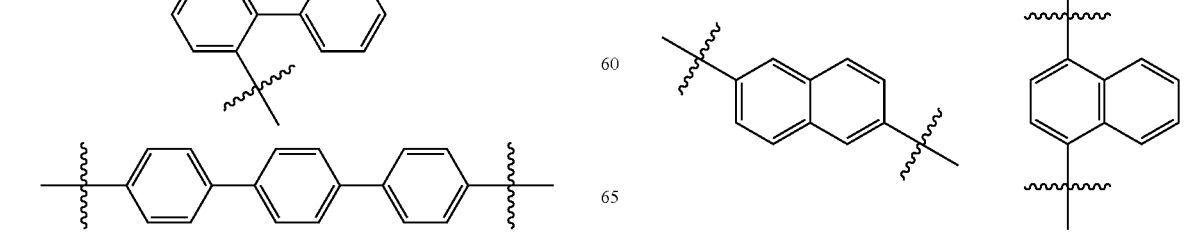
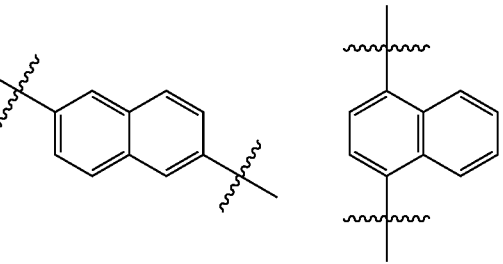

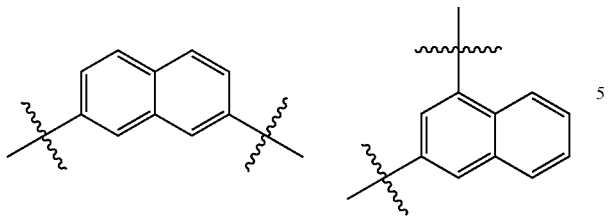
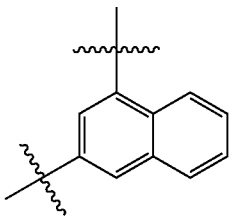
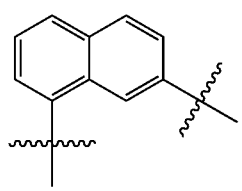
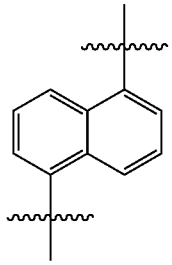
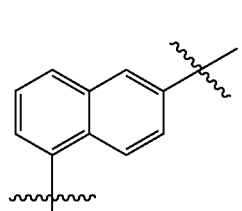
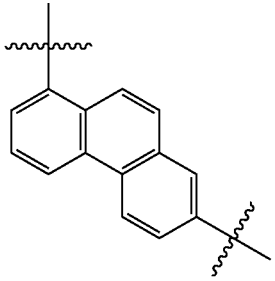
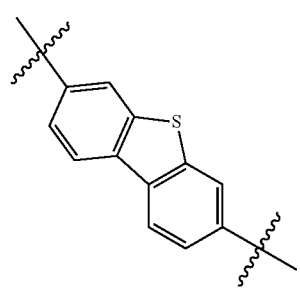
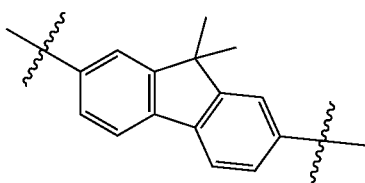
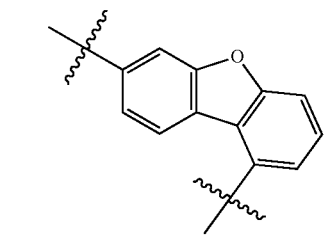
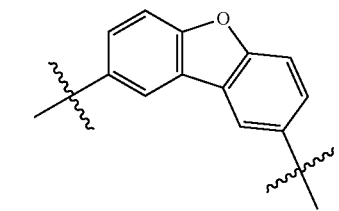
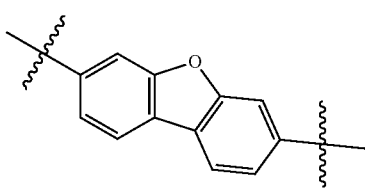
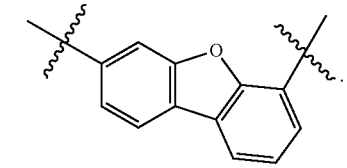
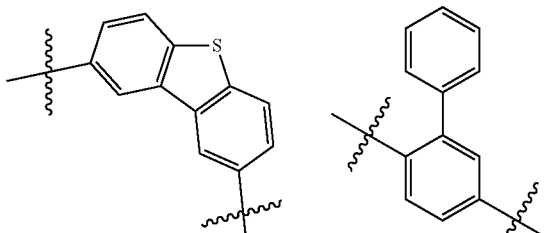
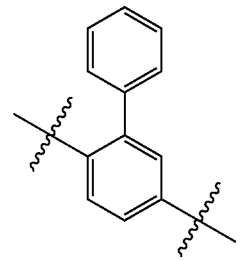
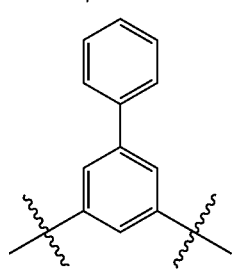
Optionally, the organic compound is selected from the group consisting of the following compounds:
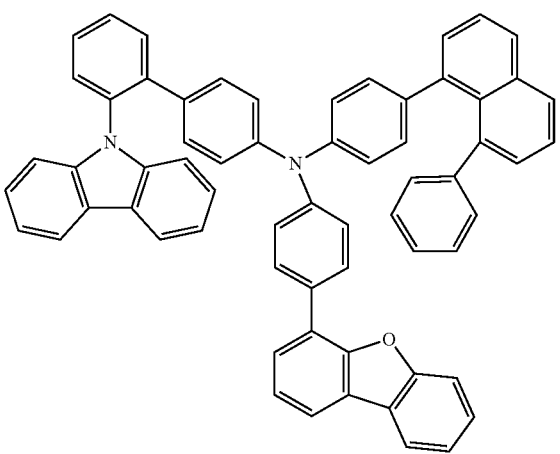
1

2
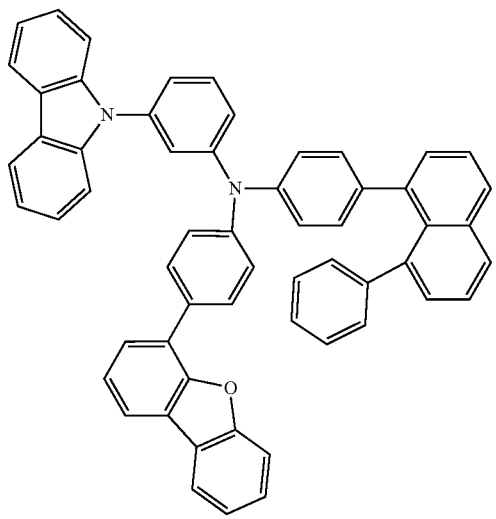
3
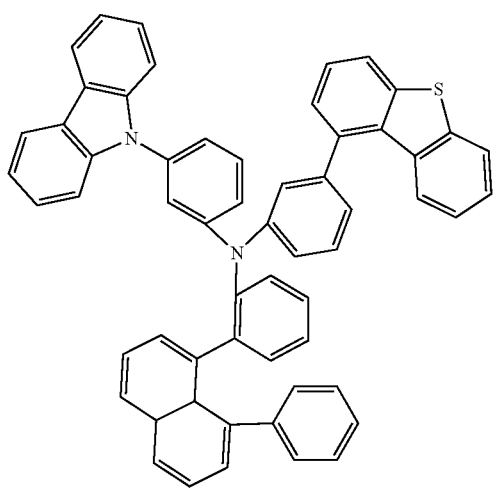
4
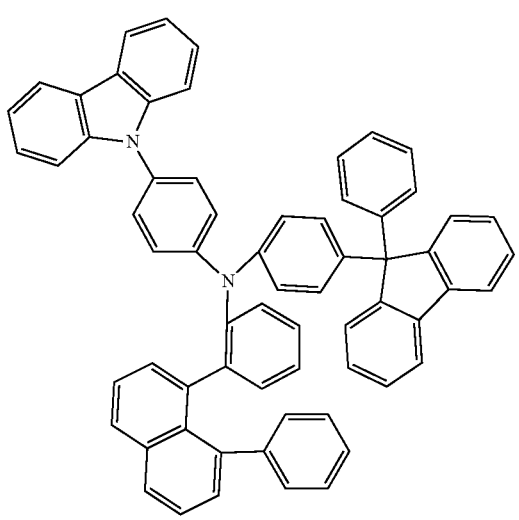
5
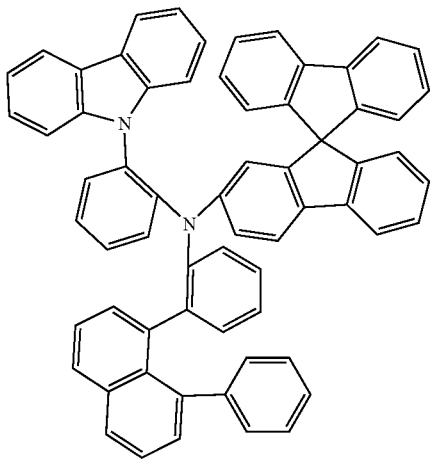
6
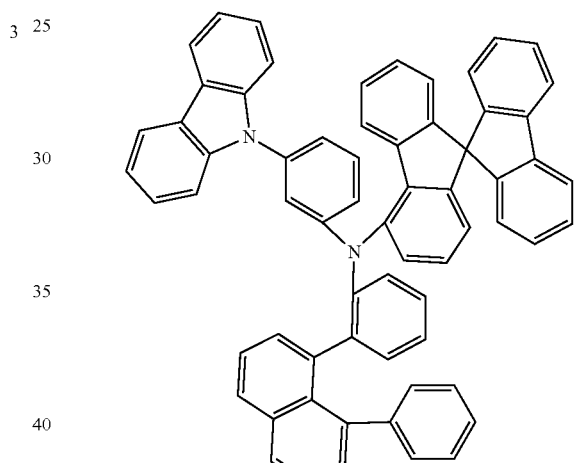
7
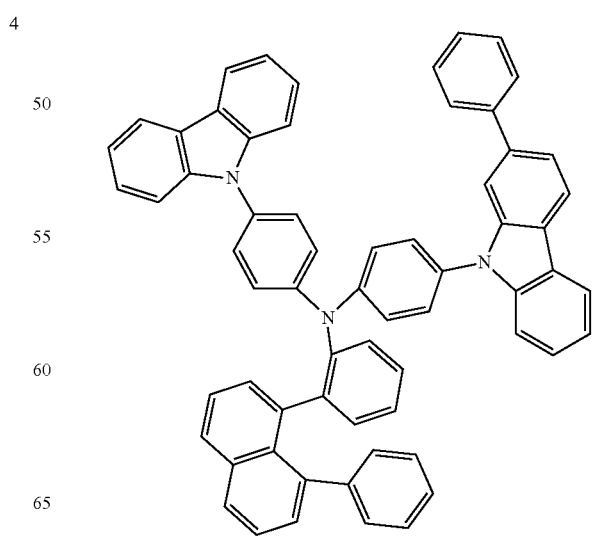

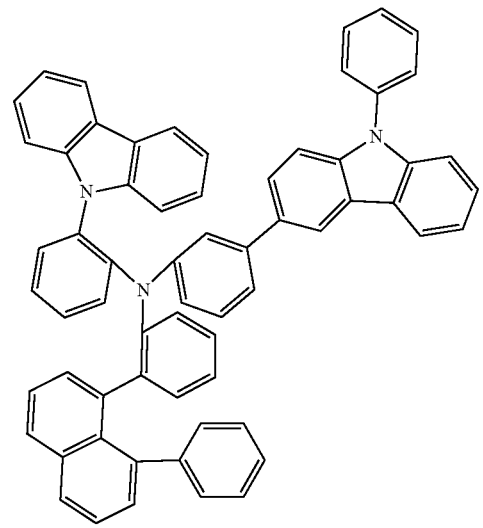
8
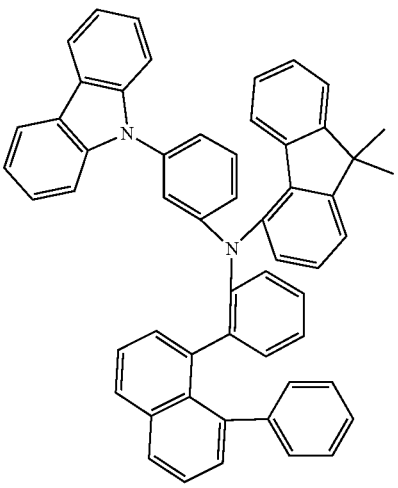
11
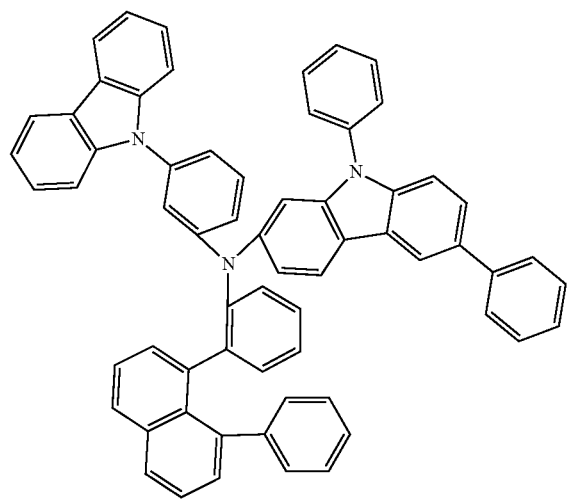
9
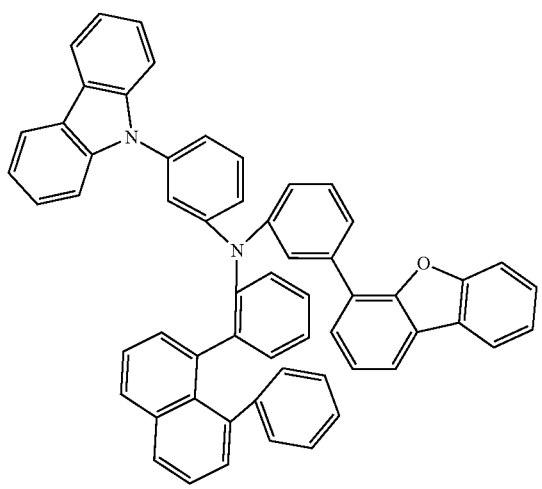
12
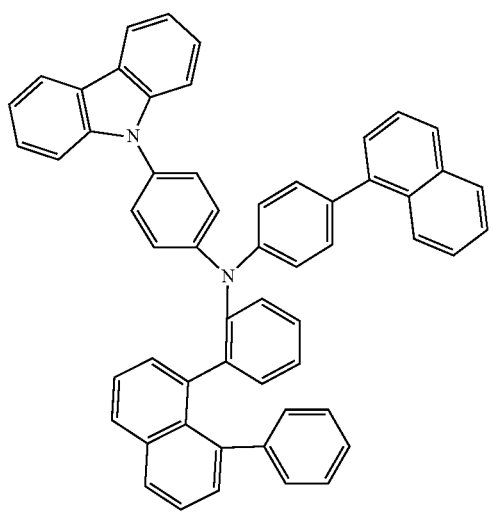
10
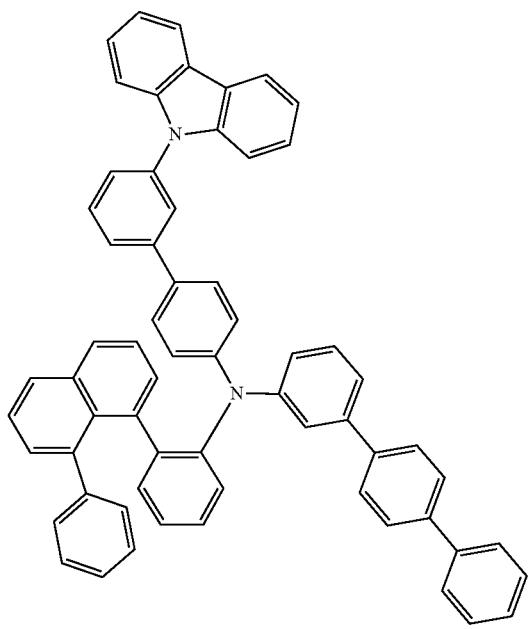
13

14
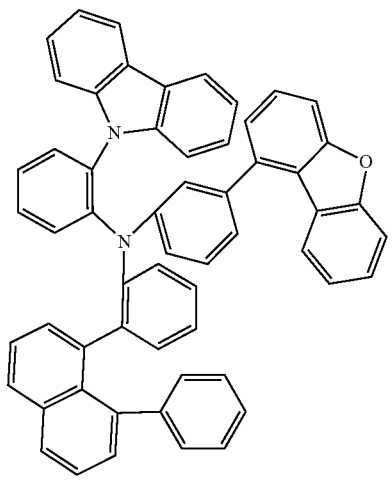
15
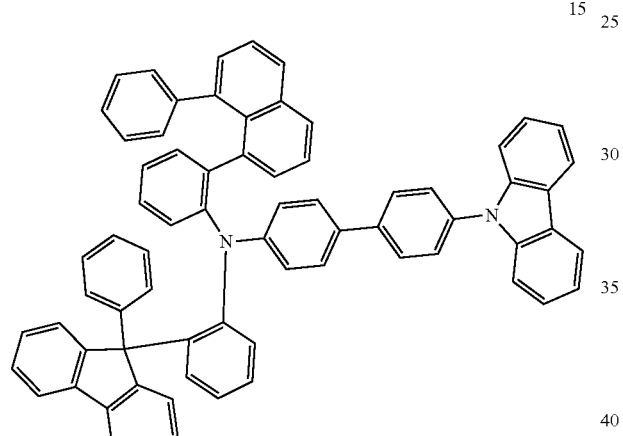
16
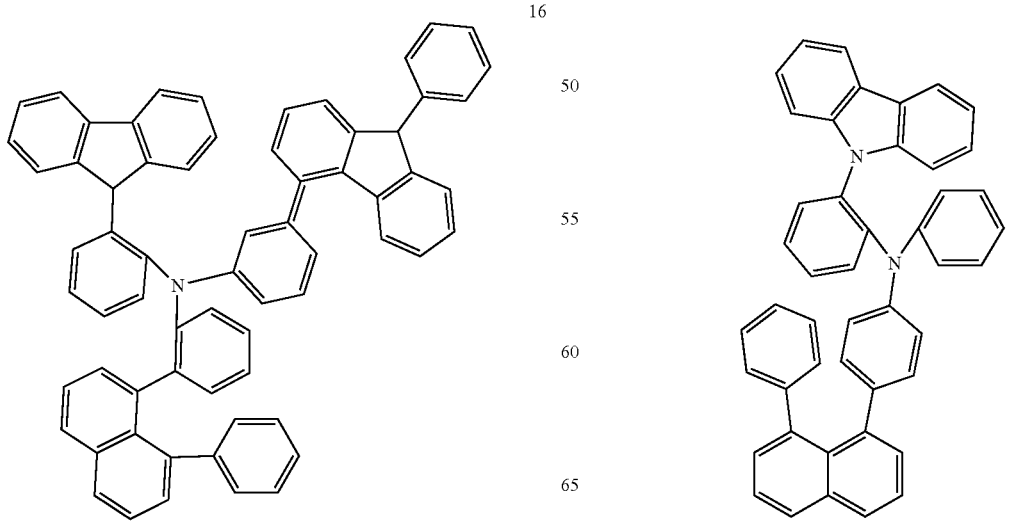
17
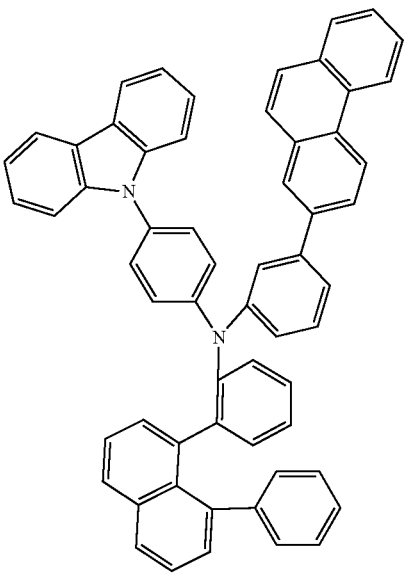
18
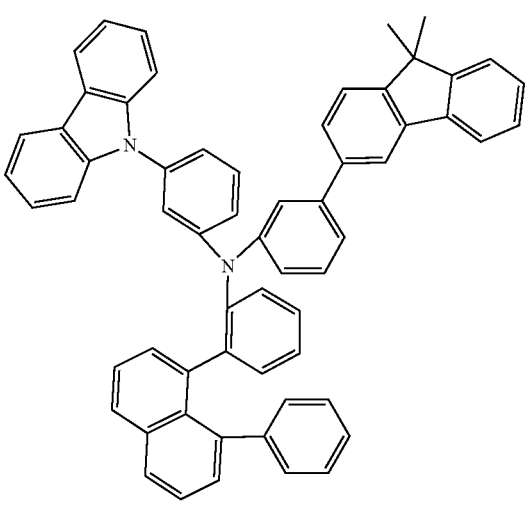
19

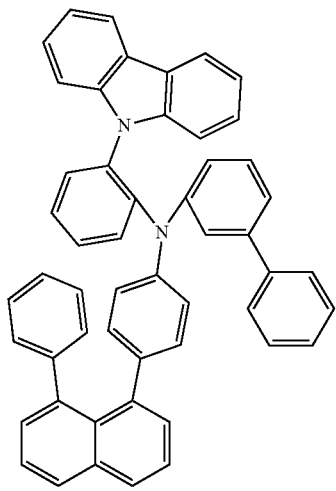
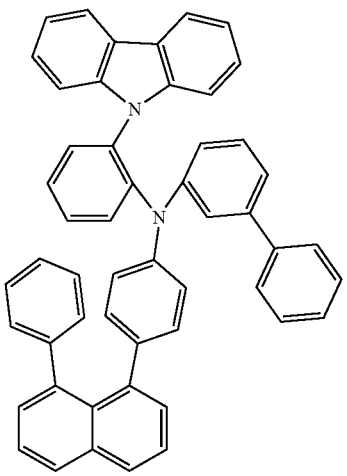
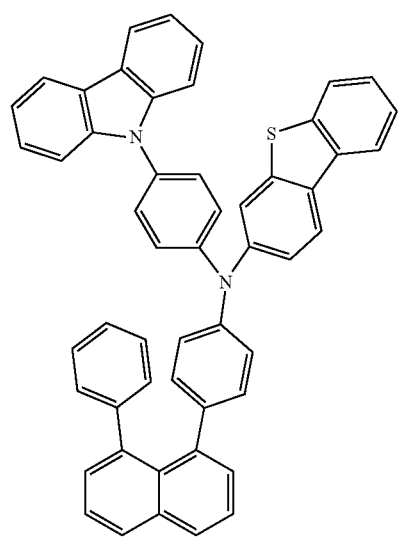
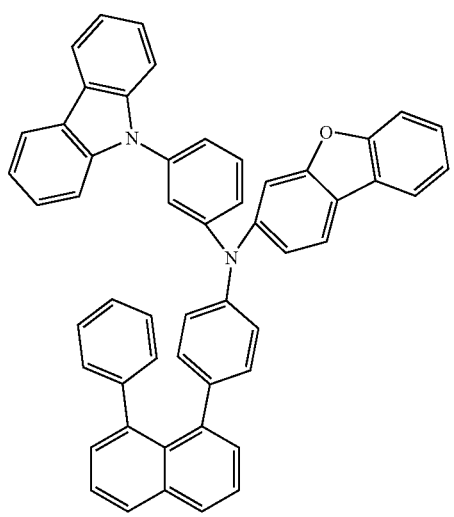
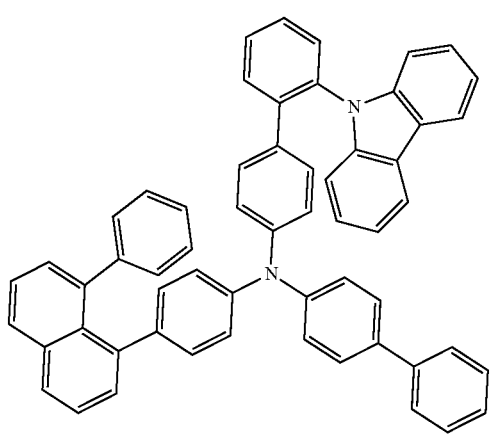
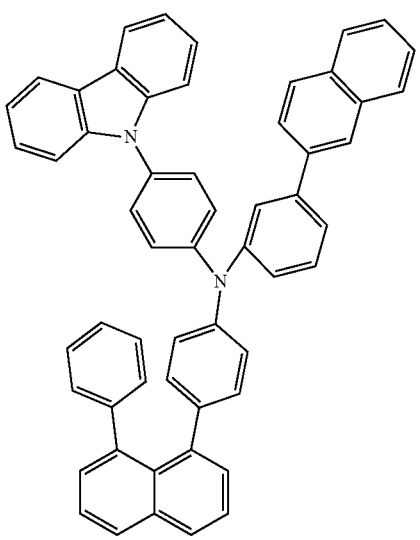

26
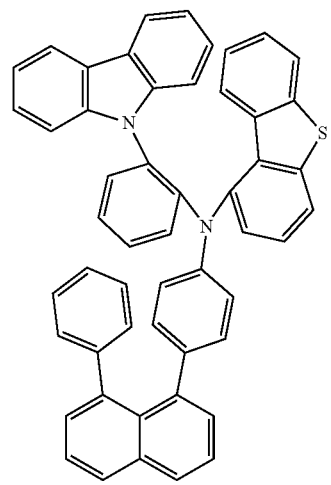
27
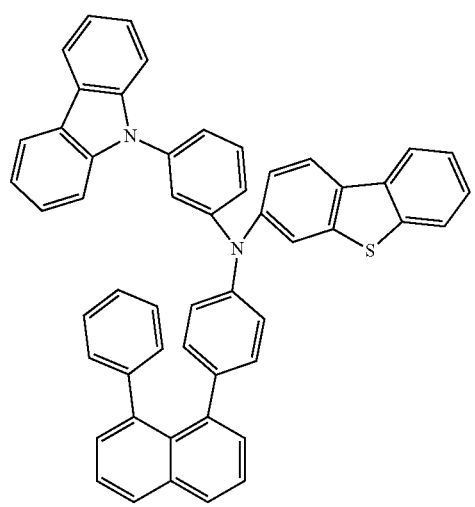
29
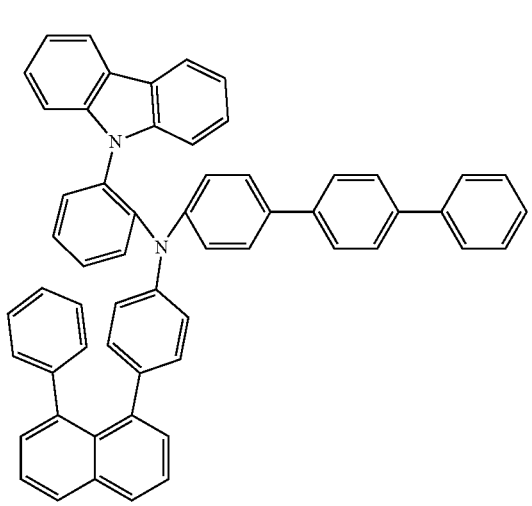
30
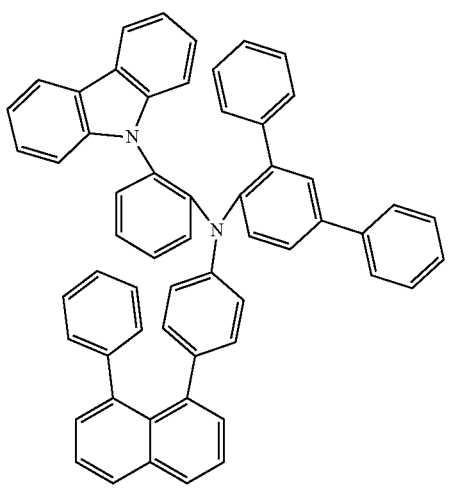
31
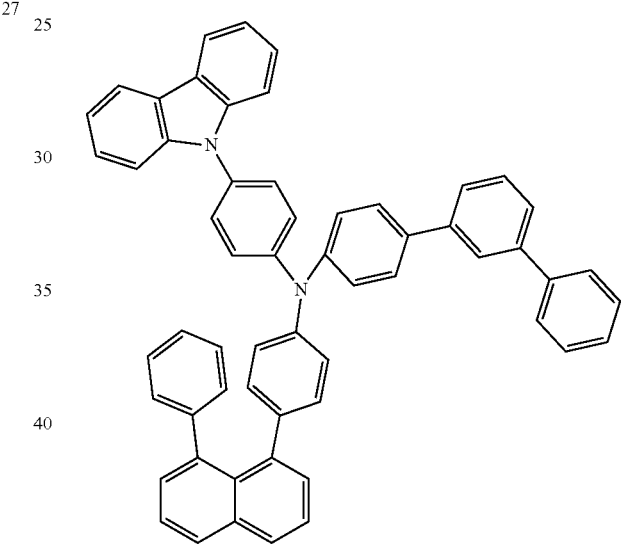
32
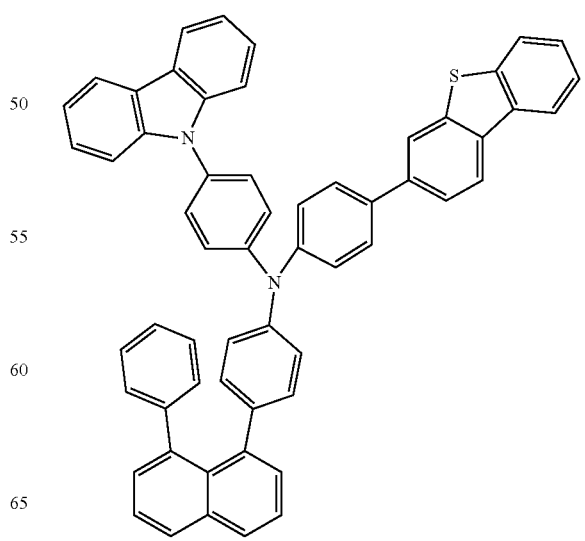

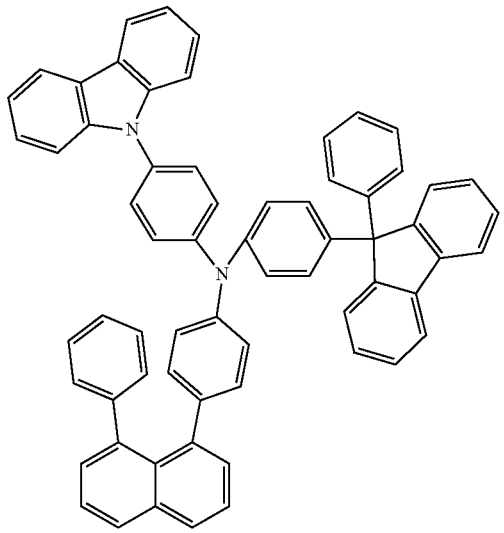
33
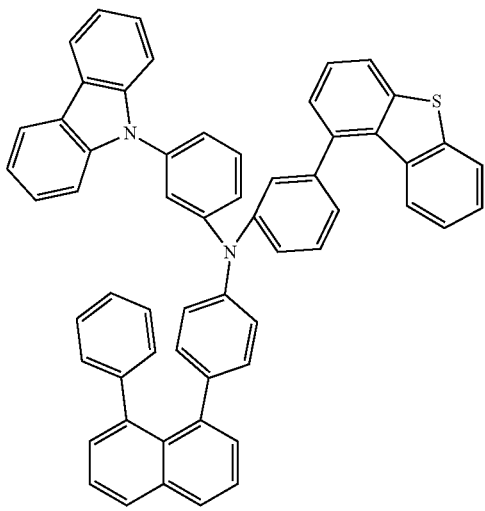
36
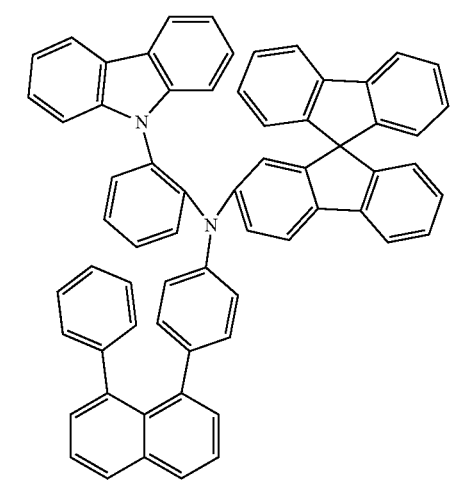
34
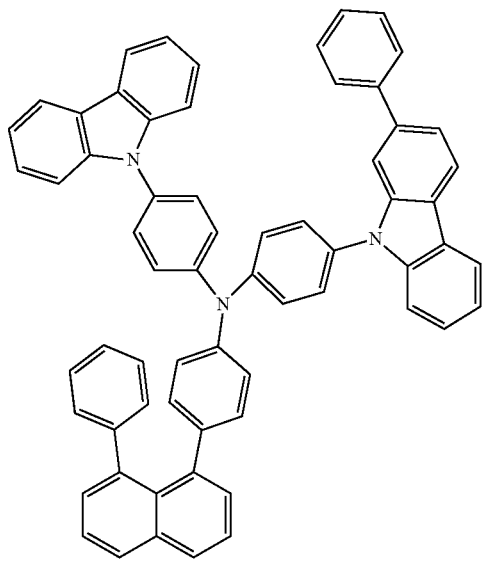
37
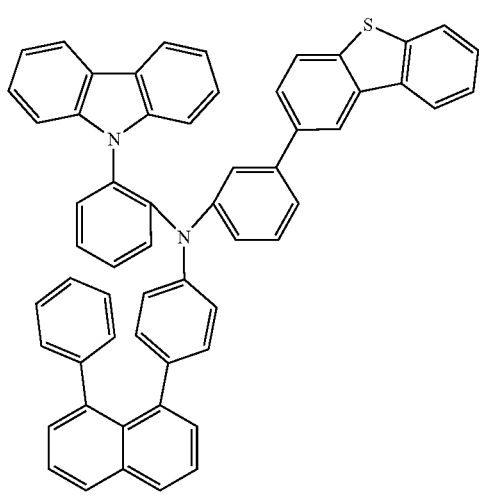
35
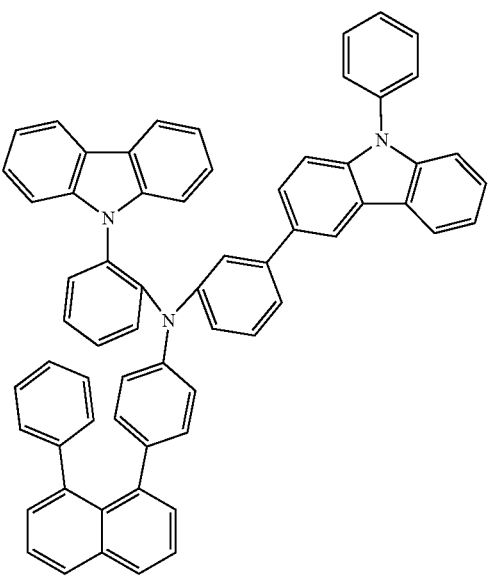
38

39
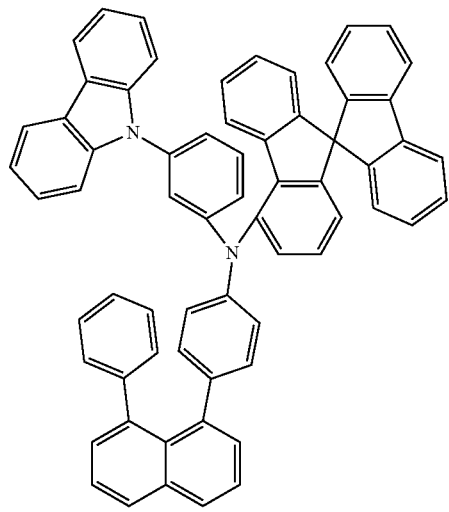
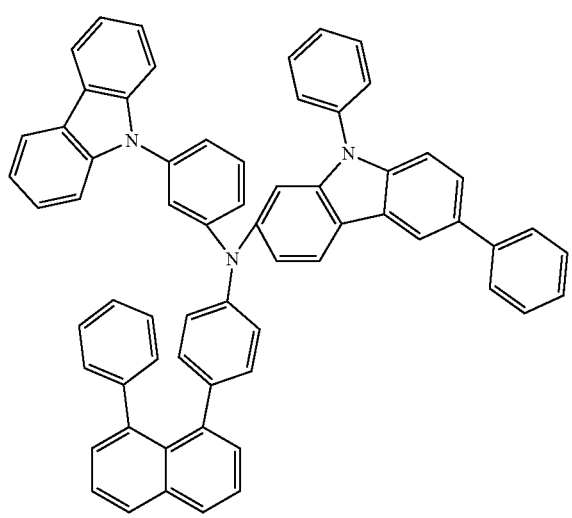
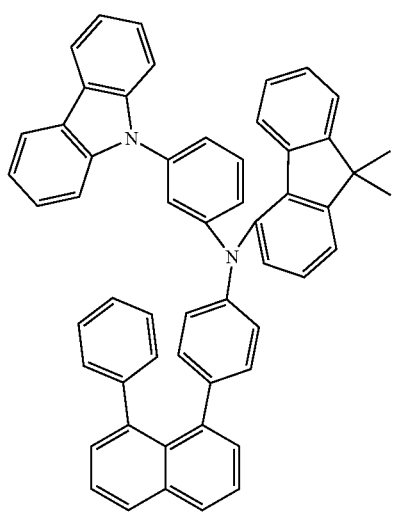
40
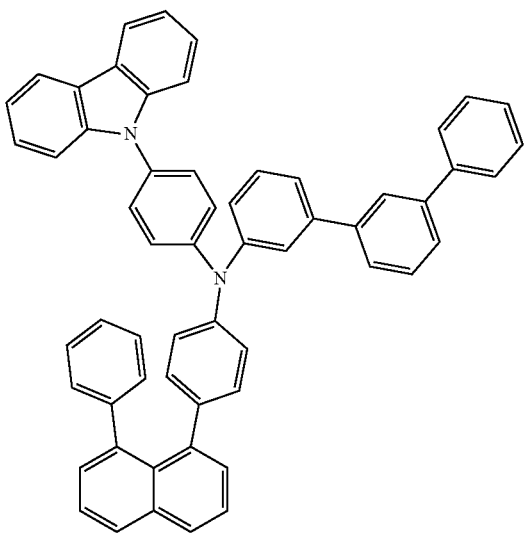
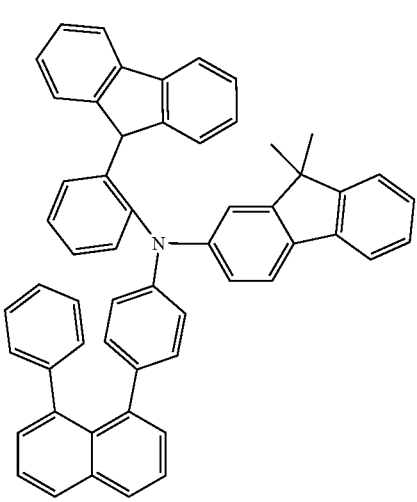
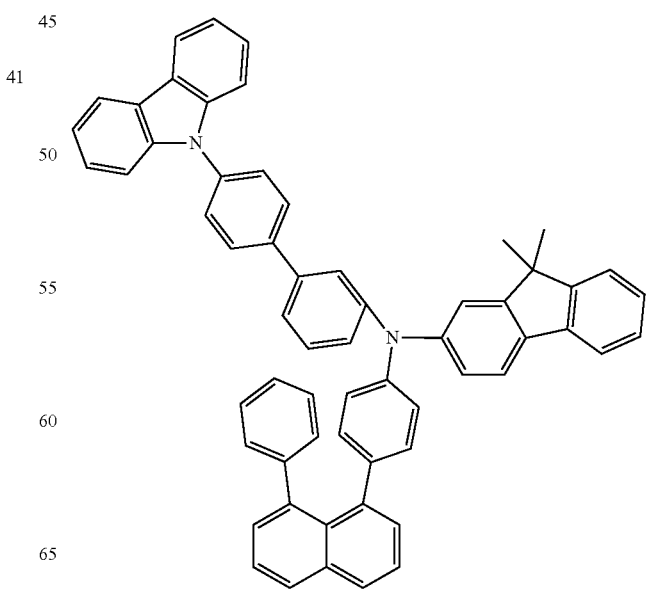

45
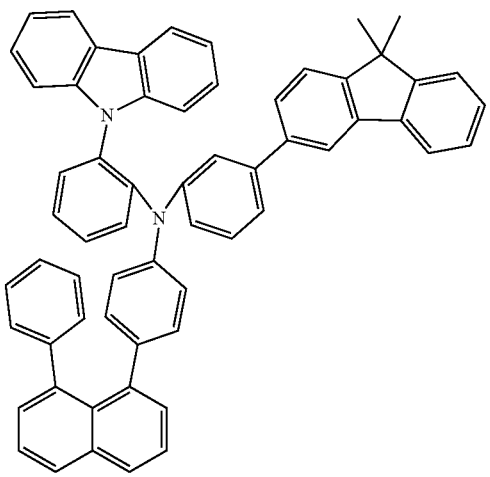
48
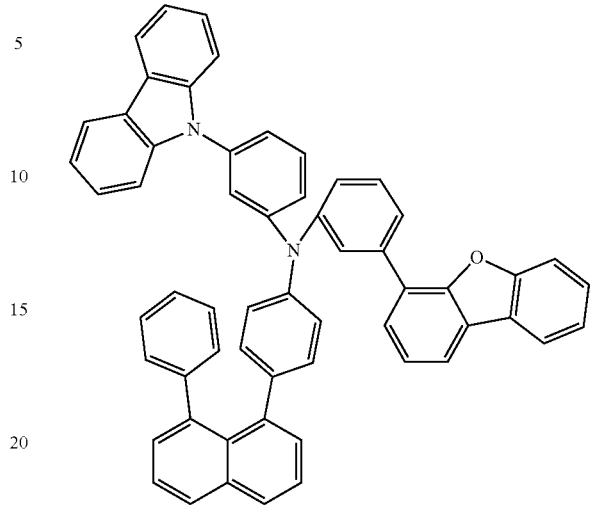
46
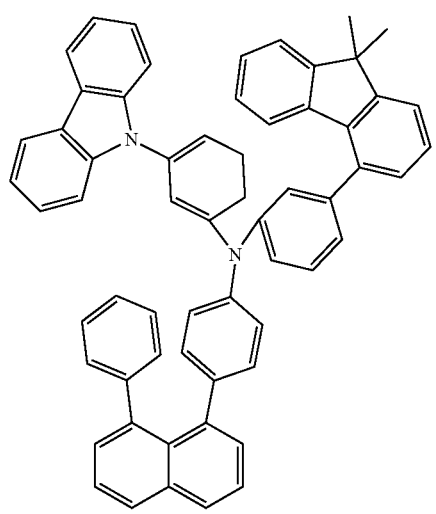
49
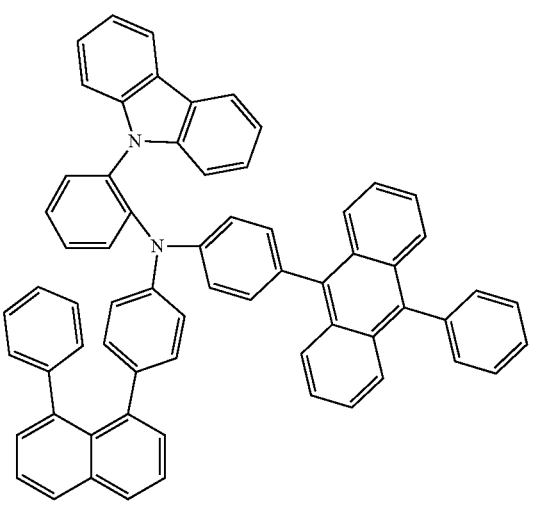
47
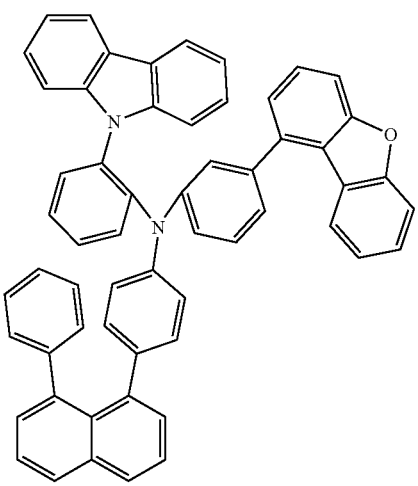
50
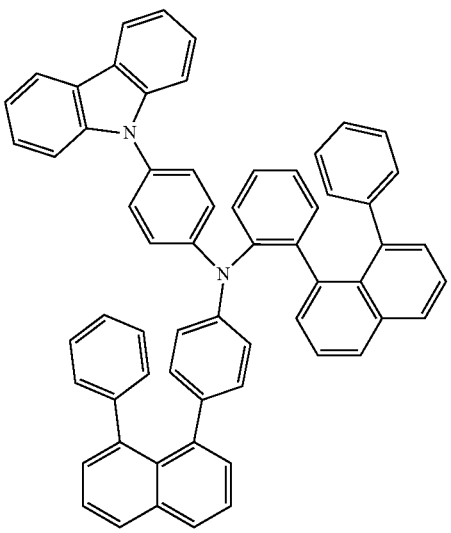

51
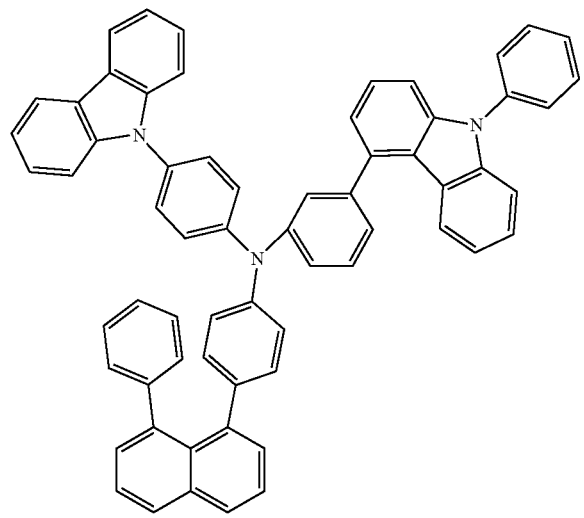
52
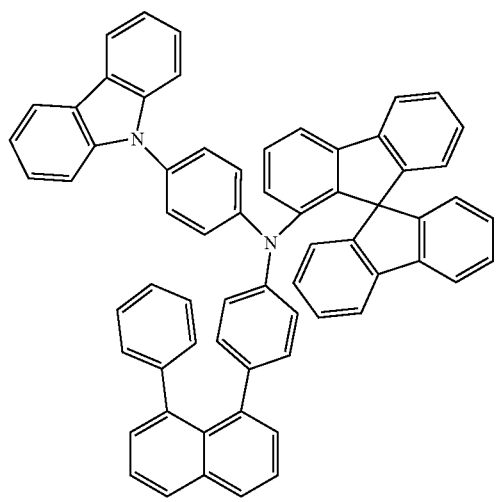
53
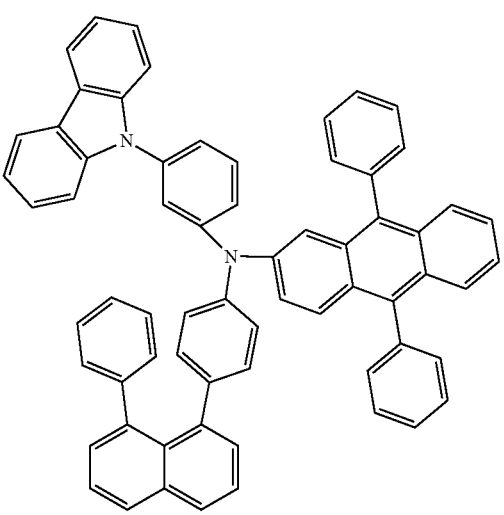
54
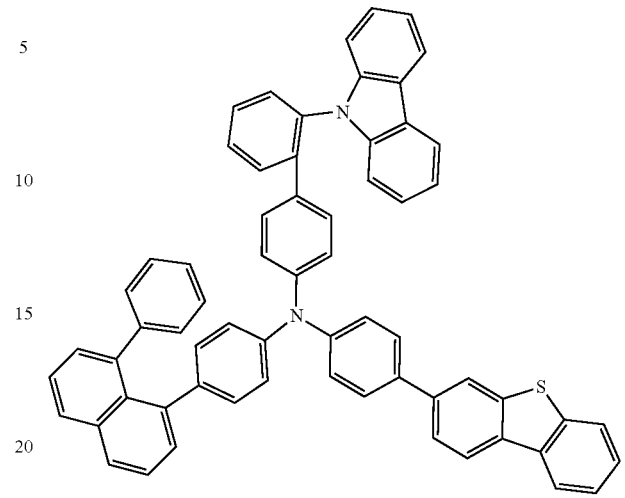
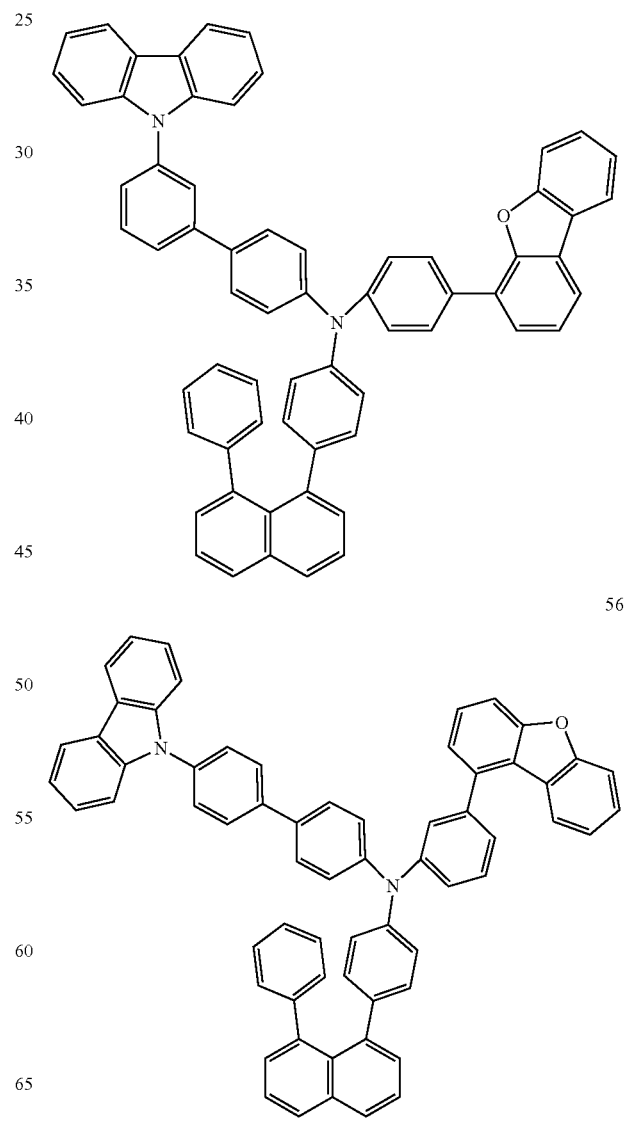

57
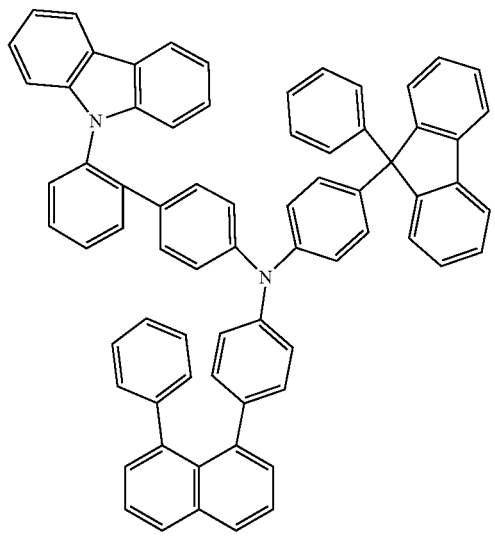
60
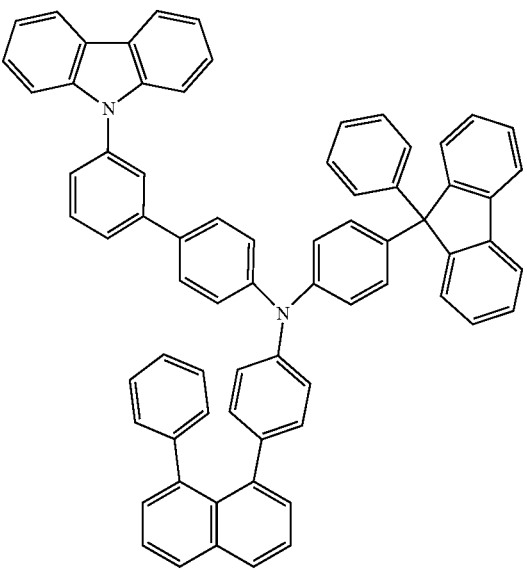
58
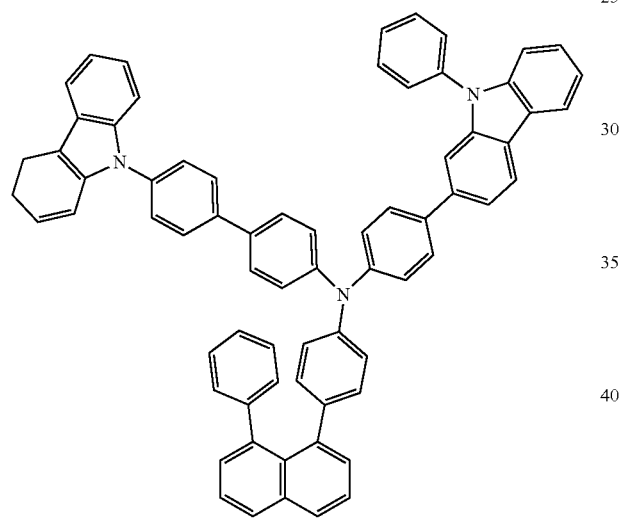
59
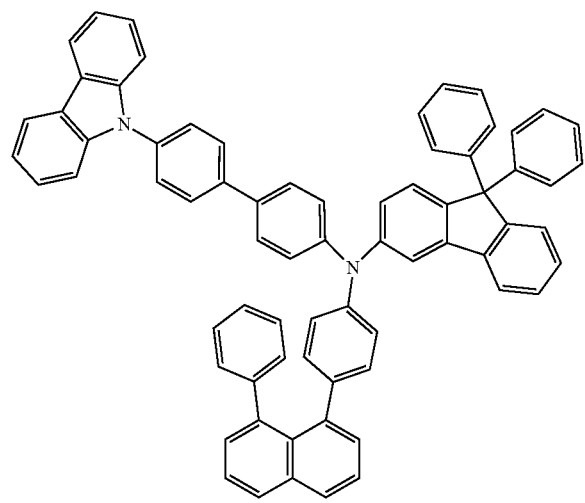
61
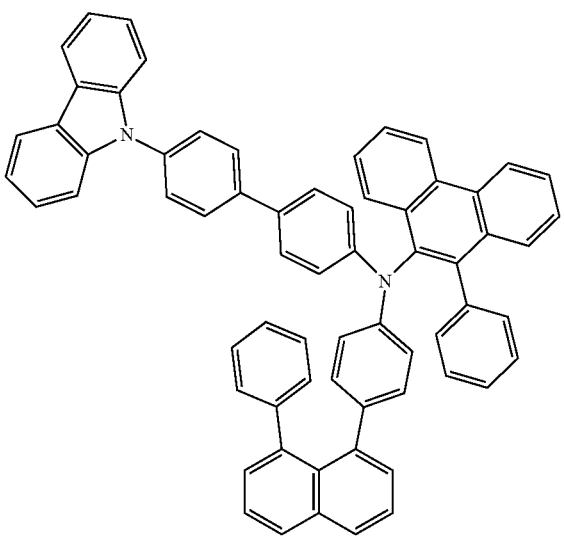

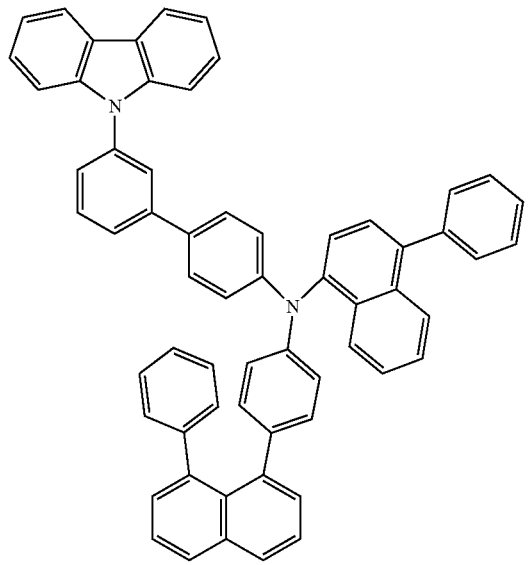
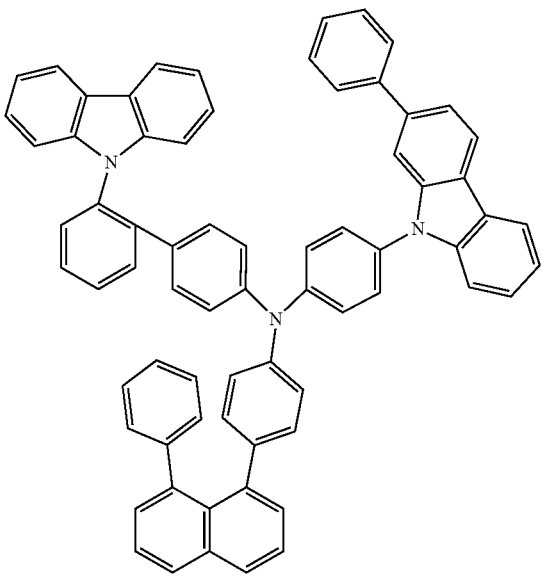

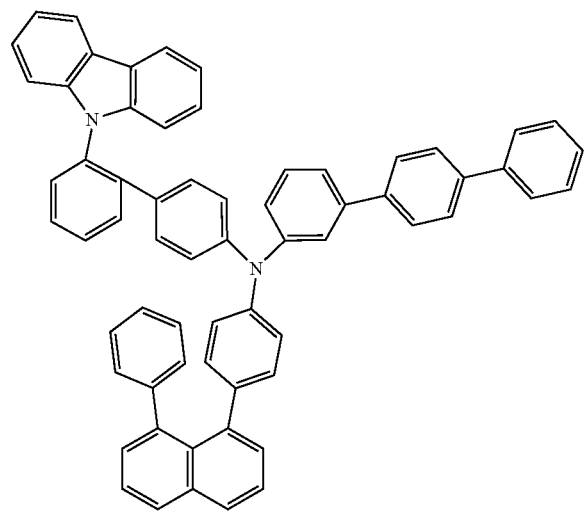
66
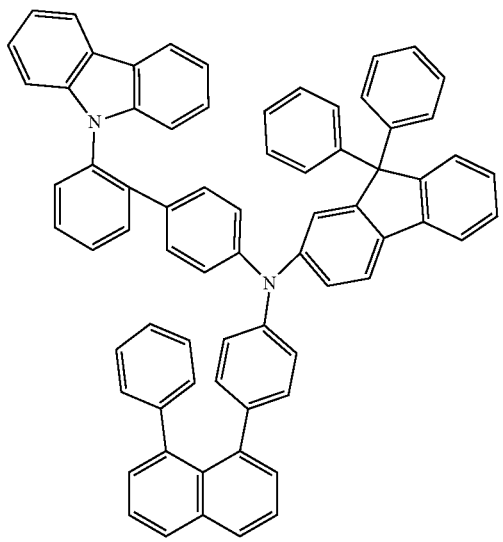
69
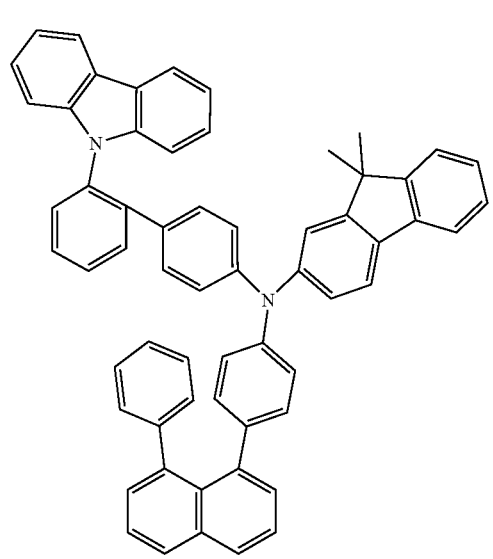
67
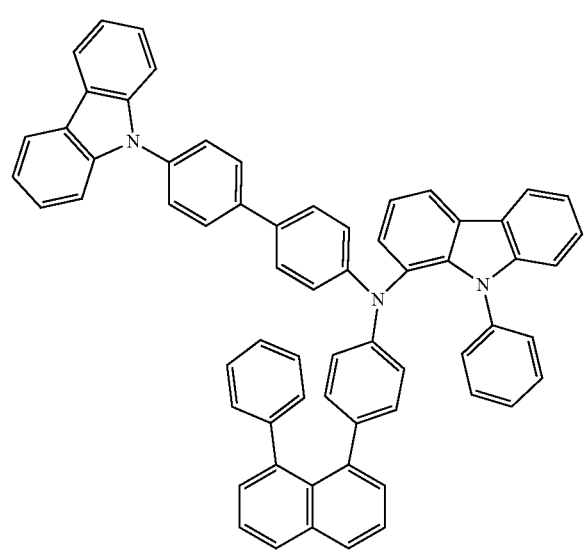
68
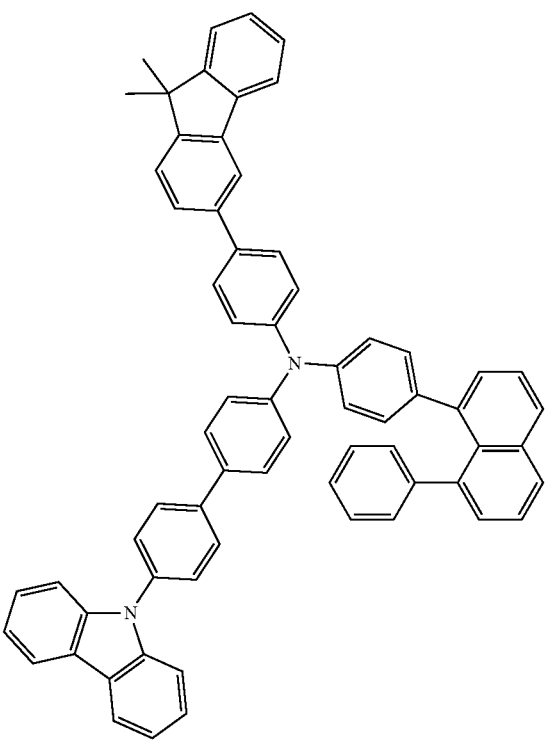
70

71
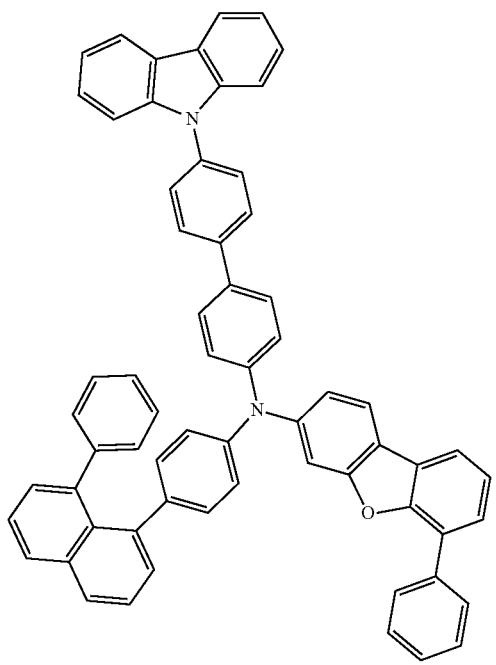
73
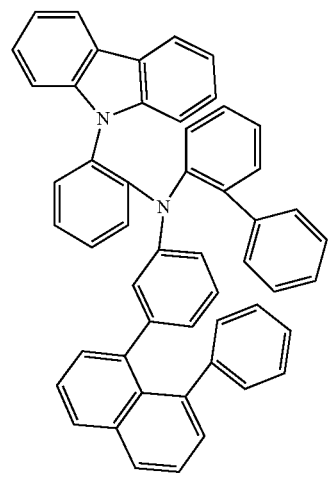
74
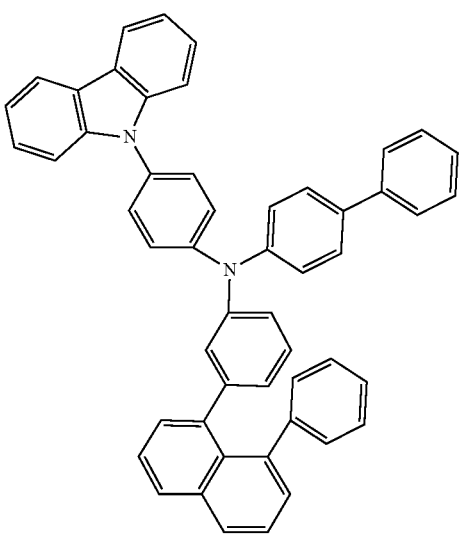
72
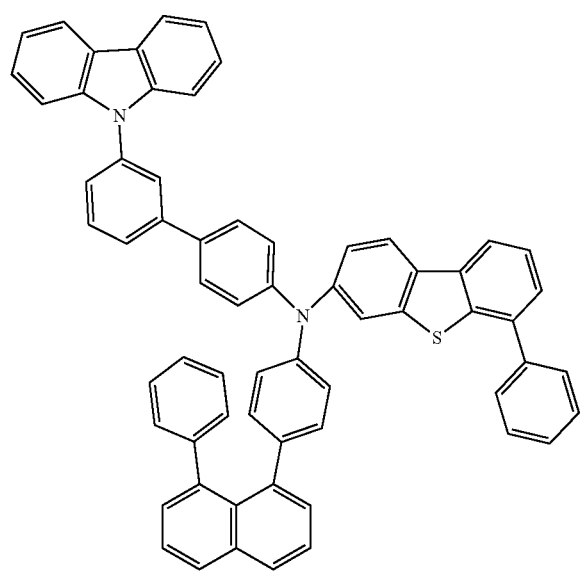
75
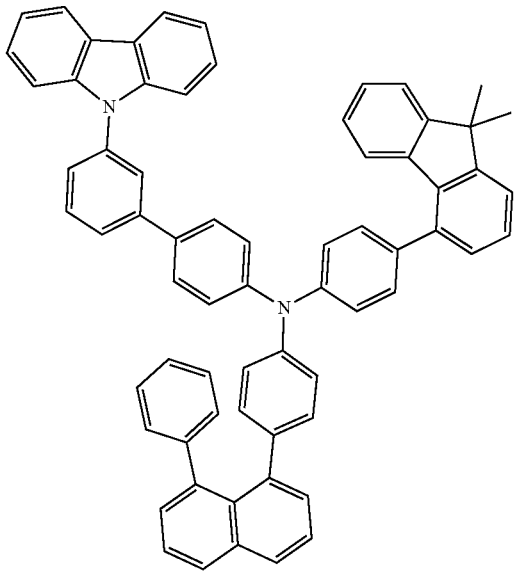

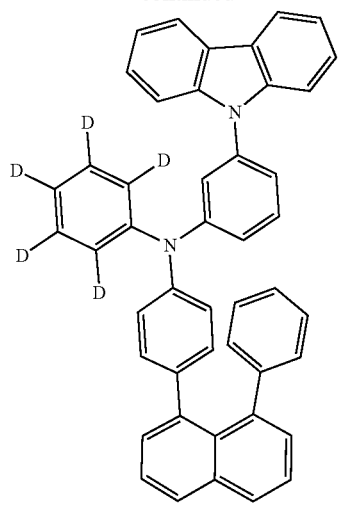
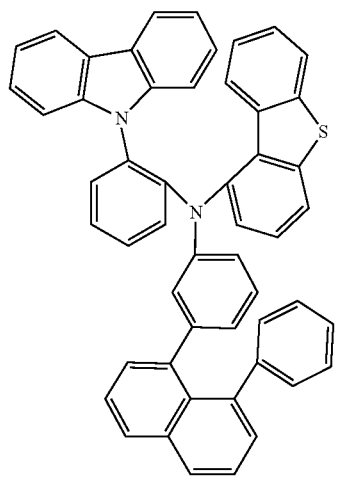
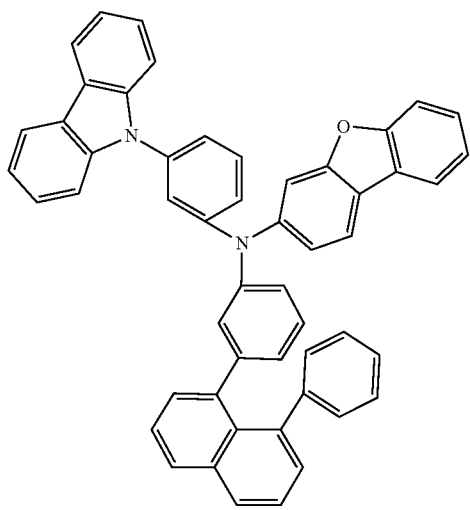
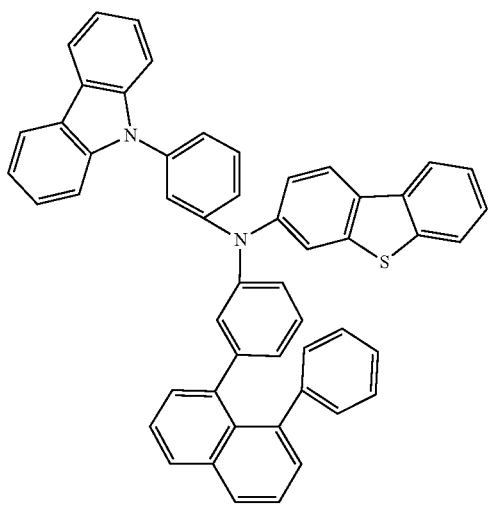
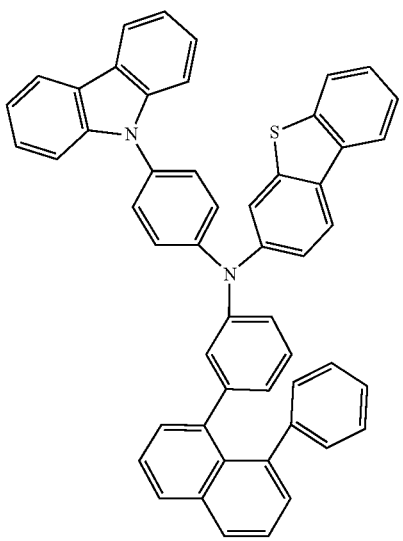
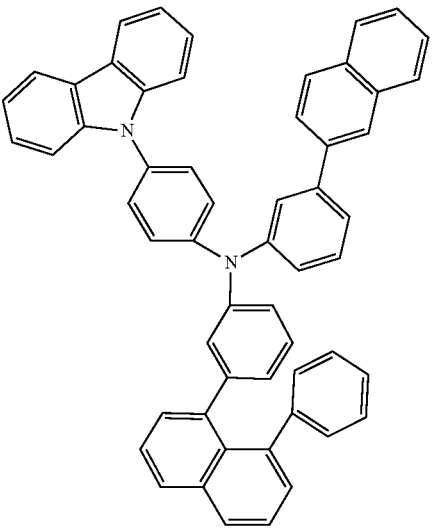

82
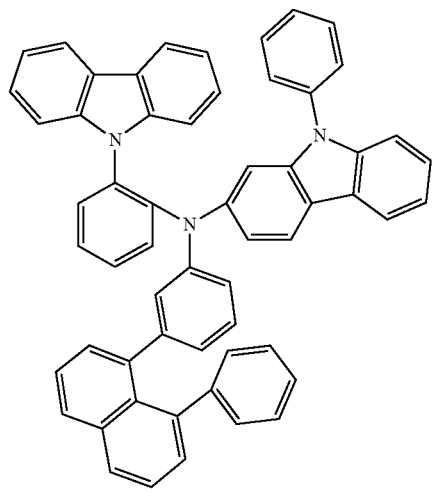
83
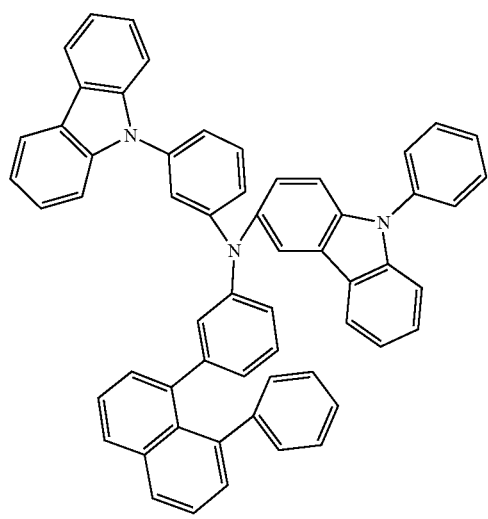
84
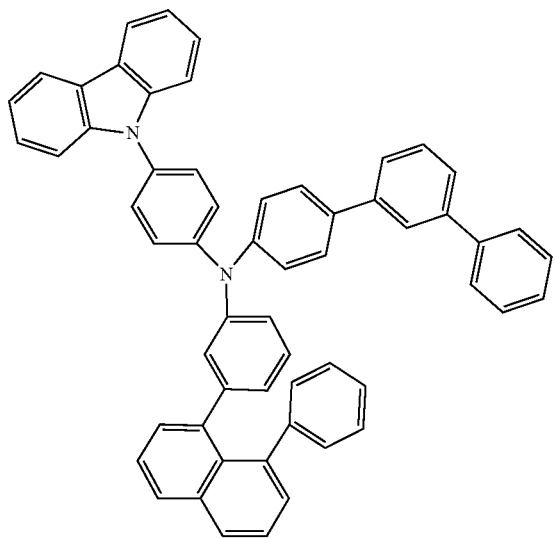
85
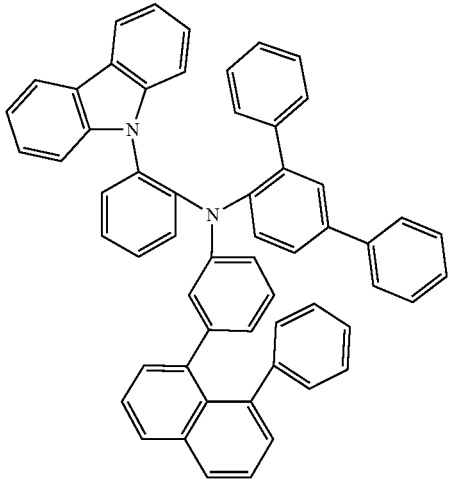
86
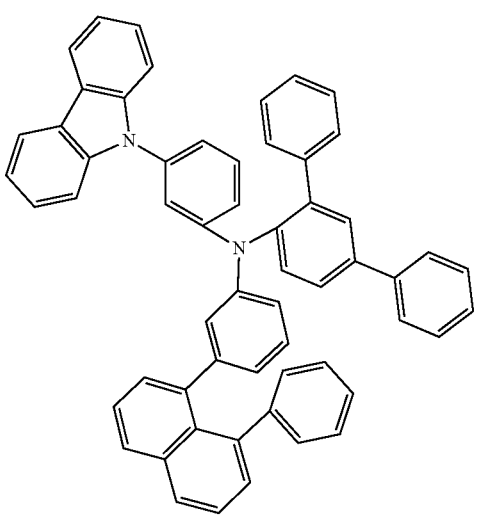
87
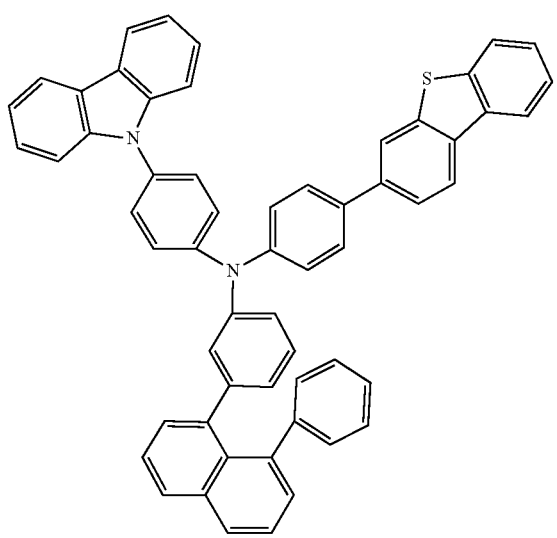

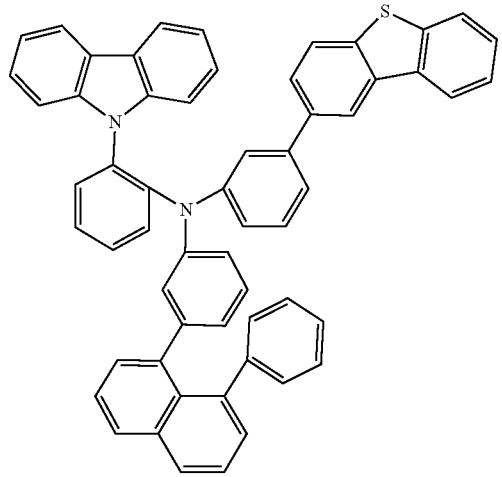
88
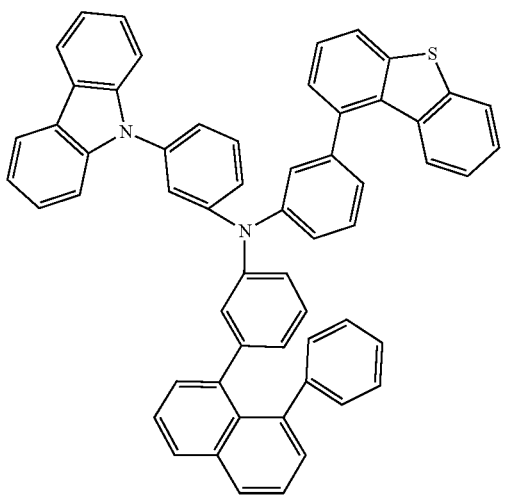
89
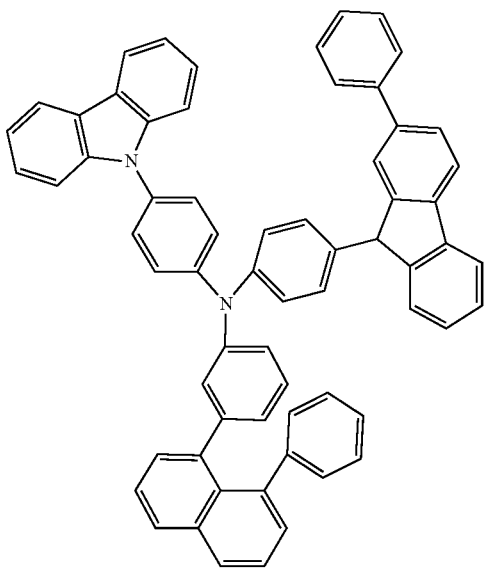
90
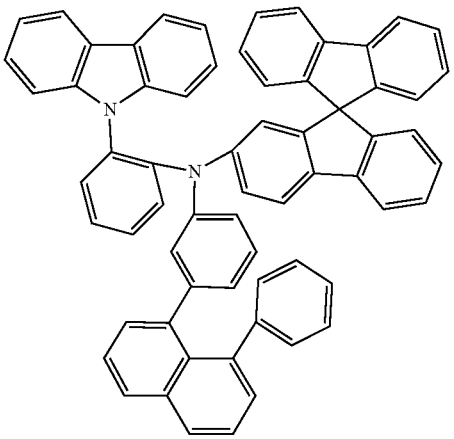
91
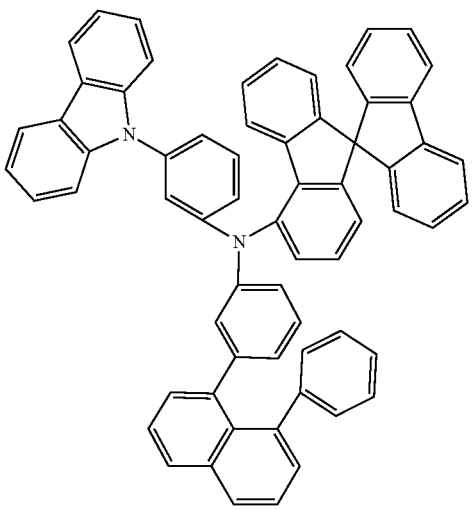
92
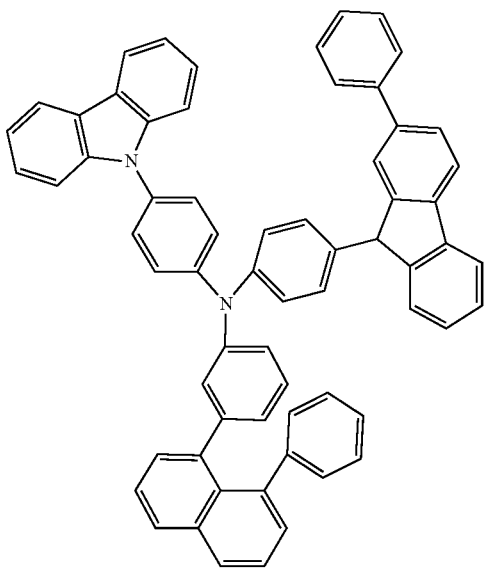
93

94
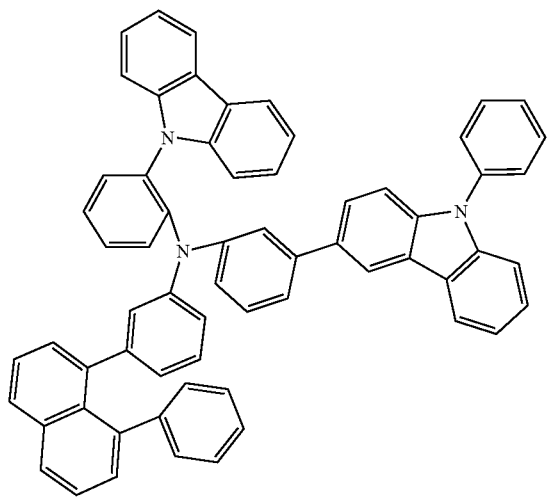
95
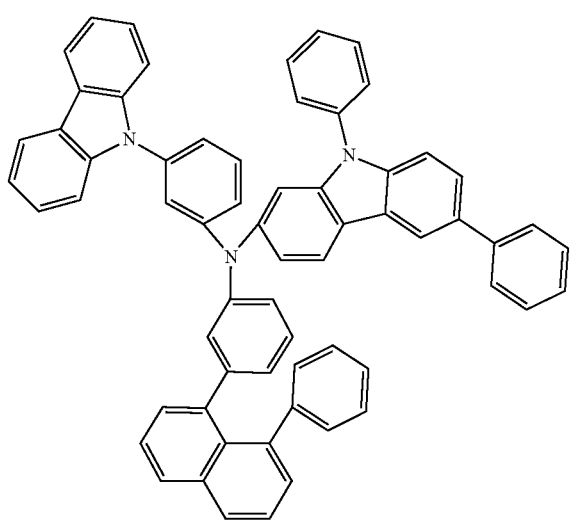
96
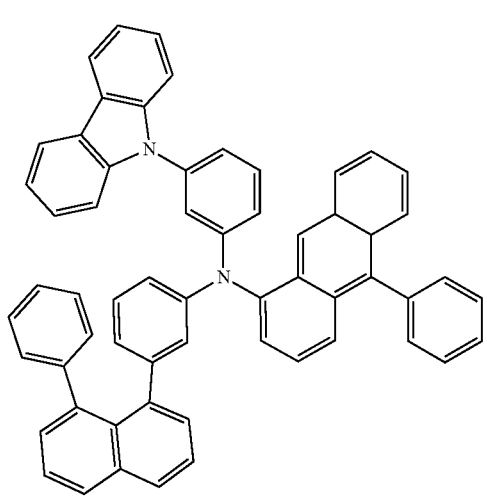
97
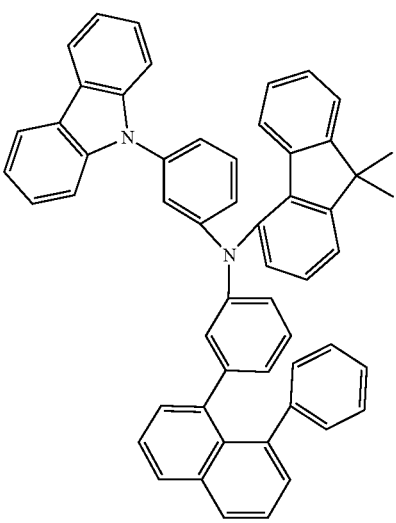
98
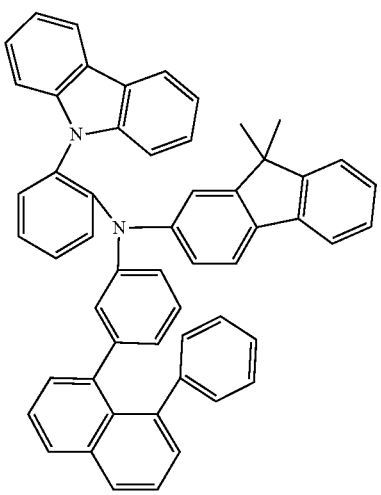
99
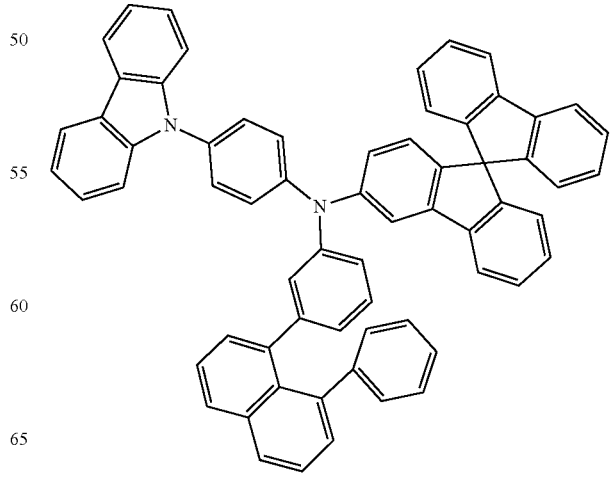

100
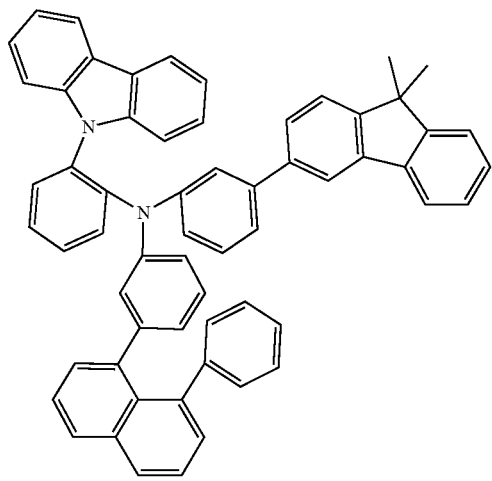
101
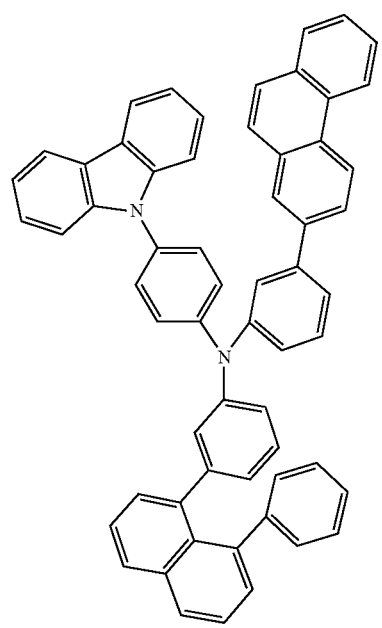
102
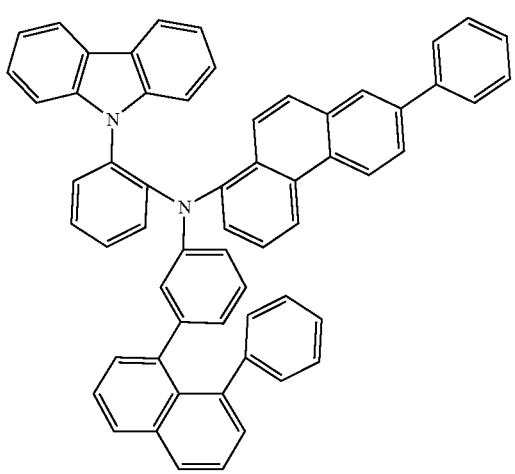
103
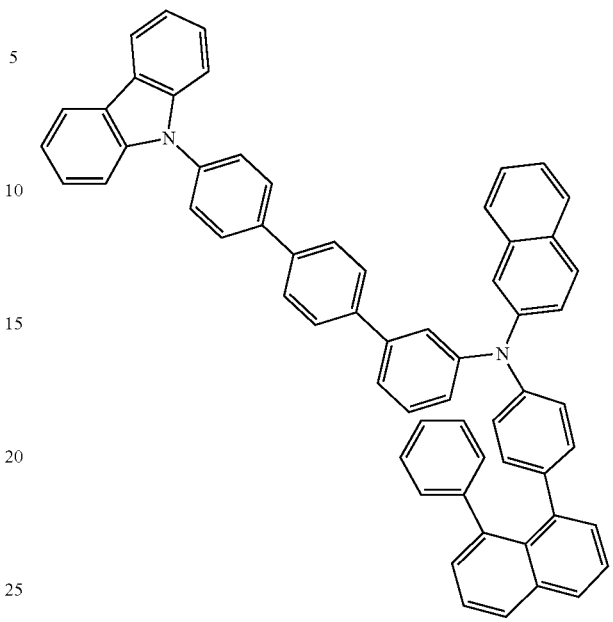
104
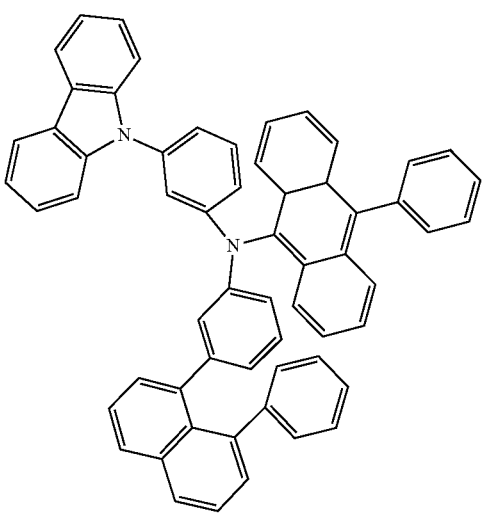

105
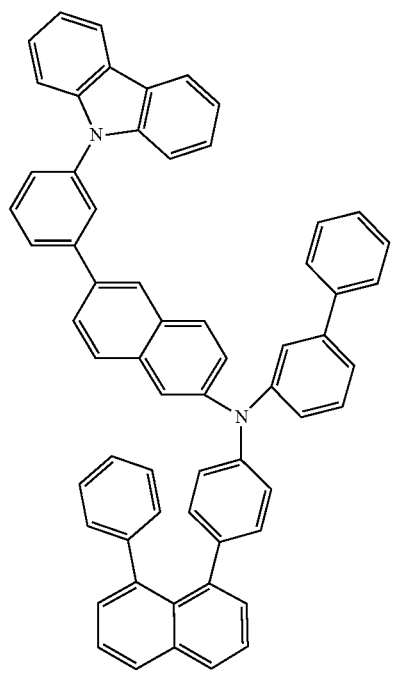
107
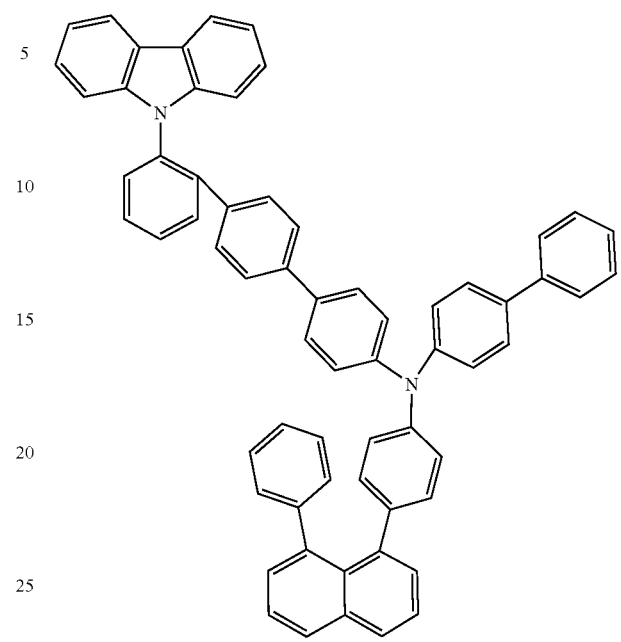
106
108
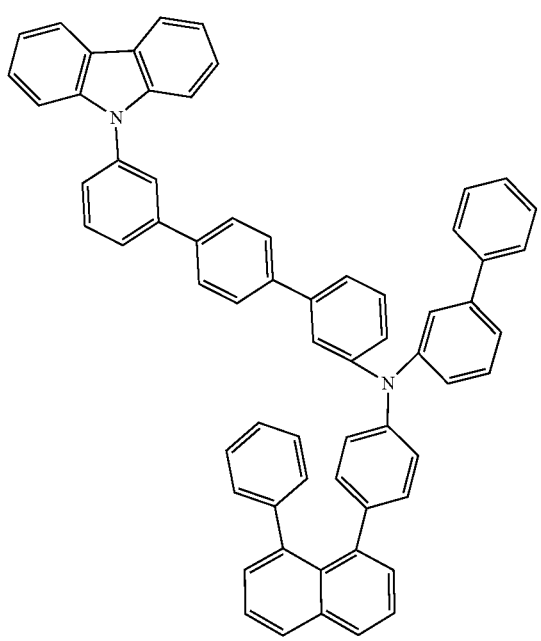

109
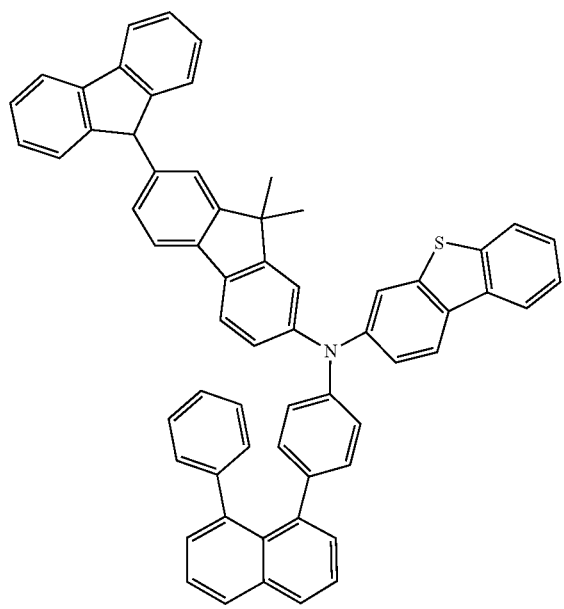
110
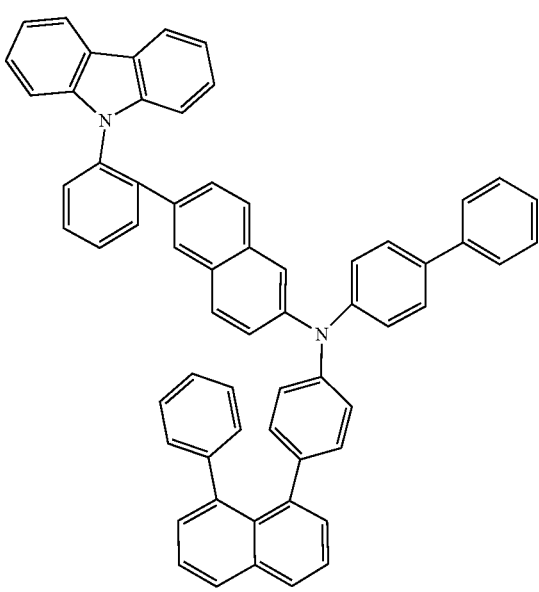
111
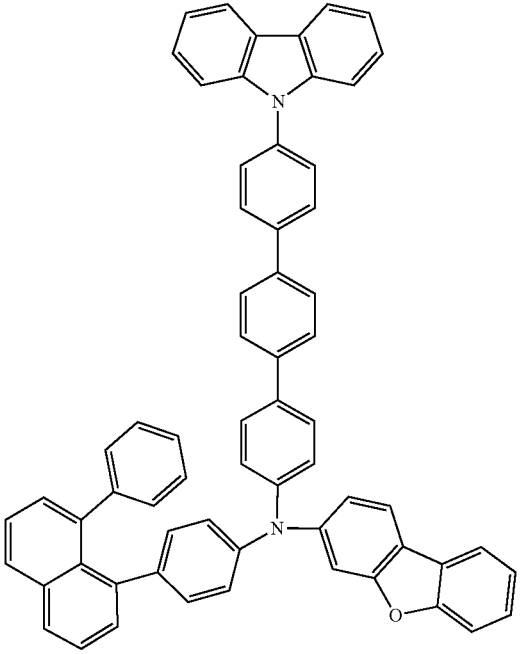
112
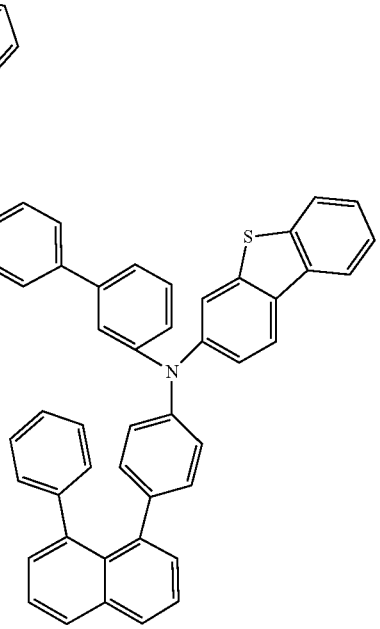

-continued
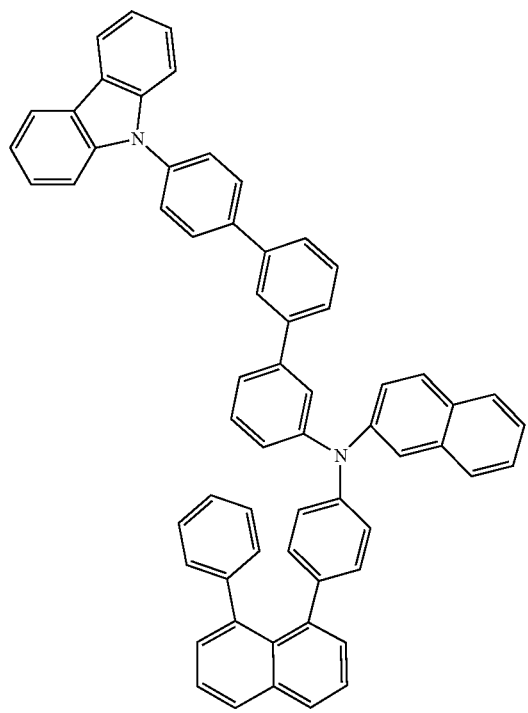
113
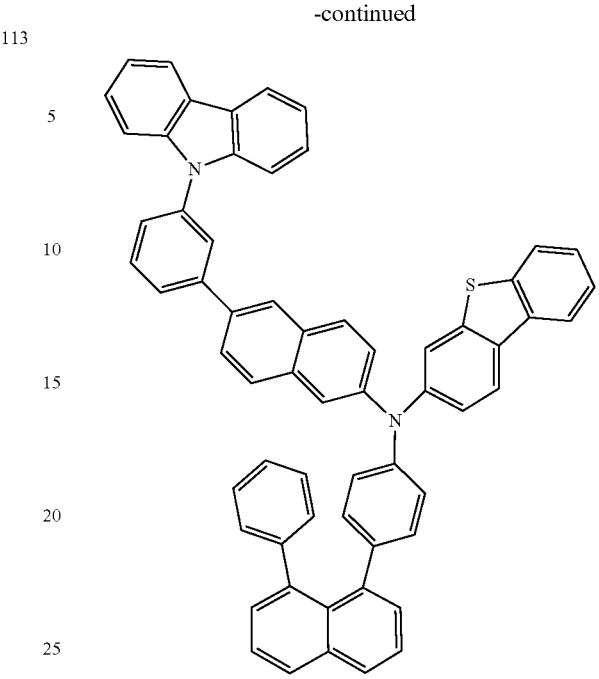
115
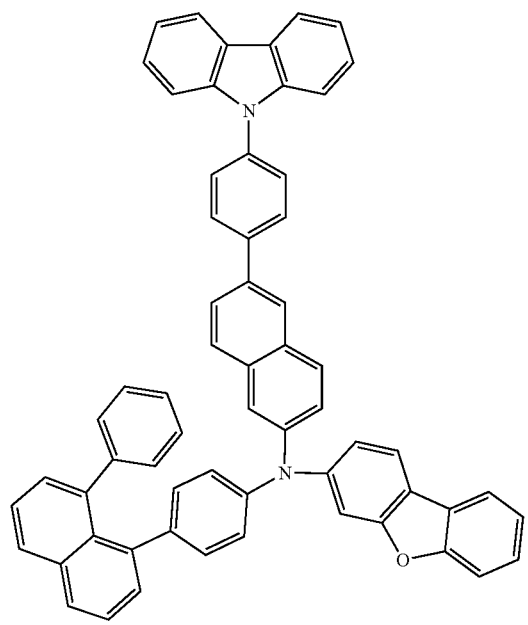
114
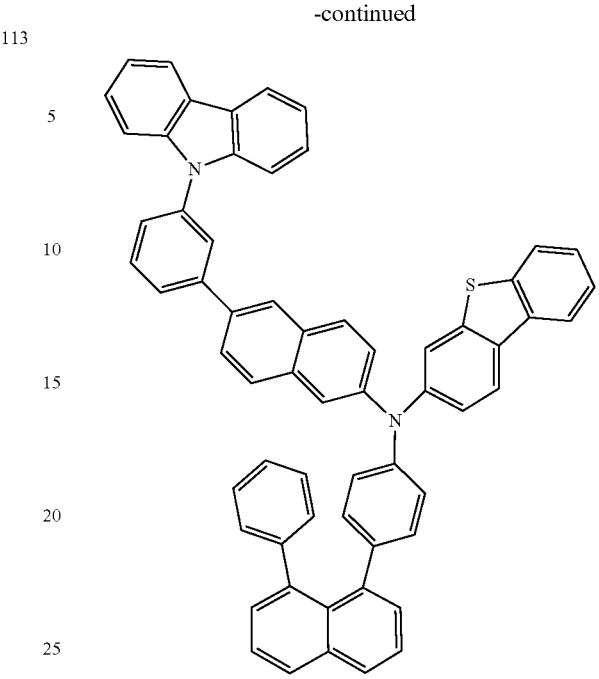
116

117
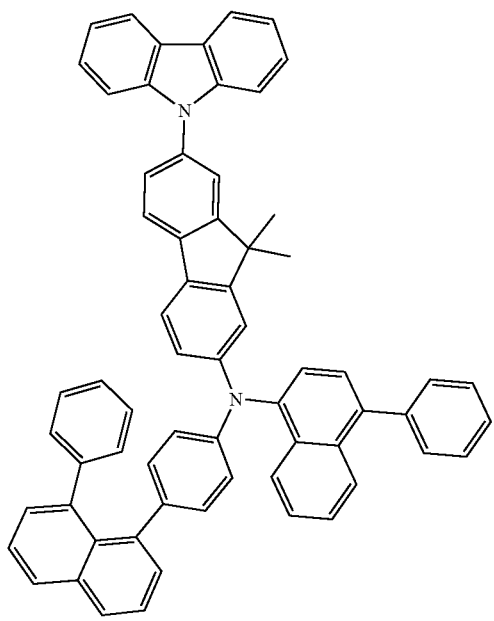
118
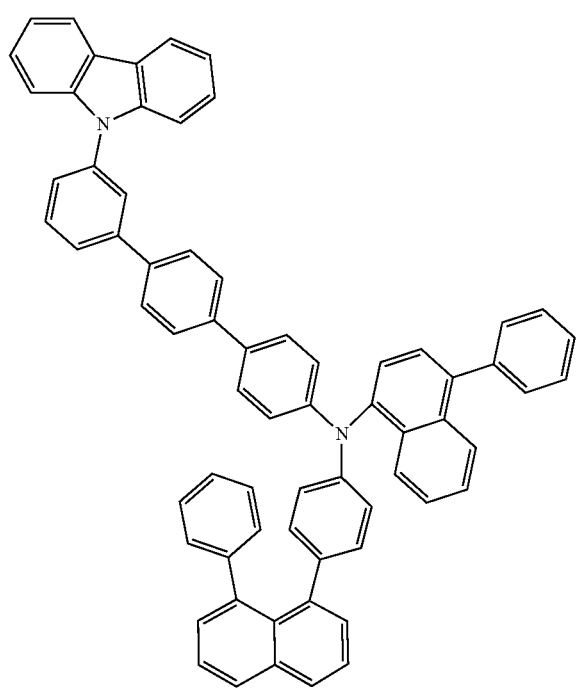
119
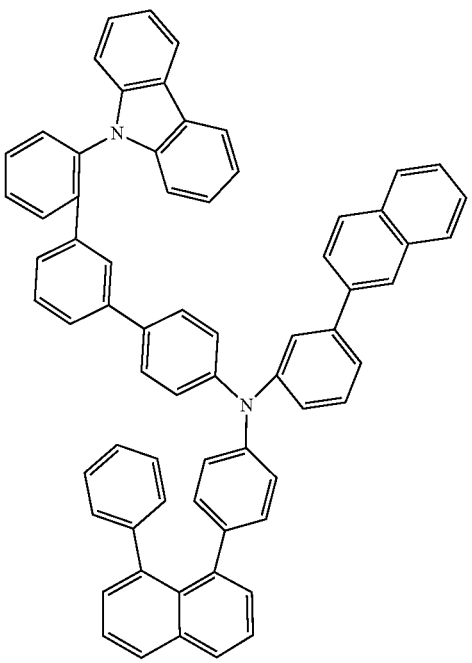
120
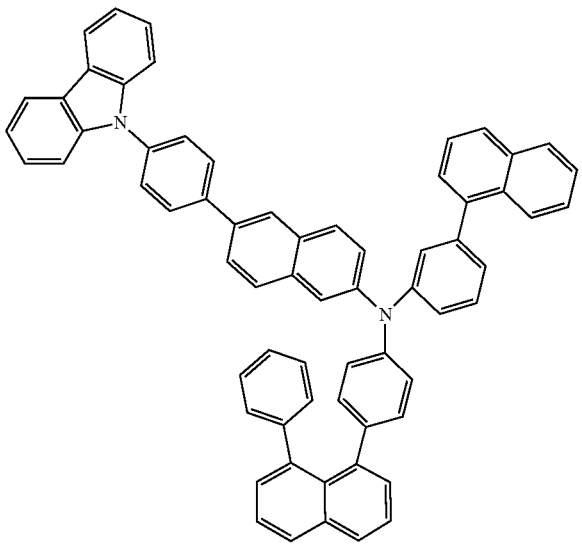

121
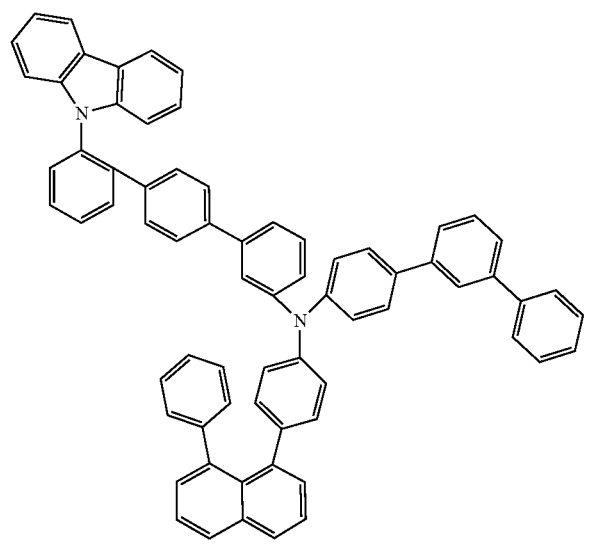
122
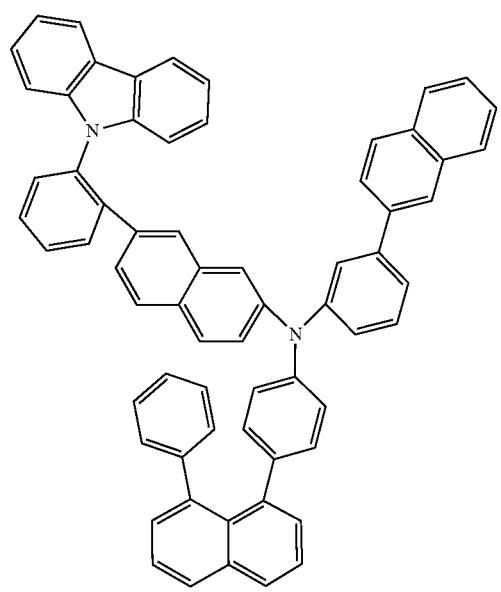
123
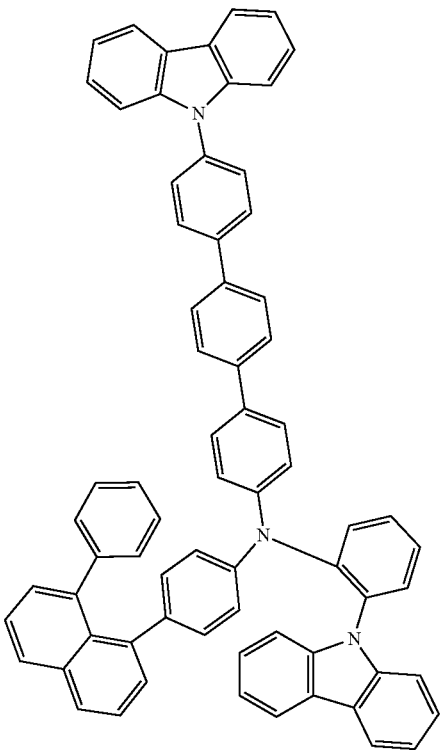
124
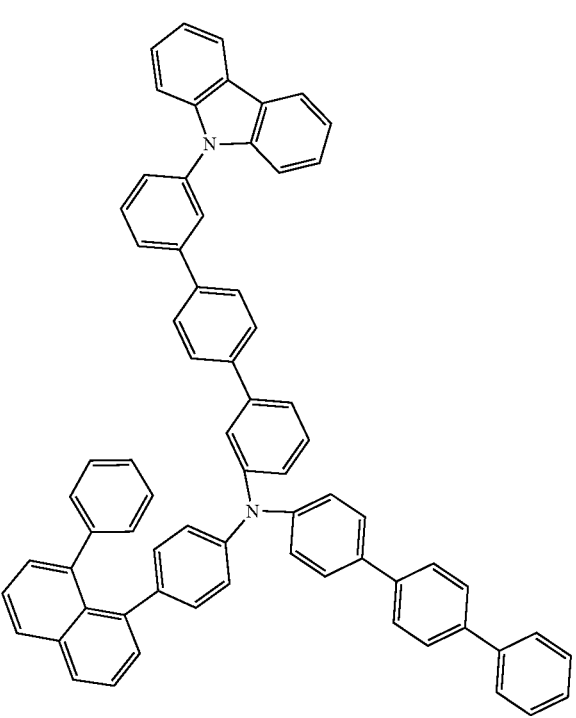

125
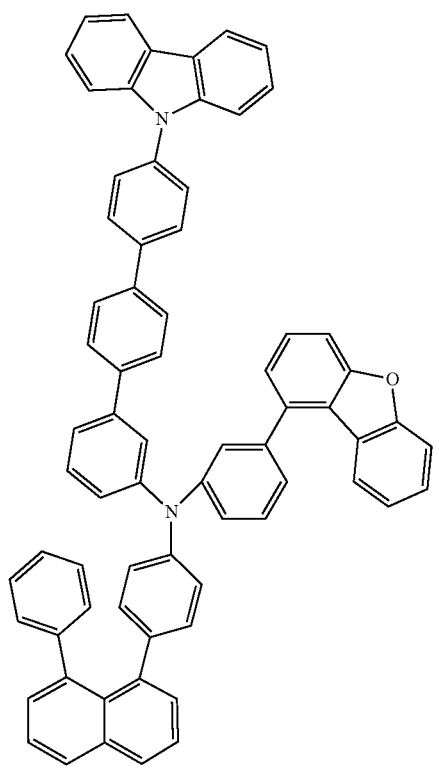
127
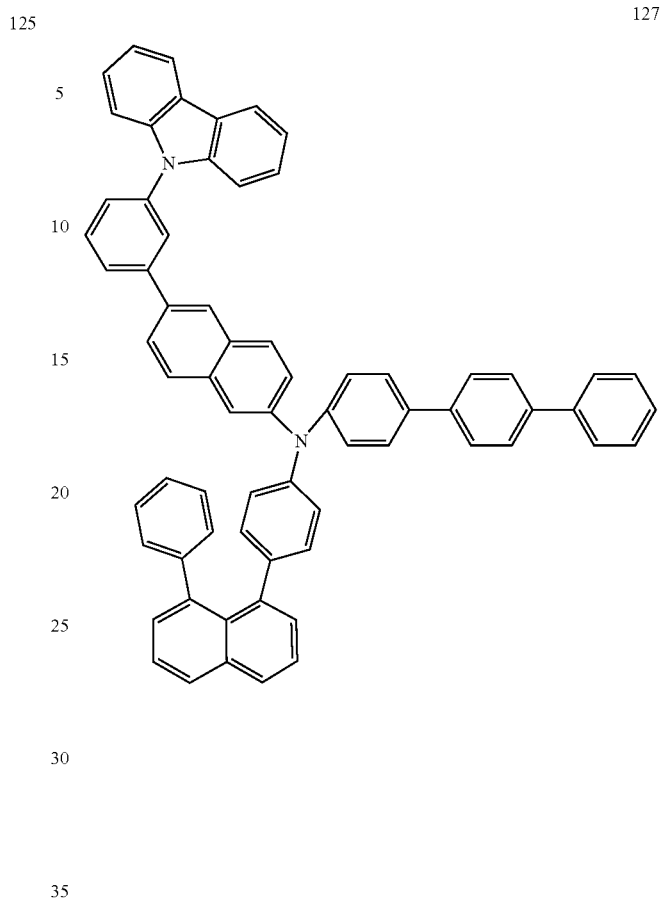
126
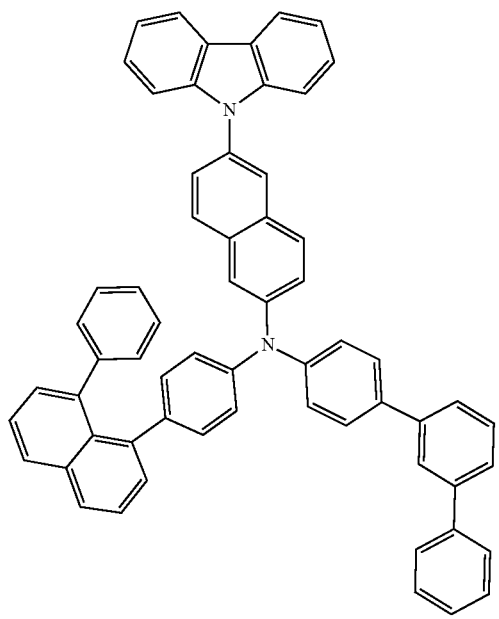
128
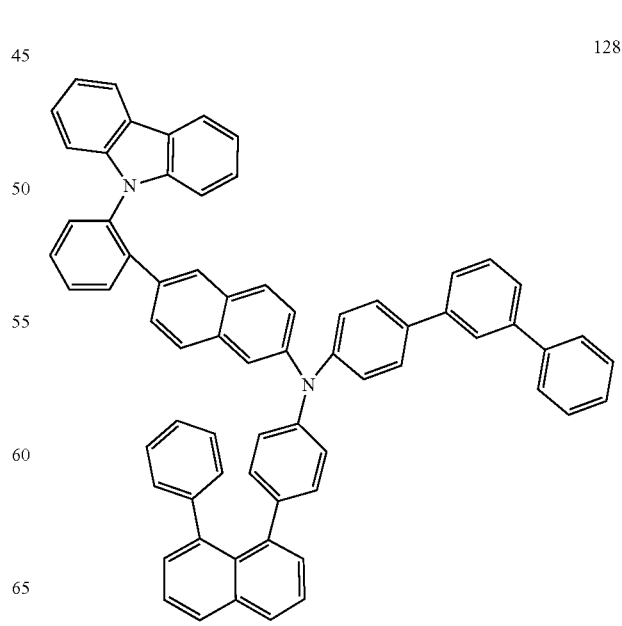

129
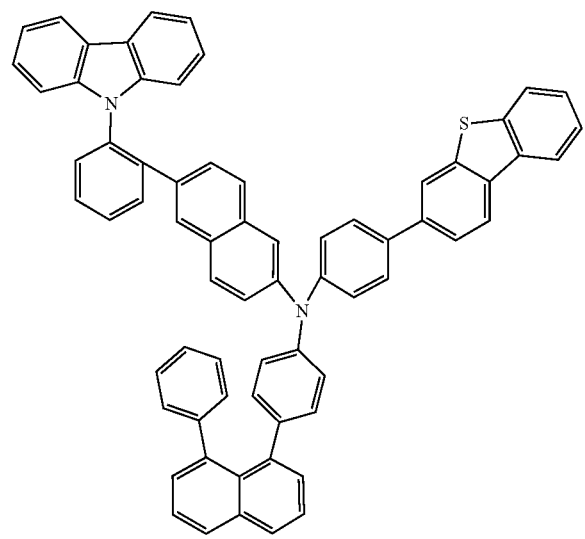
131
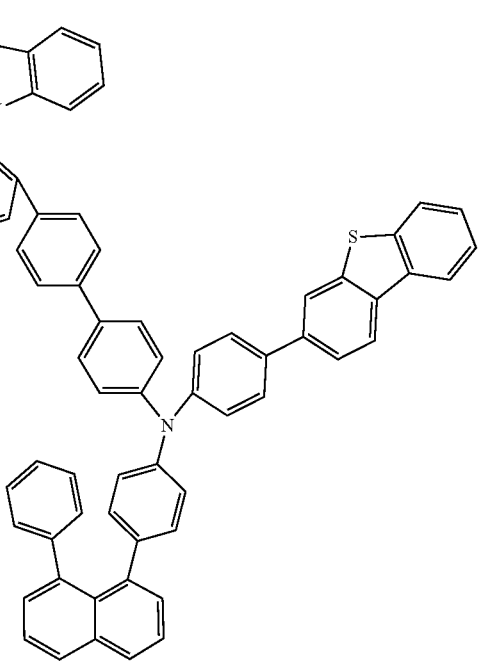
130
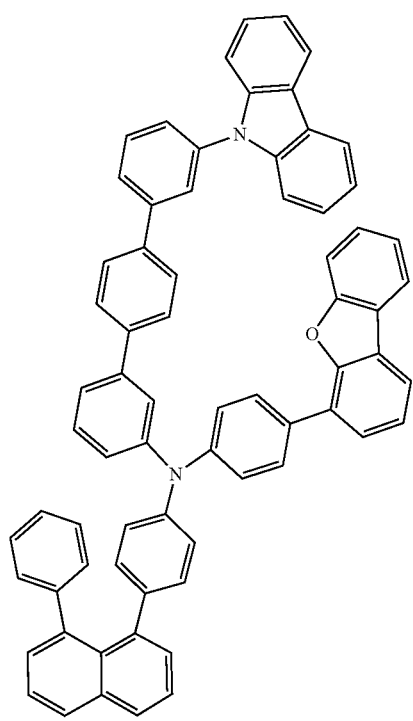
132
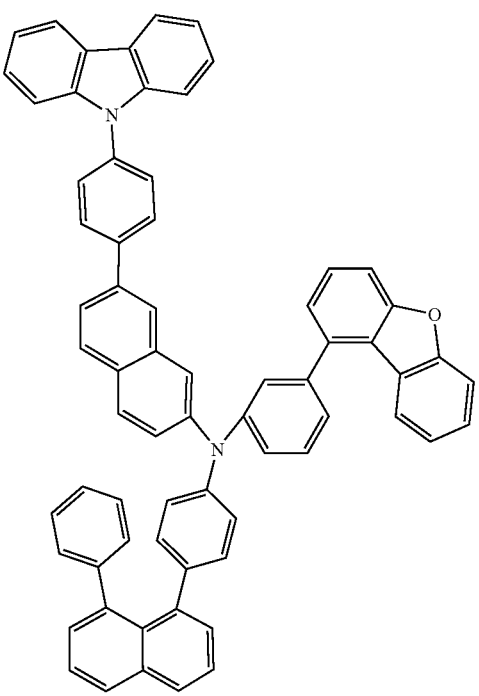

133
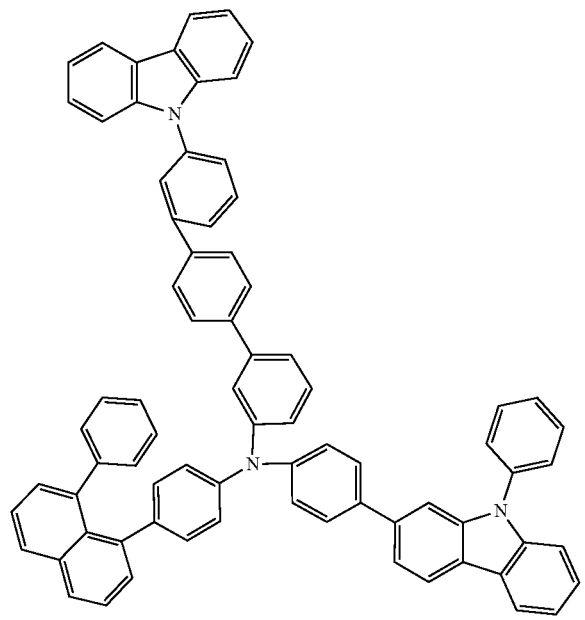
135
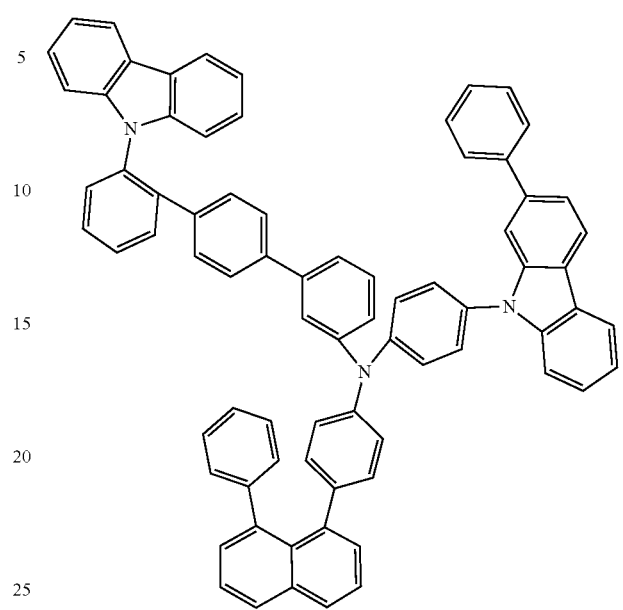
134
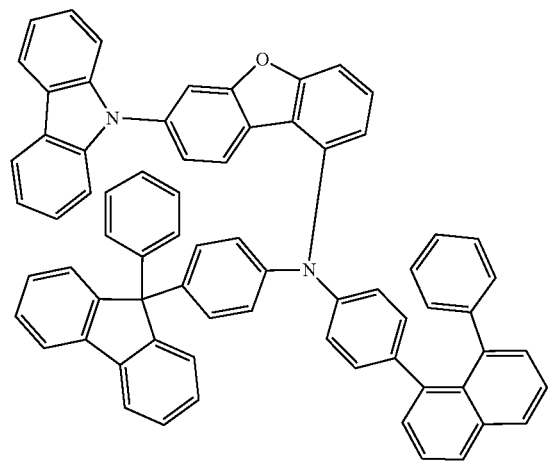
136
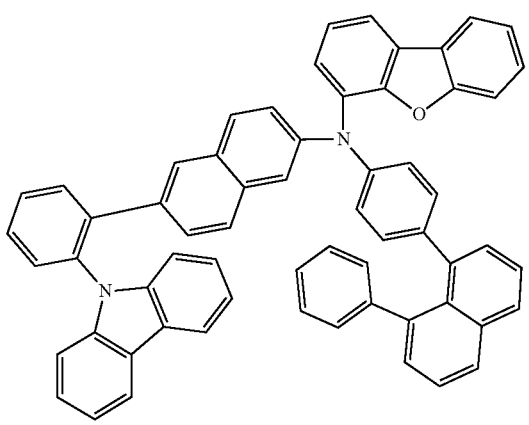

137
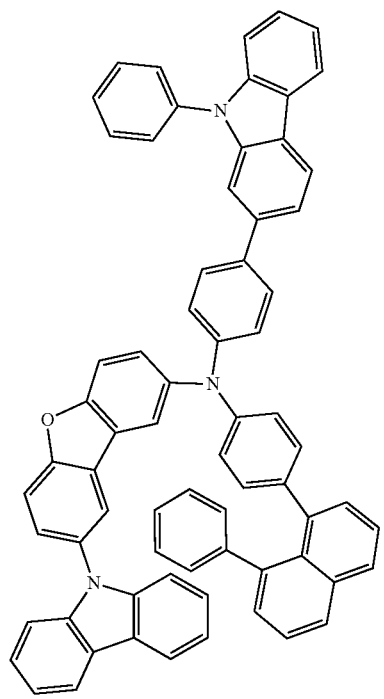
139
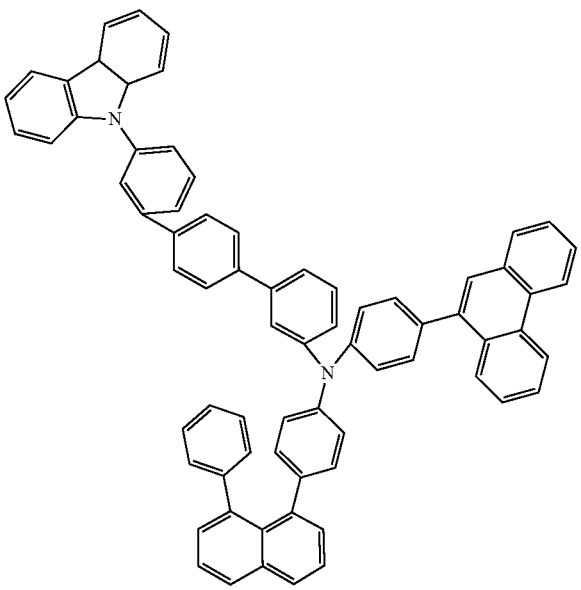
138
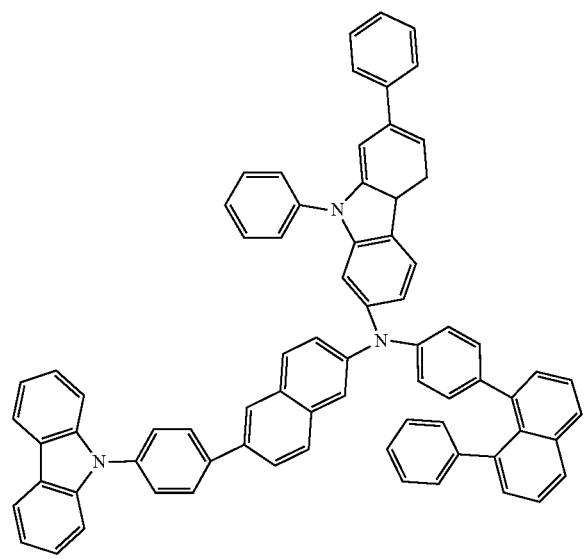
140
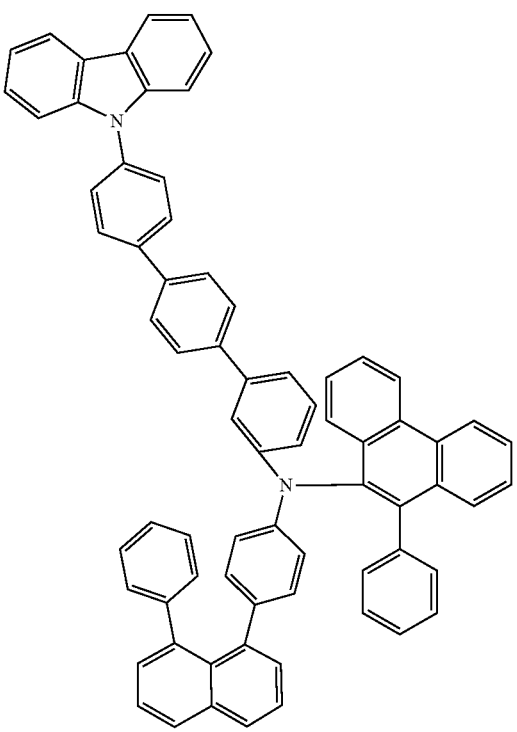

81
-continued
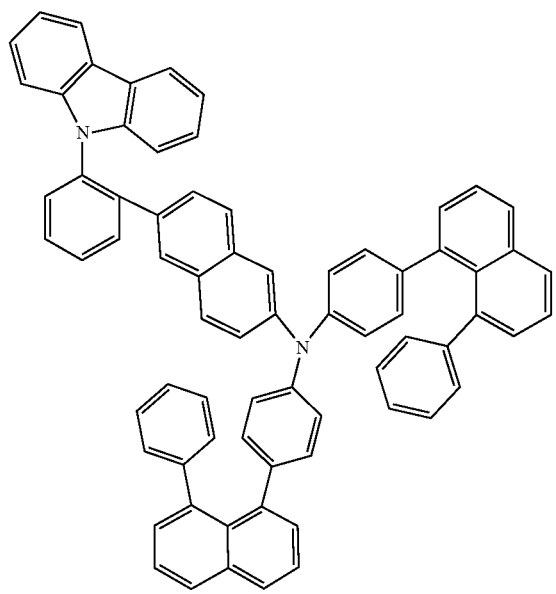
141
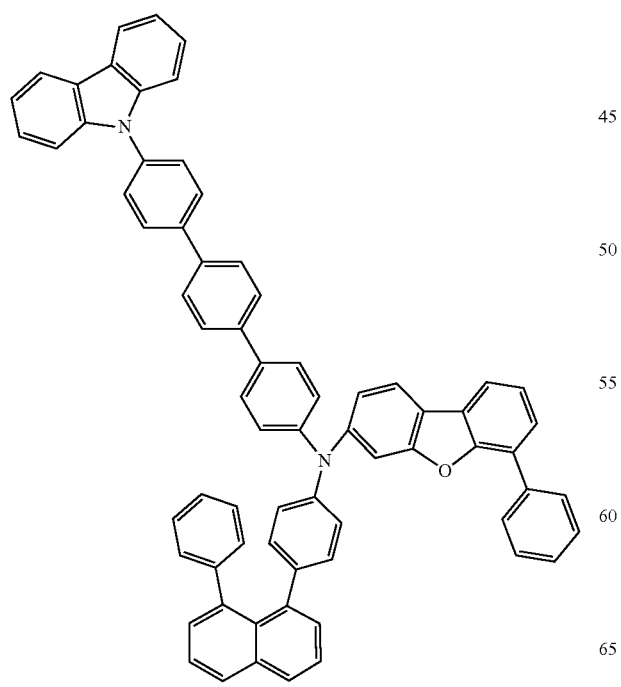
142
82
-continued
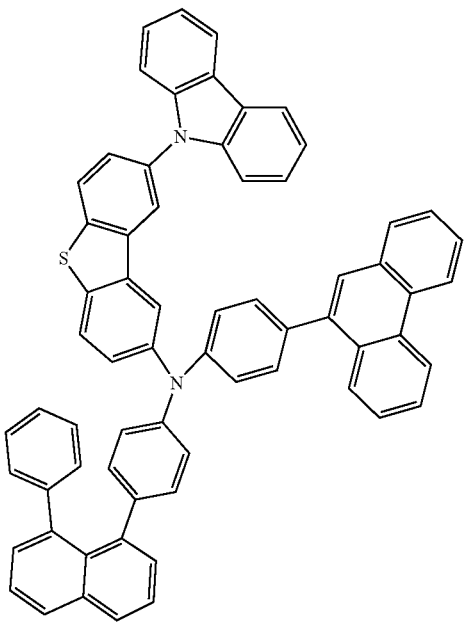
143
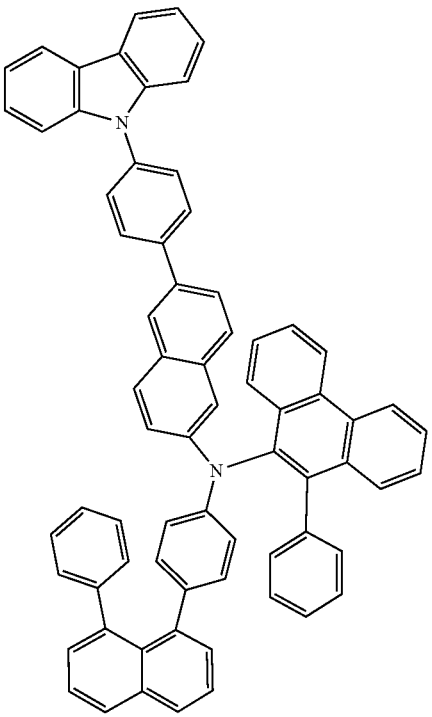
144

146
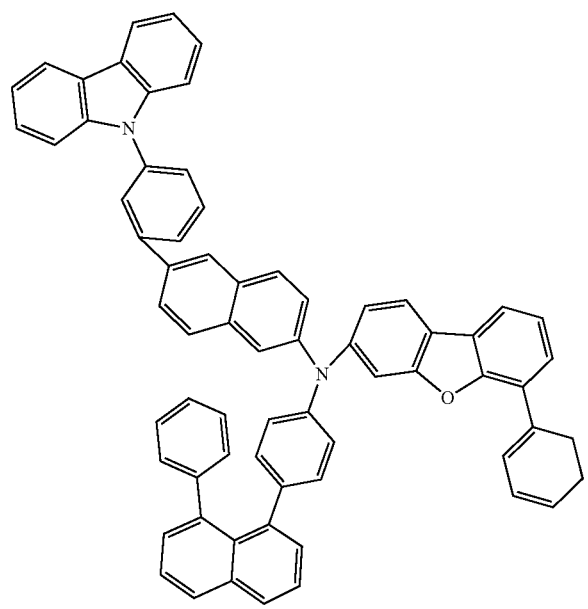
148
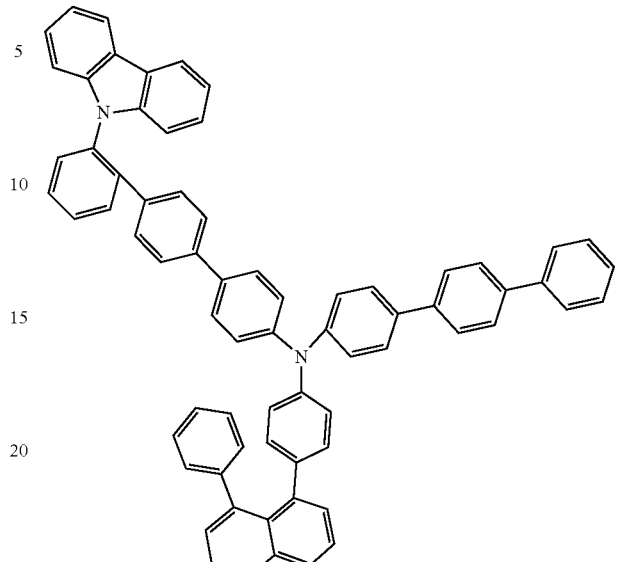
147
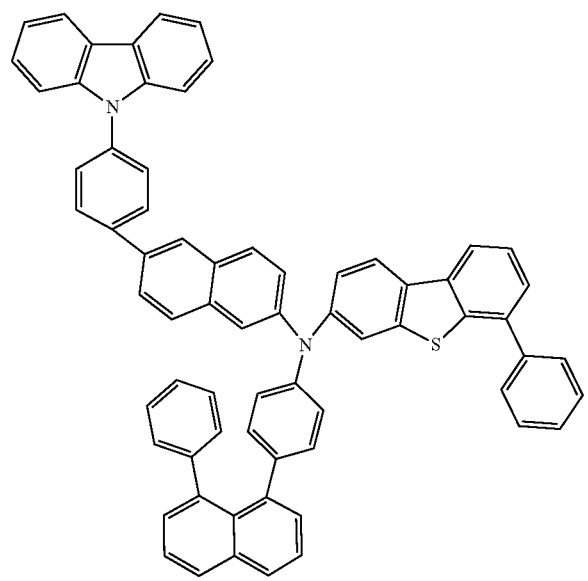
149
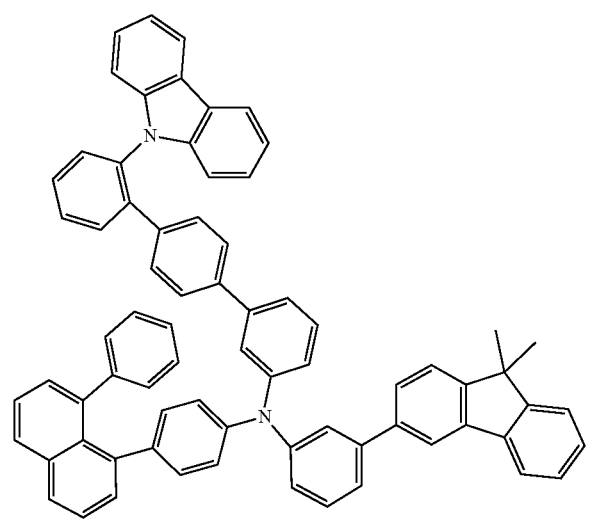

150
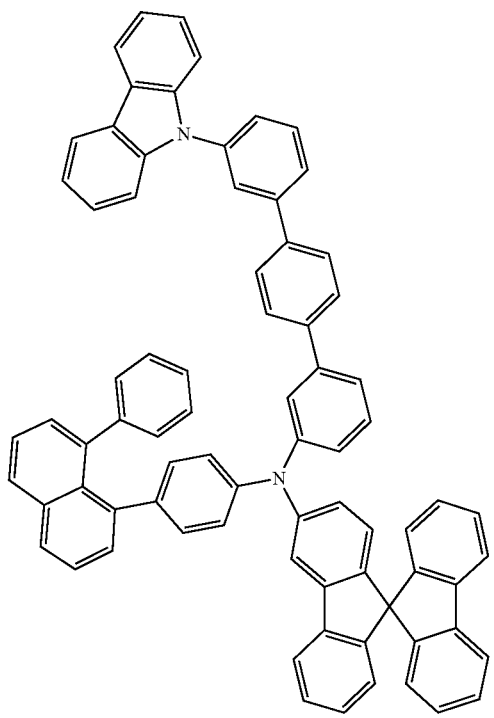
151
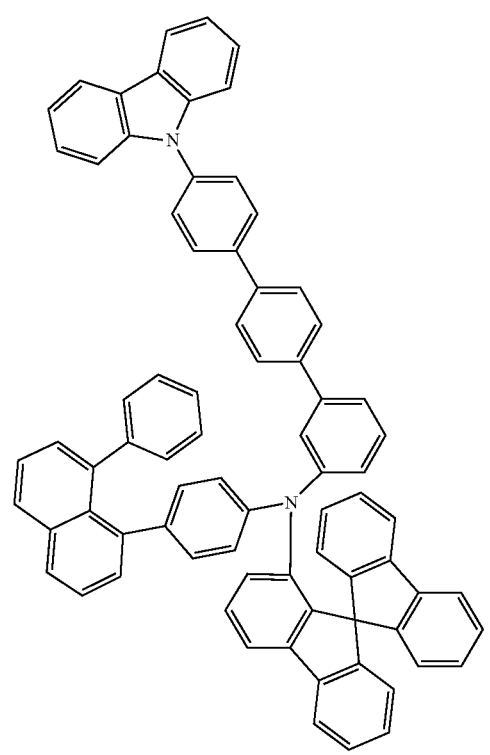
152
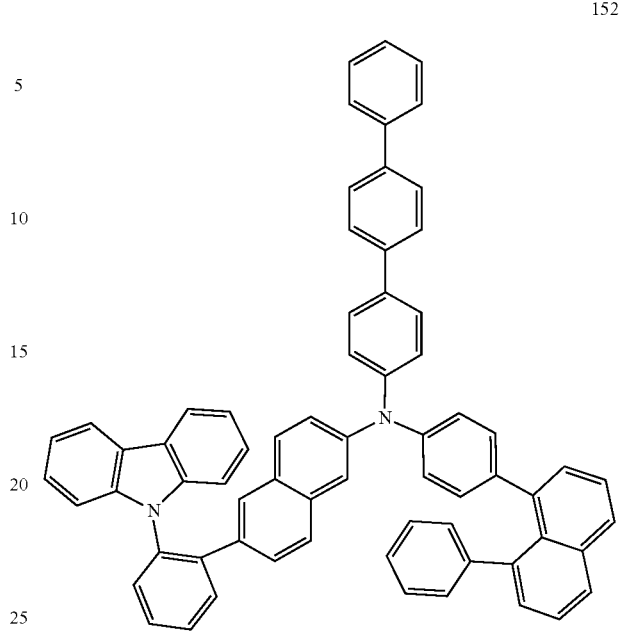
153
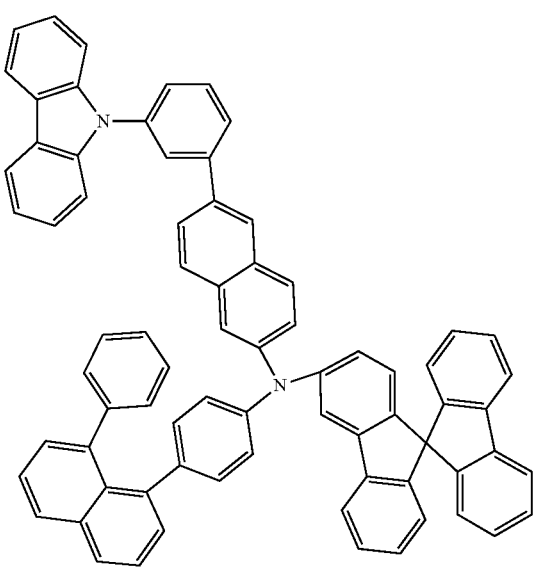

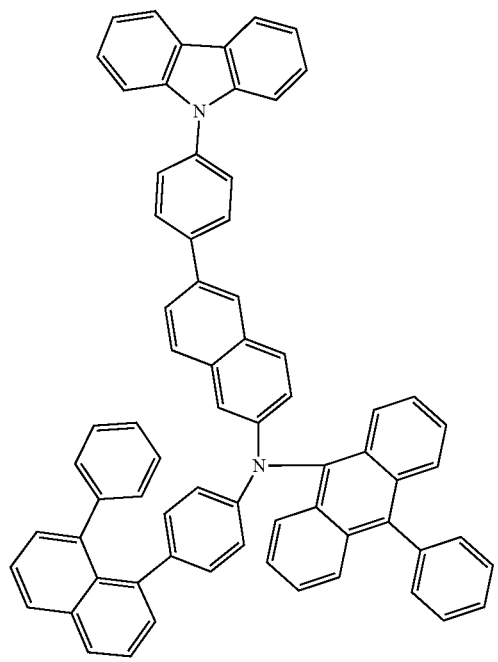
154
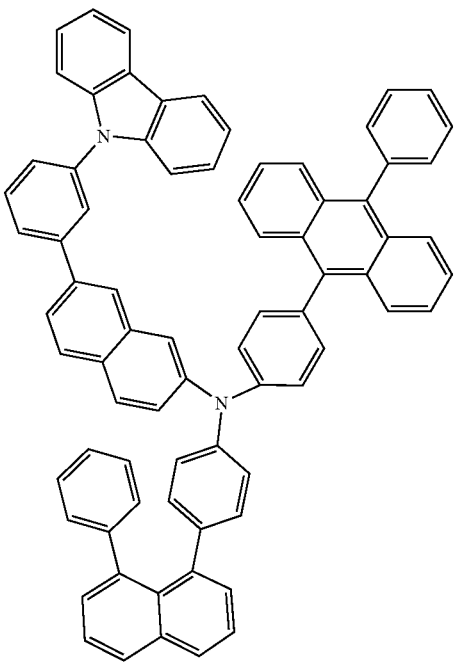
156
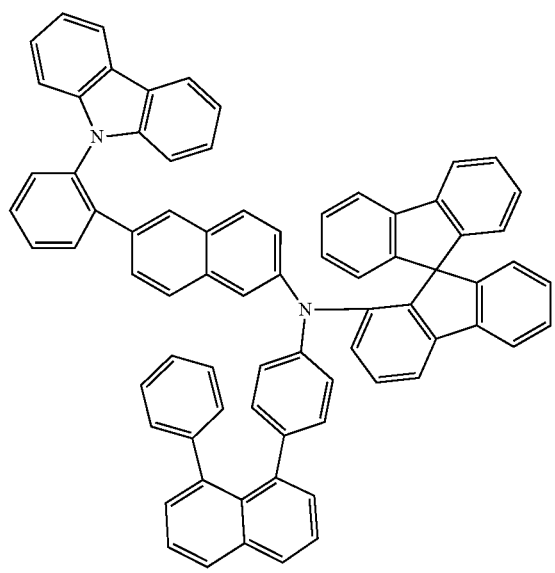
155
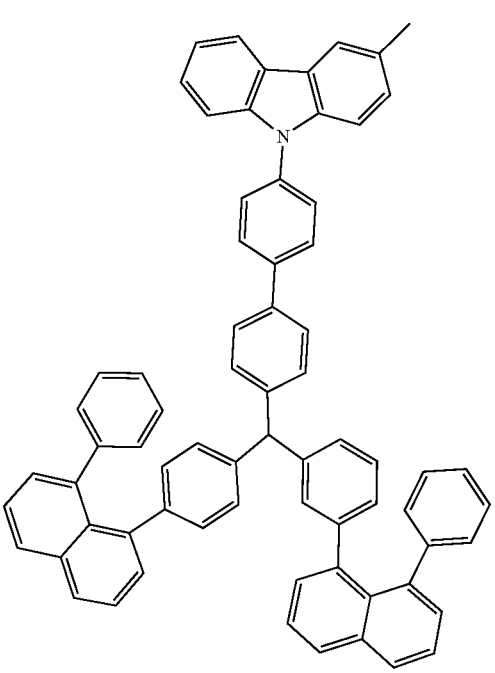
157

89
-continued
90
-continued
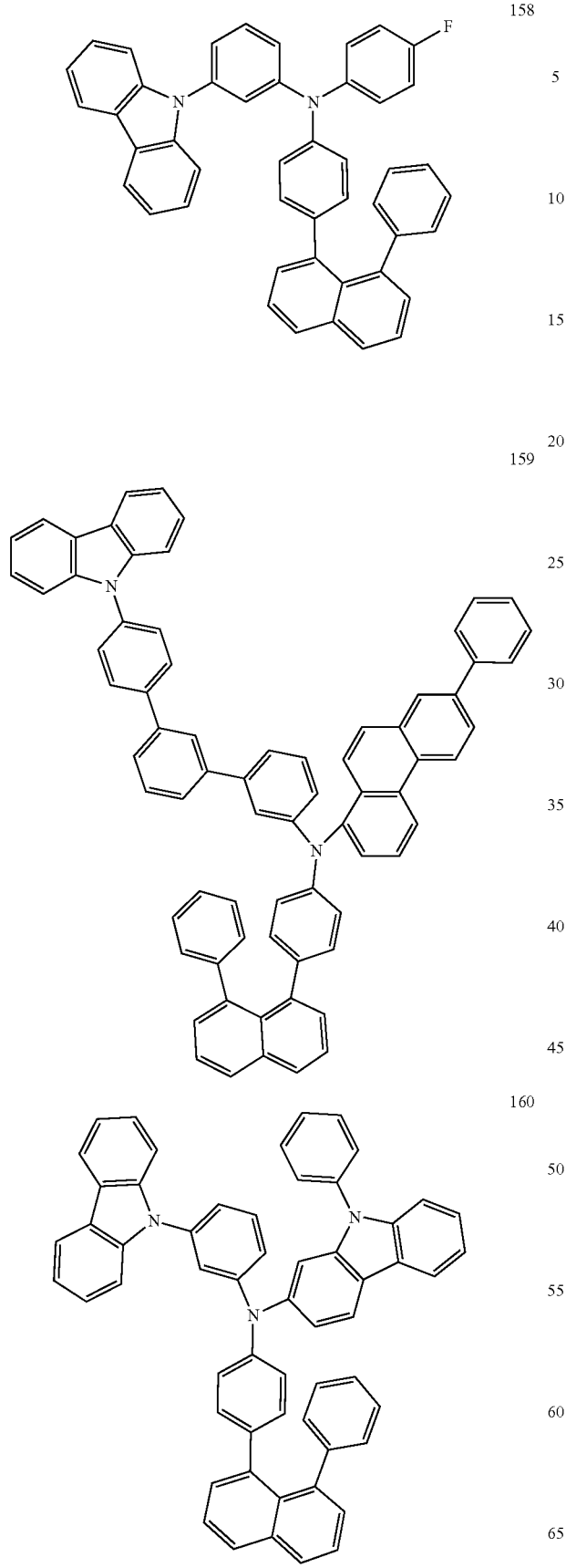
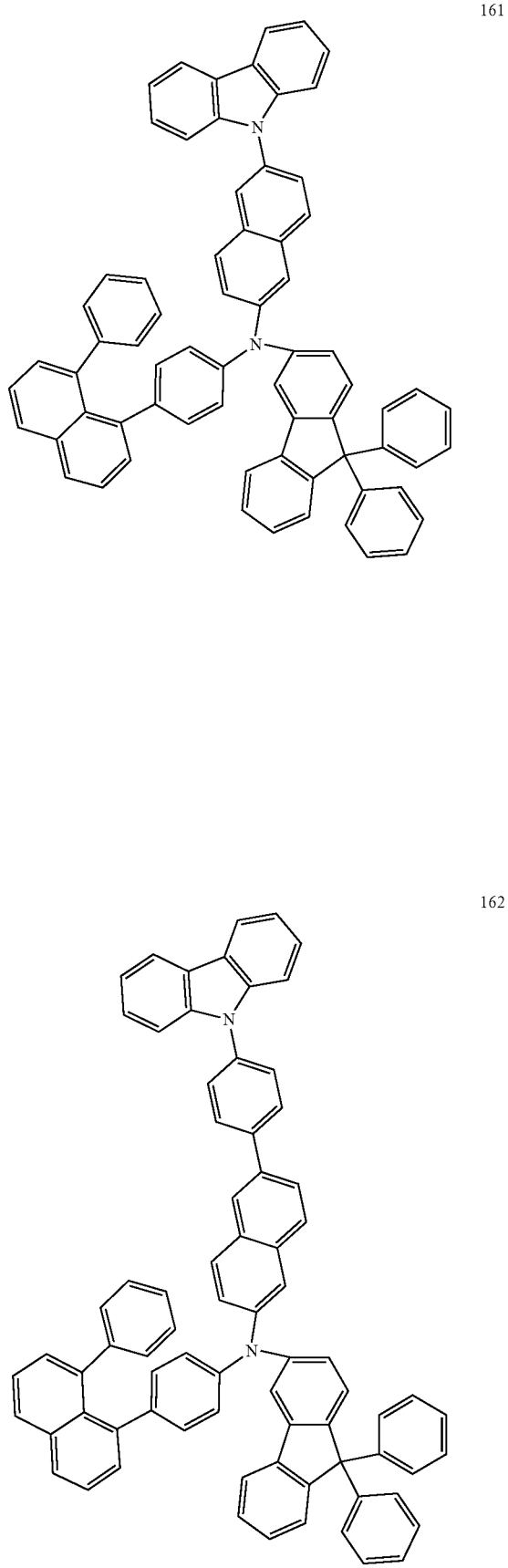

163
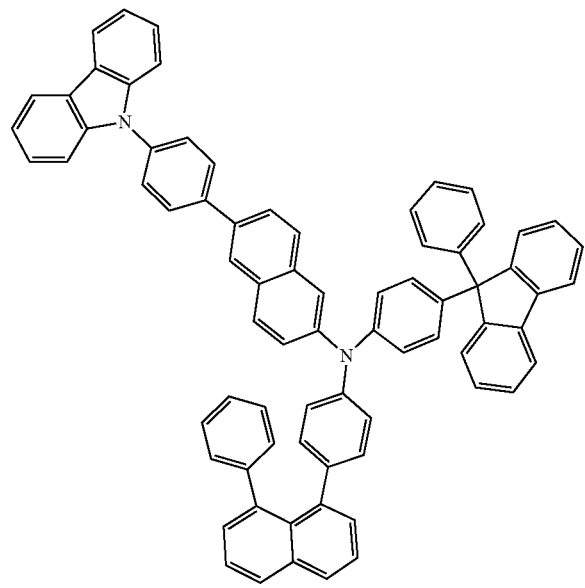
164
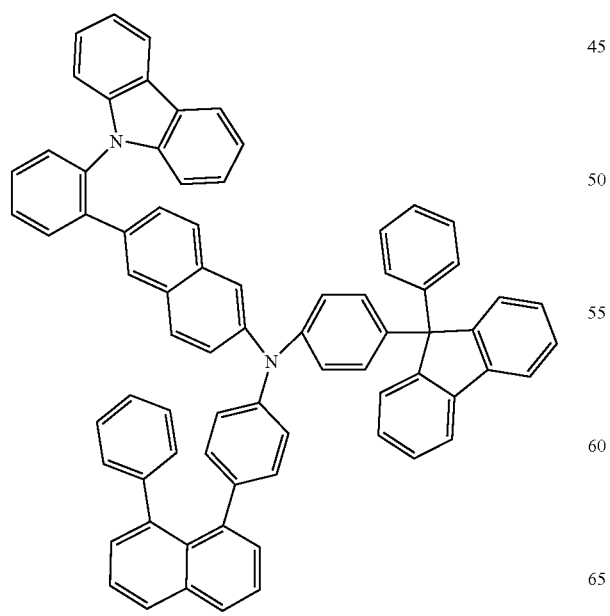
165
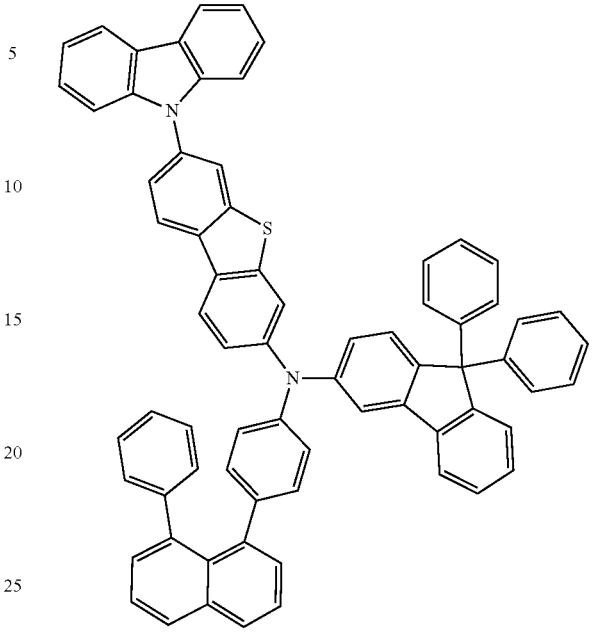
166
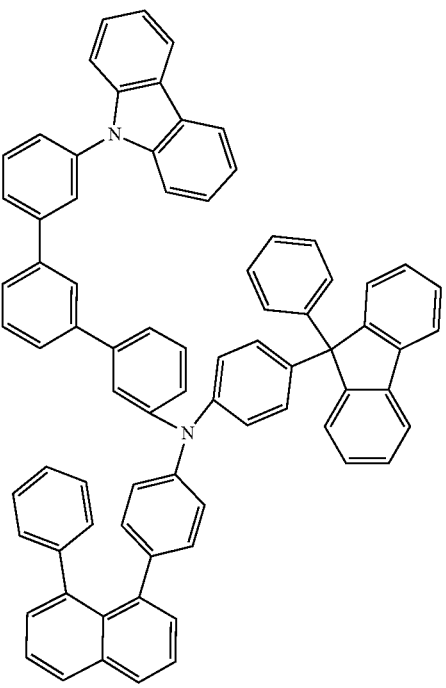

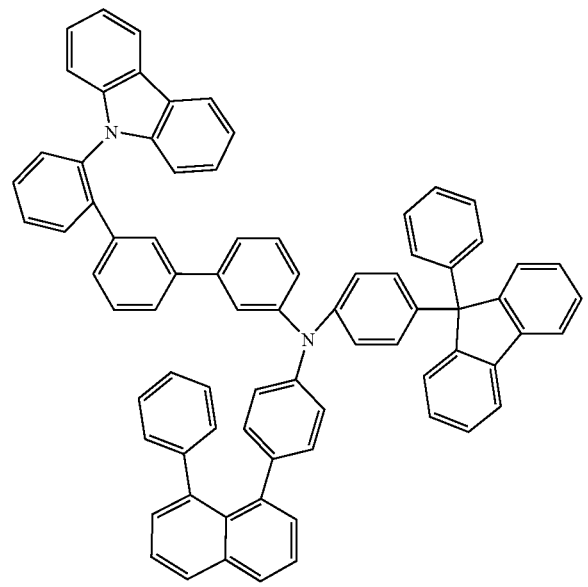
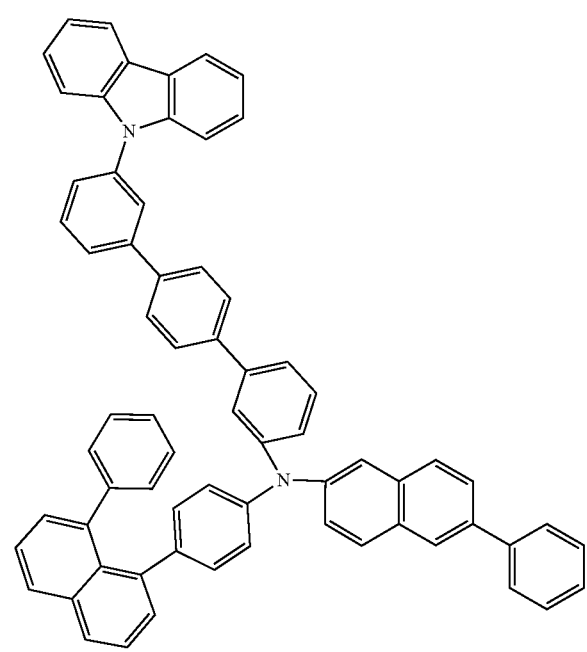
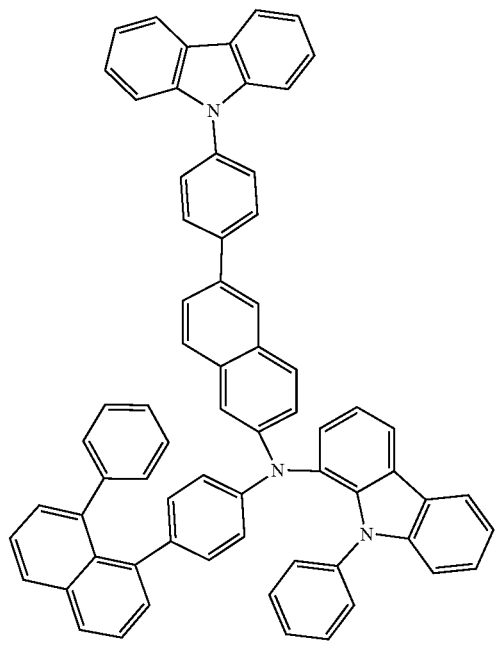
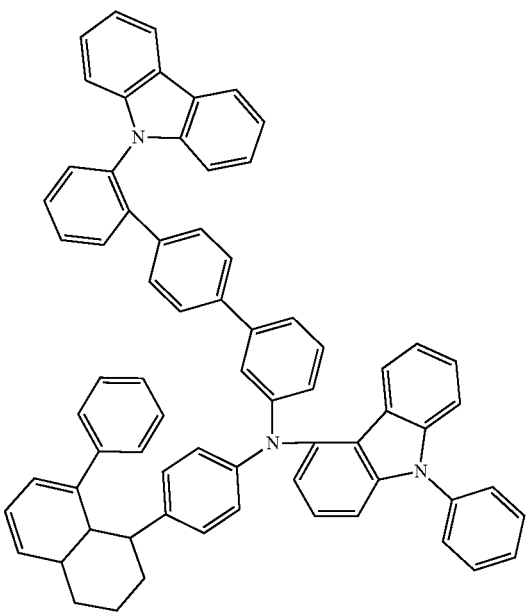

171
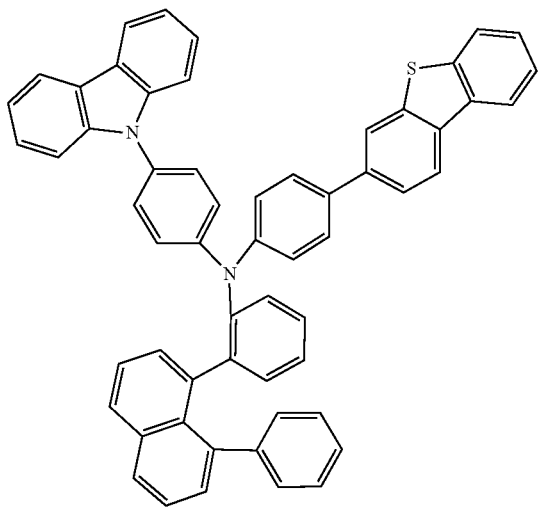
172
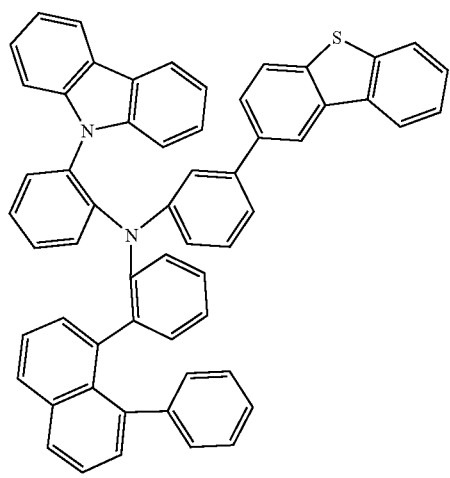
173
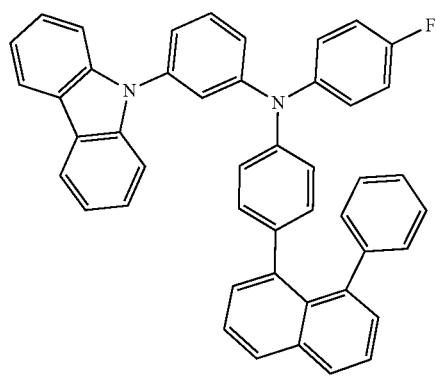
174
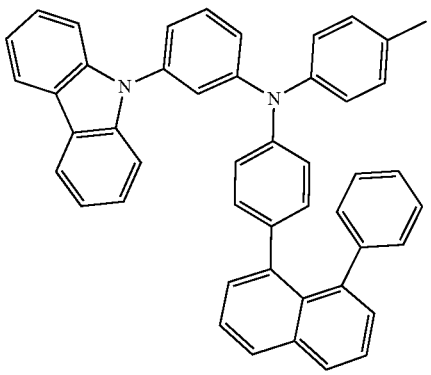
175
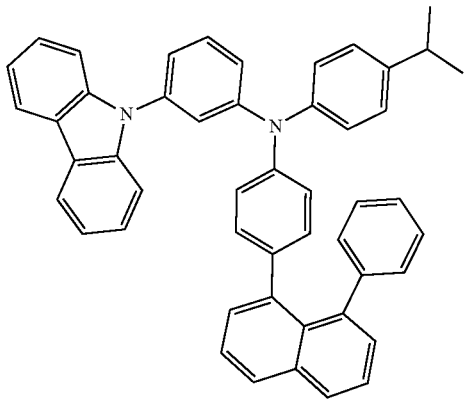
176
177
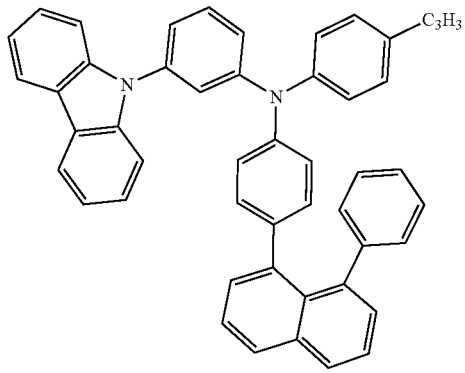

178
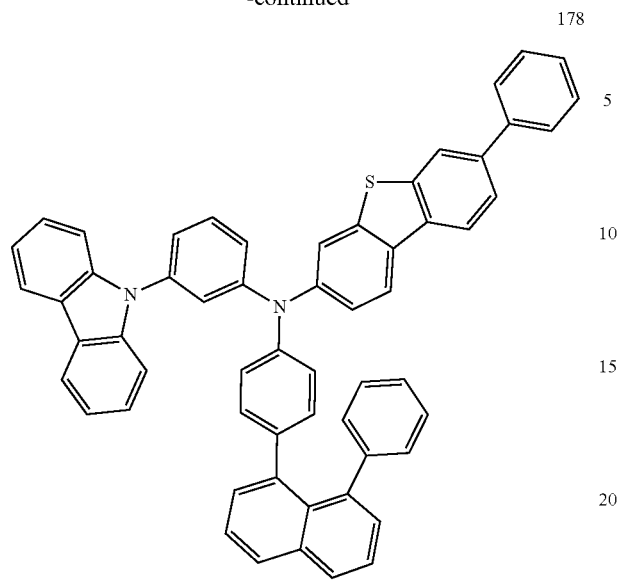
179
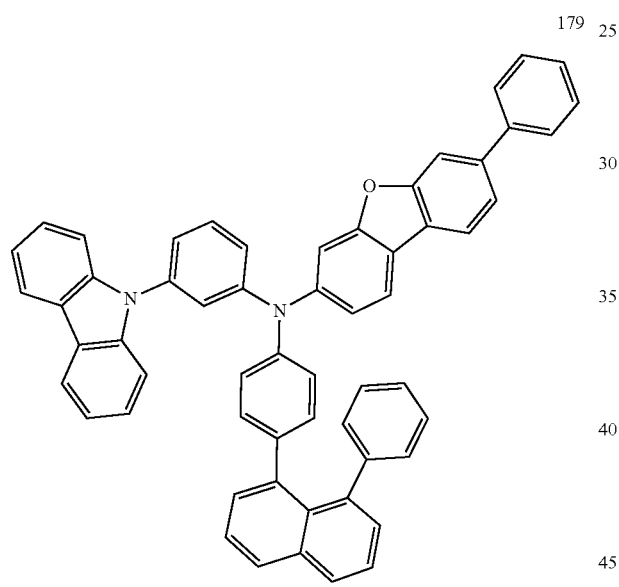
180
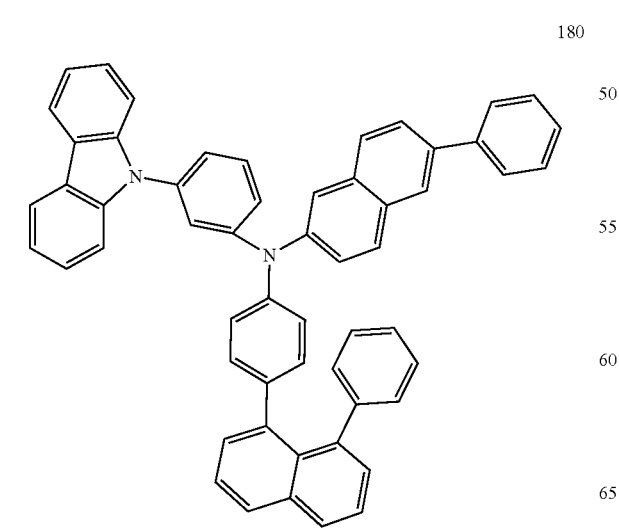
181
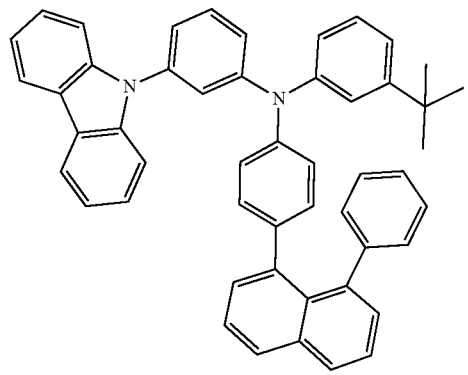
182
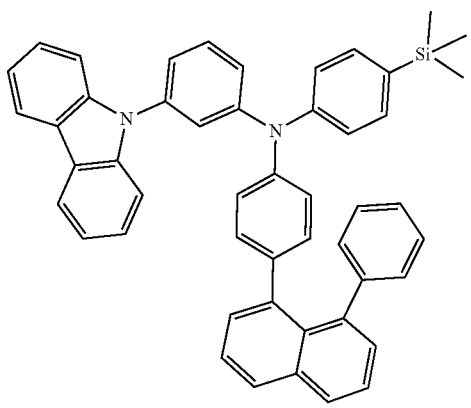
183
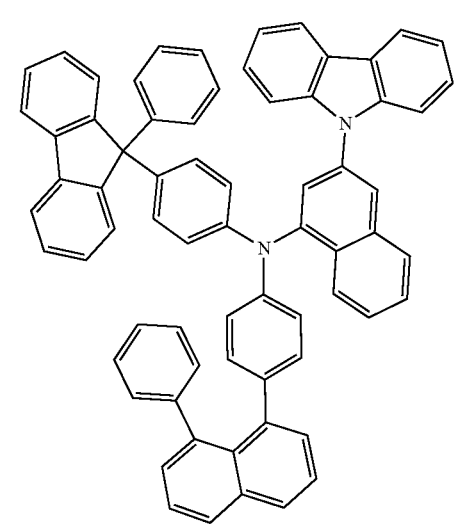

184
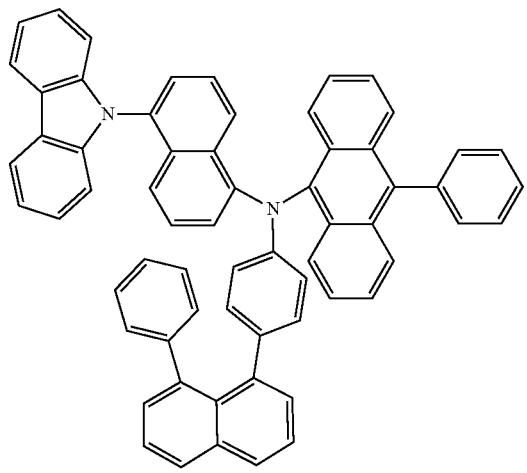
185
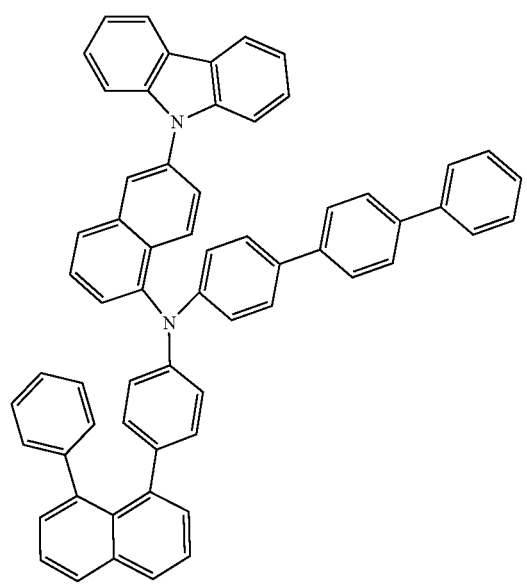
186
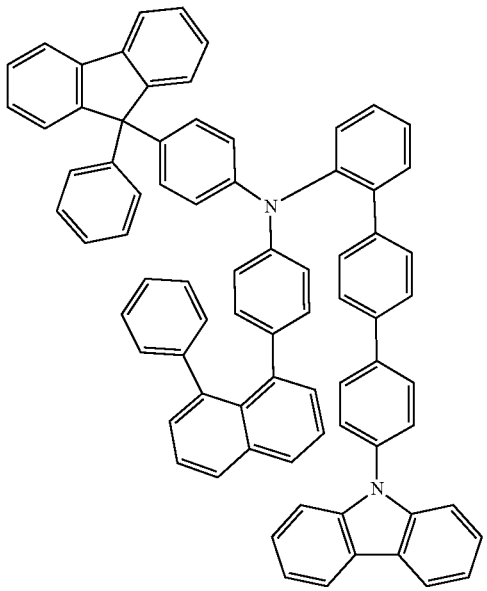
187
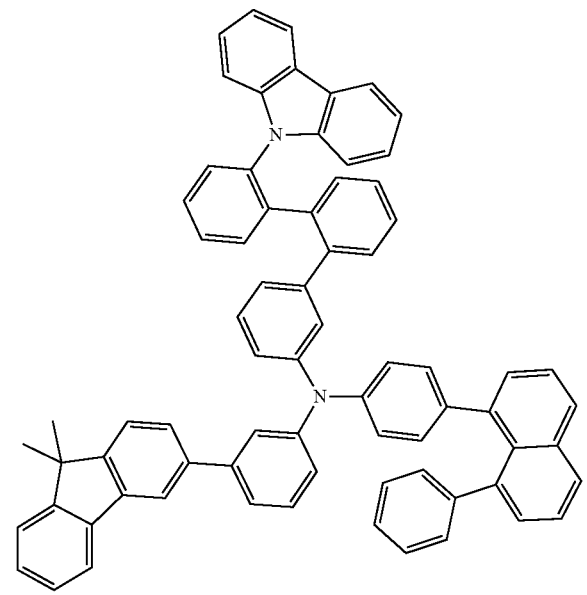

-continued
188
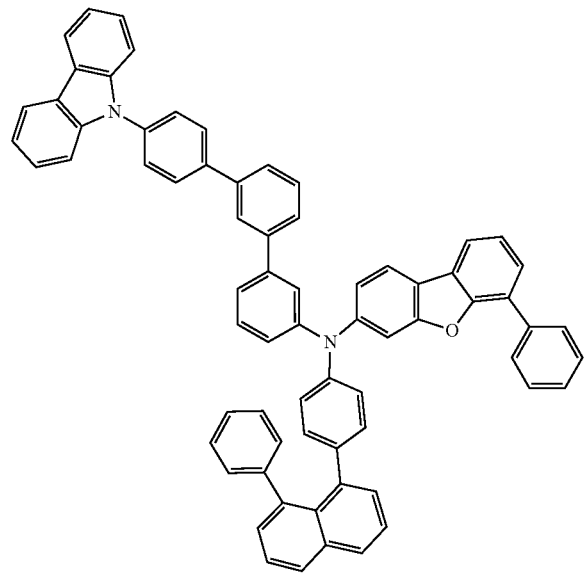
189
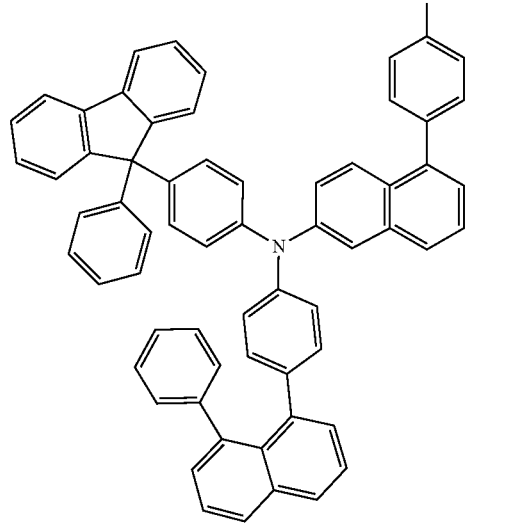
-continued
190
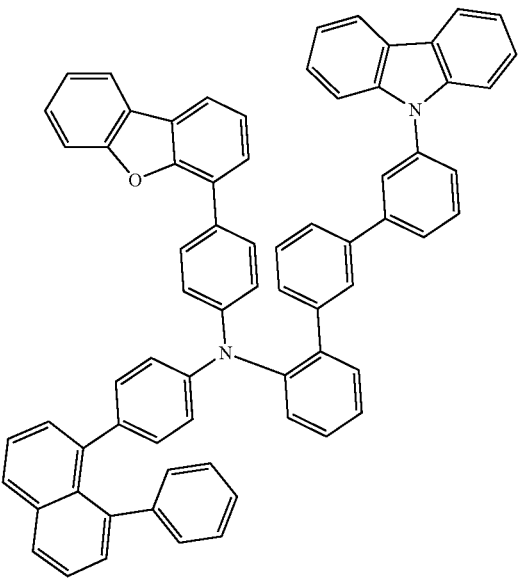
191
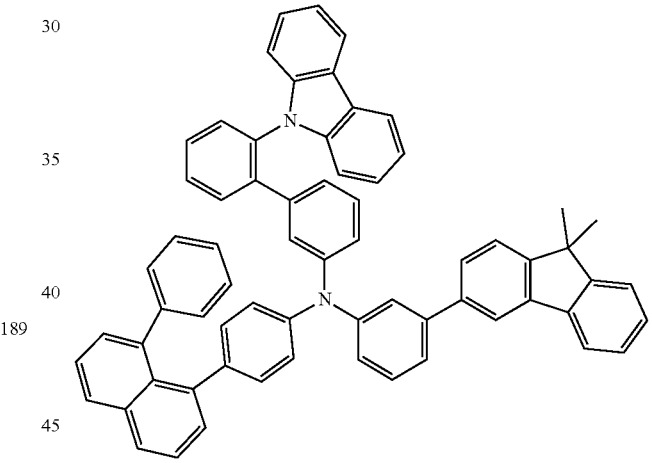
192
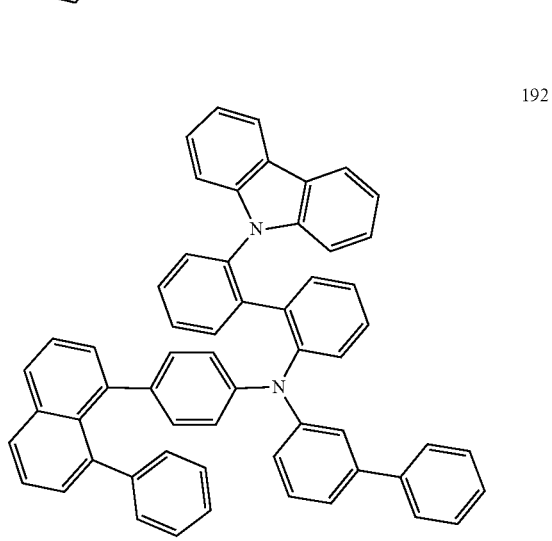

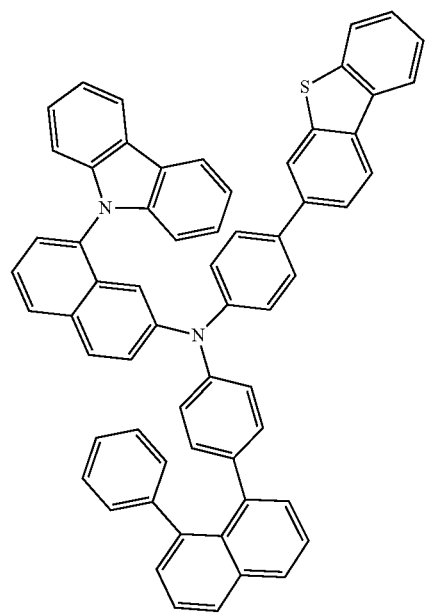
193
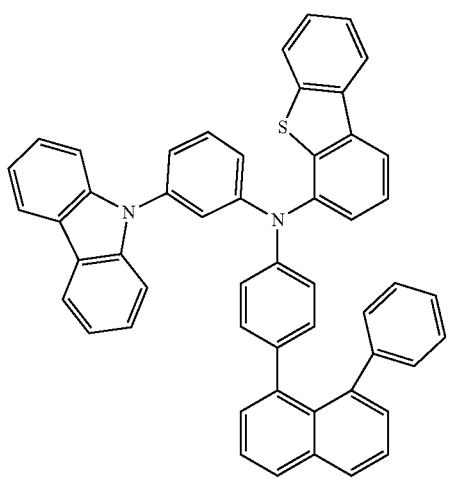
196
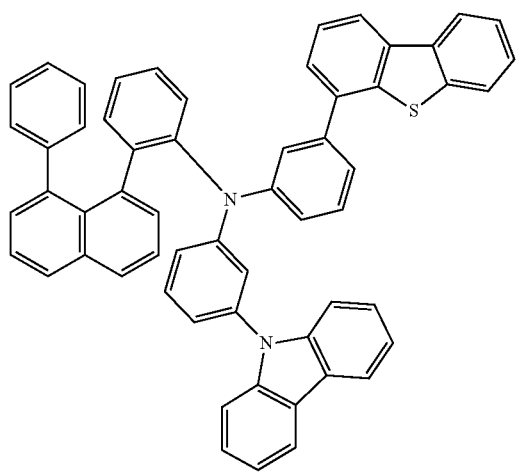
194
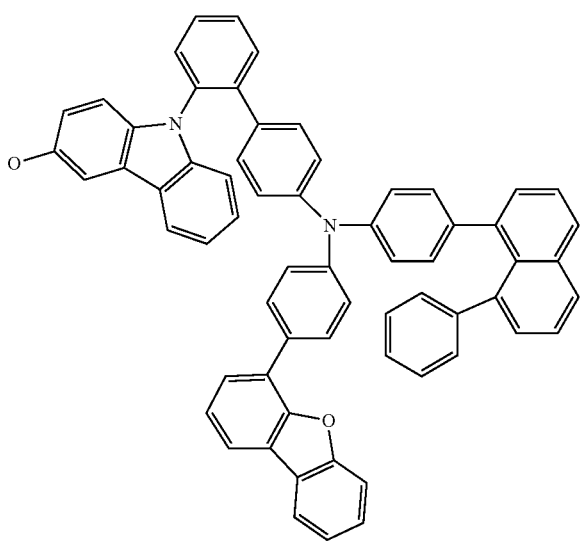
197
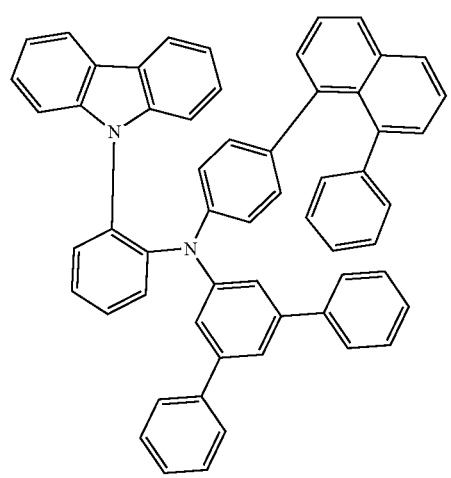
195
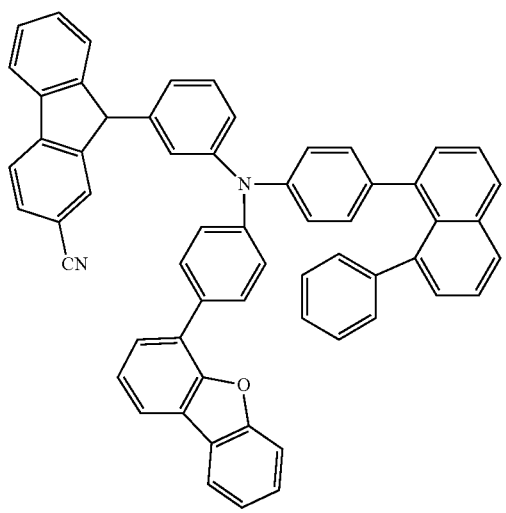
198

199
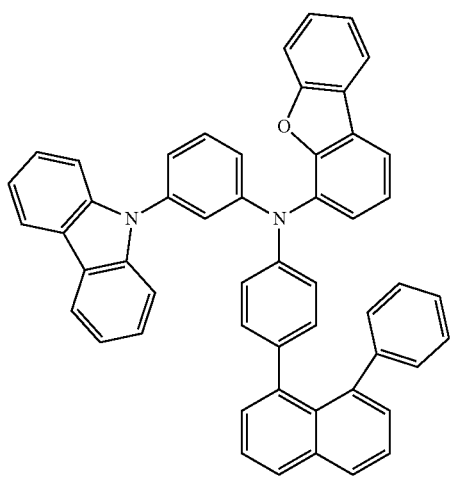
200
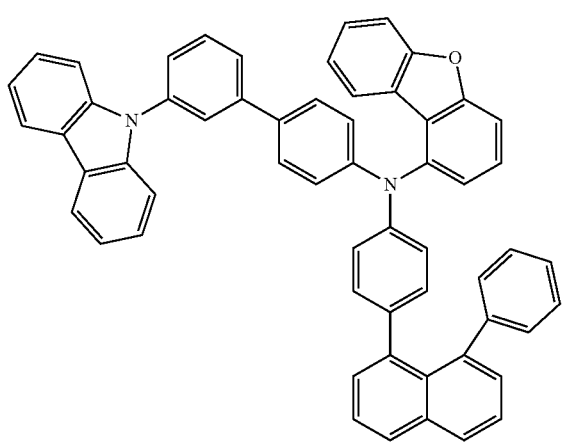
201
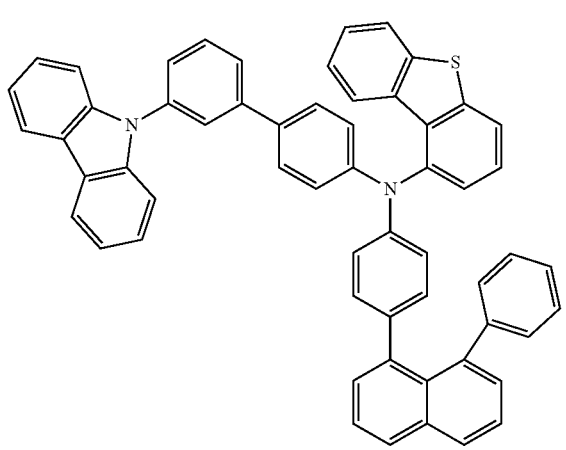
202
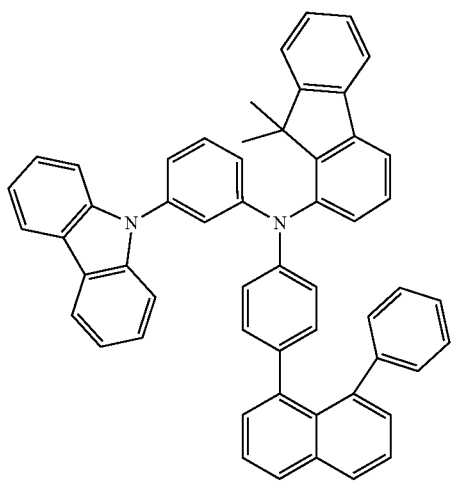
203
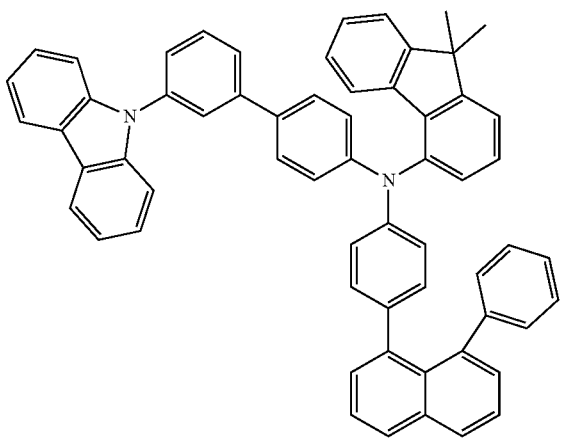
204
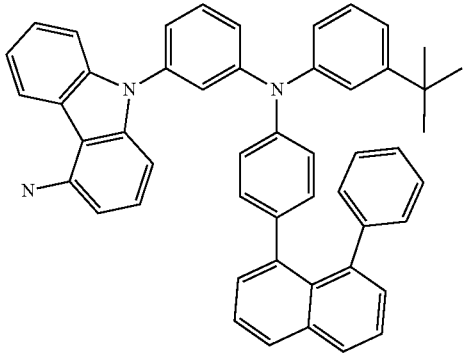

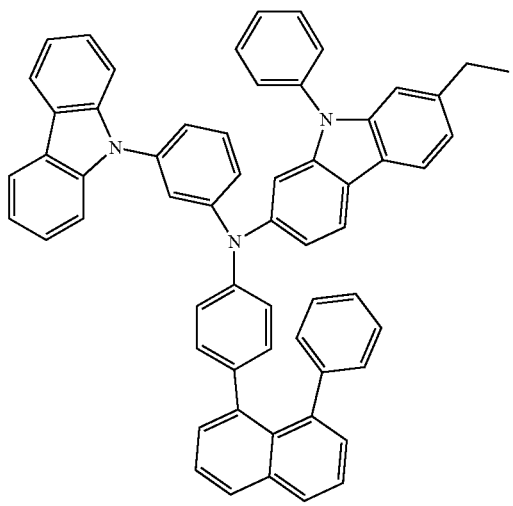

205

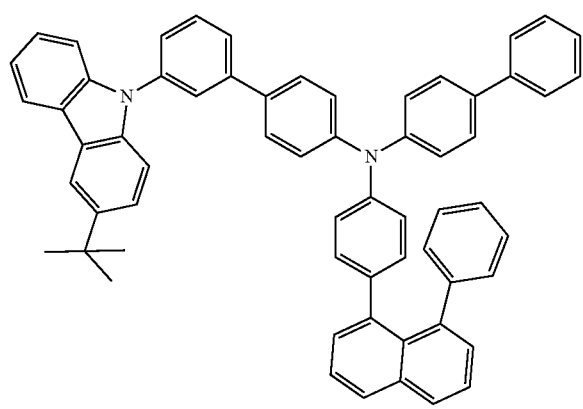

206

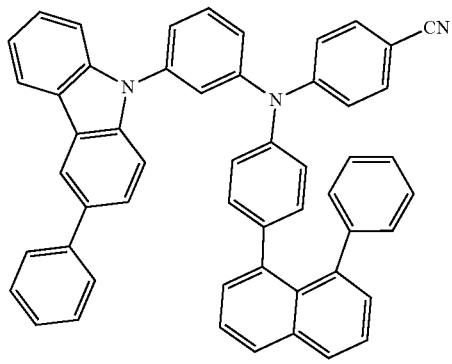

207

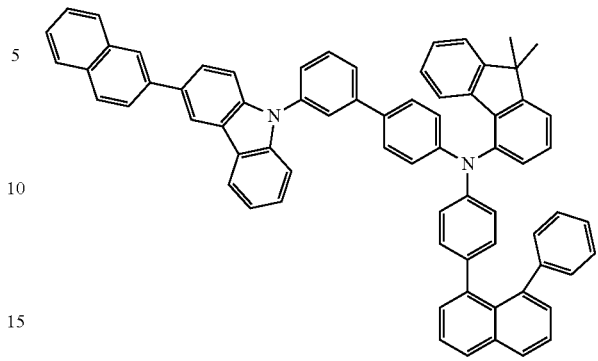

208

In the second aspect, the present application provides an electronic device, including: an anode and a cathode that are arranged oppositely, and a functional layer arranged between the anode and the cathode, wherein the functional layer includes the organic compound described above.

The organic compound provided in the present application can be used to form at least one organic film layer in the functional layer to improve the voltage, efficiency, and life span characteristics of the electronic device. Optionally, the organic film layer with the organic compound of the present application is arranged between the anode and the energy conversion layer of the electronic device, such as to improve the transport of electrons between the anode and the energy conversion layer. Further, the functional layer may include an HTL or EBL, and the HTL or EBL may include the organic compound described above.

The electronic device is an OLED.

As shown in FIG. 1, the OLED includes an anode 100 and a cathode 200 that are arranged oppositely, and a functional layer 300 arranged between the anode 100 and the cathode 200, wherein the functional layer 300 includes the organic compound provided in the present application.

Optionally, the anode 100 is preferably made of a material with a large work function that facilitates the injection of holes into the functional layer. Specific examples of the anode material may include, but are not limited to: metals such as nickel, platinum, vanadium, chromium, copper, zinc, and gold or alloys thereof; metal oxides such as zinc oxide, indium oxide, indium tin oxide (ITO), and indium zinc oxide (IZO); a recombination of a metal and an oxide such as ZnO:Al or $SnO_2$:Sb; or conductive polymers such as poly (3-methylthiophene), poly[3,4-(ethylene-1,2-dioxy)thiophene] (PEDT), polypyrrole (PPy), and polyaniline (PANI). Preferably, a transparent electrode with ITO is adopted as the anode.

Optionally, the cathode 200 is made of a material with a small work function that facilitates the injection of electrons into the functional layer. Specific examples of the cathode material may include, but are not limited to: metals such as magnesium, calcium, sodium, potassium, titanium, indium, yttrium, lithium, gadolinium, aluminum, argentum, tin, and lead or alloys thereof; or multi-layer materials such as LiF/Al, Liq/Al, $LiO_2$/Al, LiF/Ca, LiF/Al, and $BaF_2$/Ca. Preferably, a metal electrode with magnesium and argentum is adopted as the cathode.

As shown in FIG. 1, the functional layer 300 of the OLED includes an HTL 321, an EBL 322, an organic light-emitting layer 330, and an ETL 340 that are successively stacked. The organic light-emitting layer 330 is arranged at a side of the HTL 321 that is away from the anode 100. The ETL 340 is arranged at a side of the organic light-emitting layer 330 that is close to the cathode 200. The HTL 321 is arranged on a surface of the EBL 322 that is close to the anode 100.

Optionally, the HTL 321 may include the organic compound provided in the present application or another HTL material, and the another HTL material is selected from the group consisting of a carbazole polymer compound and a carbazole-linked triarylamine compound, which is not particularly limited in the present application. For example, the HTL 321 may include NPB.

Optionally, the EBL 322 may include one or more electron blocking materials, and the electron blocking materials is carbazole polymers or other compounds, which are not particularly limited in the present application. For example, the EBL 322 may include the organic compound of the present application.

Optionally, the organic light-emitting layer 330 is prepared from a single light-emitting material, or may include a host material and a guest material. Optionally, the organic light-emitting layer 330 may include a host material and a guest material, wherein holes and electrons injected into the organic light-emitting layer 330 can be recombined in the organic light-emitting layer 330 to form excitons, the excitons transfer energy to the host material, and then the host material transfers energy to the guest material, such that the guest material can emit light.

Optionally, the host material of the organic light-emitting layer 330 may include a metal chelate compound, a bistyryl derivative, an aromatic amine derivative, or a dibenzofuran derivative, which is not particularly limited in the present application. For example, the host material includes α,β-ADN.

Optionally, the guest material of the organic light-emitting layer 330 is a compound with a condensed aryl ring or a derivative thereof, a compound with a heteroaryl ring or a derivative thereof, an aromatic amine derivative, or the like, which is not particularly limited in the present application. For example, the guest material of the organic light-emitting layer 330 is BD-1.

Optionally, the ETL 340 may have a single-layer structure or a multi-layer structure, which may include one or more electron transport materials. The electron transport materials are benzimidazole derivatives, oxadiazole derivatives, quinoxaline derivatives, or other electron transport materials, which are not particularly limited in the present application. For example, the ETL 340 includes TPBi and LiQ.

Optionally, the functional layer 300 may further include an HIL 310, and the HIL 310 is arranged between the HTL 321 and the anode 100 to enhance the ability to inject holes into the HTL 321. The HIL 310 can be made of a benzidine derivative, a starburst arylamine compound, a phthalocyanine derivative, or another material, which is not particularly limited in the present application. For example, the HIL 310 includes HAT-CN.

Optionally, the functional layer 300 may further include an EIL 350, and the EIL 350 is arranged between the ETL 340 and the cathode 200 to enhance the ability to inject electrons into the ETL 340. The EIL 350 may include an inorganic material such as an alkali metal sulfide and an alkali metal halide, or may include a complex of an alkali metal and an organic substance. In an embodiment of the present application, the EIL 350 includes Yb.

In the third aspect, the present application provides an electronic apparatus, which includes the electronic device provided in the second aspect of the present application.

Figure 2:
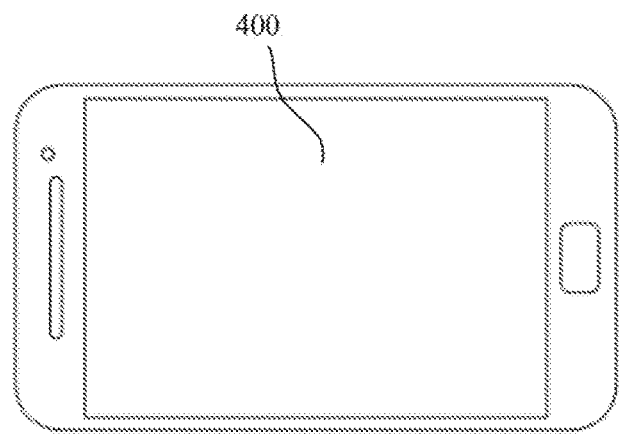
FIG. 2 is a schematic diagram of an electronic apparatus according to an embodiment of the present application.

For example, as shown in FIG. 2, the present application provides an electronic apparatus 400, and the electronic apparatus 400 includes the OLED. The electronic apparatus 400 is a display device, a lighting device, an optical communication device, or another electronic apparatus, including but not limited to computer screen, mobile phone screen, television set, electronic paper, emergency light, and optical module.

The present application will be described in detail below with reference to synthesis examples, but the following description is provided to explain the present application rather than limit the scope of the present application in any way.

SYNTHESIS EXAMPLES

1. Synthesis of an Intermediate 1A-X

Synthesis of IM 1A-1

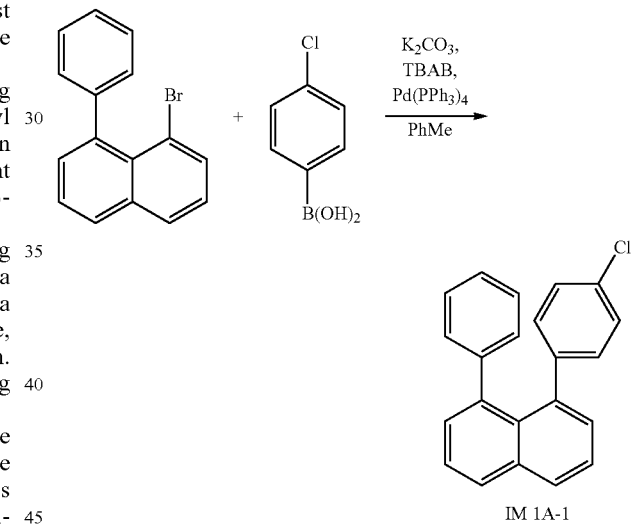

IM 1A-1

Under the protection of $N_2$, 1-bromo-8-phenylnaphthalene (25.00 g, 88.0 mmol), p-chlorophenylboronic acid (15.15 g, 96.89 mmol), potassium carbonate (24.40 g, 177.0 mmol), tetrabutylammonium bromide (TBAB) (0.29 g, 0.90 mmol), and tetrakis(triphenylphosphine) palladium (0.51 g, 0.5 mmol) were added to a three-necked flask, then toluene (150 mL), ethanol (40 mL), and water (20 mL) were added, and a resulting mixture was heated to reflux for 8 h; a resulting reaction system was cooled to room temperature, washed with water, dried with magnesium sulfate, and filtered, and a filtrate was concentrated in a vacuo for solvent removal to obtain a crude product; and the crude product was purified by recrystallization with toluene to obtain a white solid IM 1A-1 (17 g, yield: 61%).

IM 1A-X in table 1 was synthesized with reference to the synthesis method of the IM 1A-1, except that a raw material 1 was used instead of p-chlorophenylboronic acid. The main raw materials used and the synthesized intermediates and yields thereof were shown in Table 1.

TABLE 1

| Raw material 1 | IM 1A-X | Yield/% |
|---|---|---|
| (structure with B(OH)₂ and Cl) | IM 1A-2 | 60 |
| (structure with B(OH)₂ and Cl) | IM 1A-3 | 59 |

2. Synthesis of an Intermediate IM a-X

Synthesis of IM a-147

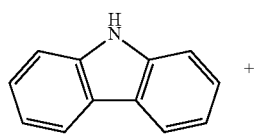
+
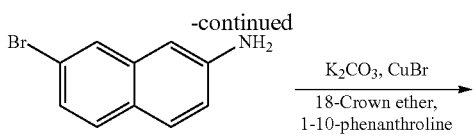

-continued

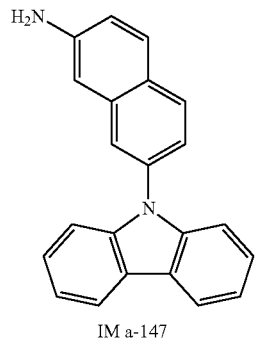

IM a-147

Under the protection of N₂, carbazole (30.00 g, 179.42 mmol), 7-bromo-binaphthyl-2-amine (43.83 g, 197.36 mmol), potassium carbonate (61.99 g, 448.53 mmol), cuprous bromide (1.28 g, 8.97 mmol), 18-crown ether (2.37 g, 8.97 mmol), 1-10-phenanthroline (3.23 g, 17.94 mmol), and toluene (250 mL) were added to a three-necked flask, a resulting mixture was mechanically stirred and heated to reflux, then a reaction degree was detected by thin-layer chromatography (TLC), and cuprous bromide was supplemented; 80 h later, the reaction was stopped, and a resulting reaction system was cooled to room temperature, washed with water, dried with magnesium sulfate, and filtered; and a filtrate was concentrated in a vacuo for solvent removal to obtain a crude product, and the crude product was purified by recrystallization with a toluene system to obtain a white solid IM a-147 (11.1 g, yield: 20%).

IM a-X in table 2 was synthesized with reference to the synthesis method of the IM a-147, except that a raw material 2 was used instead of carbazole and a raw material 3 was used instead of the 7-bromo-binaphthyl-2-amine. The main raw materials used and the synthesized intermediates and yields thereof were shown in Table 2.

TABLE 2

| Raw material 2 | Raw material 3 | IM a-X | Yield/% |
|---|---|---|---|
| (carbazole structure) | (bromo-dimethylfluorene-amine structure) | IM a-117 | 20 |

TABLE 2-continued
| Raw material 2 | Raw material 3 | IM a-X | Yield/% |
|---|---|---|---|
| | 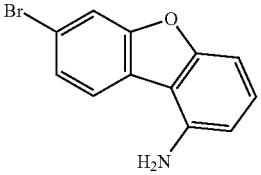 [SMILES: Nc1cccc2oc3cc(Br)ccc3c12] | 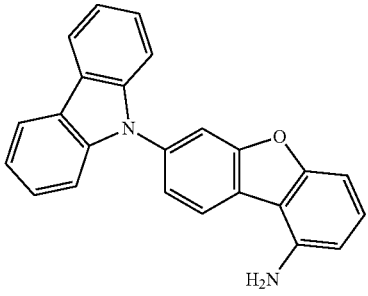 [SMILES: Nc1cccc2oc3cc(-n4c5ccccc5c5ccccc54)ccc3c12]
IM a-134 | 21 |
| | 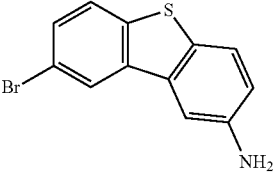 [SMILES: Nc1ccc2sc3ccc(Br)cc3c2c1] | 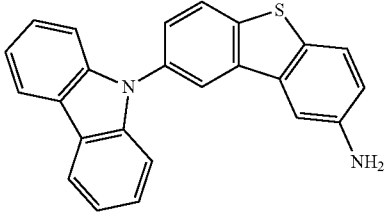 [SMILES: Nc1ccc2sc3ccc(-n4c5ccccc5c5ccccc54)cc3c2c1]
IM a-143 | 23 |
| 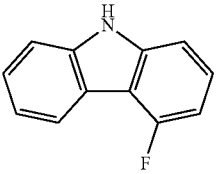 [SMILES: Fc1cccc2[nH]c3ccccc3c12] | 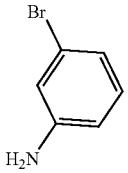 | 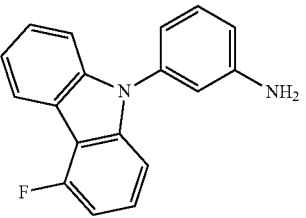 [SMILES: Nc1cccc(-n2c3ccccc3c3c(F)cccc32)c1]
IM a-198 | 20 |
| 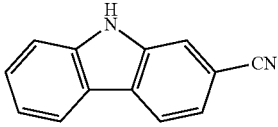 | | 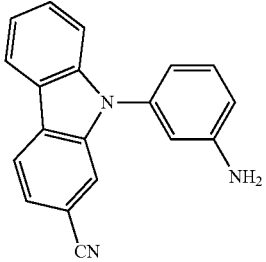 [SMILES: N#Cc1ccc2c3ccccc3n(-c3cccc(N)c3)c2c1]
IM a-204 | 21 |

3. Synthesis of an Intermediate IM 2A-X

Synthesis of IM 2A-1

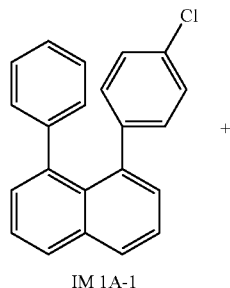

IM 1A-1

+

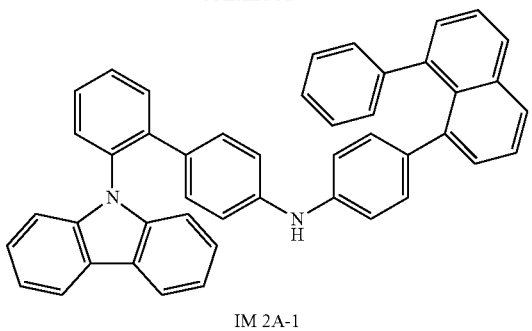

IM 2A-1

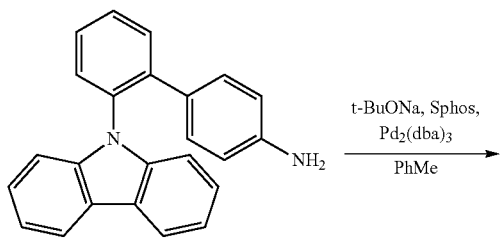

t-BuONa, Sphos, Pd₂(dba)₃ / PhMe →

Under the protection of $N_2$, the IM 1A-1 (15.00 g, 47.65 mmol), 1,1'-biphenyl-4-amine (17.53 g, 52.41 mmol), and toluene (150 mL) were added to a three-necked flask, and a resulting mixture was stirred and heated to reflux for 30 min and then cooled to 70° C. to 80° C.; sodium tert-butoxide (6.86 g, 71.47 mmol), 2-dicyclohexylphosphino-2',6'-dimethoxybiphenyl (0.39 g, 0.95 mmol), and tris(dibenzylideneacetone) dipalladium (0.44 g, 0.48 mmol) were added, and after a stable reaction system was obtained, the reaction system was heated to reflux and stirred for 2 h, then cooled to room temperature, washed with water, dried with magnesium sulfate, and filtered; and a filtrate was concentrated in a vacuo for solvent removal to obtain a crude product, and the crude product was purified by recrystallization with a toluene system to obtain a white solid IM 2A-1 (23.35 g, yield: 80%).

IM 2A-X in table 3 was synthesized with reference to the synthesis method of the IM 2A-1, except that IM 1A-X was used instead of the IM 1A-1 and a raw material 4 was used instead of the 1,1'-biphenyl-4-amine. The main raw materials used and the synthesized intermediates and yields thereof were shown in Table 3.

TABLE 3

| IM 1A-X | Raw material 4 | IM 2A-X | Yield/% |
|---|---|---|---|
| IM 1A-3 | | IM 2A-3 | 81 |
| | | IM 2A-4 | 84 |
| | | IM 2A-5 | 80 |

TABLE 3-continued
| IM 1A-X | Raw material 4 | IM 2A-X | Yield/% |
|---|---|---|---|
| | 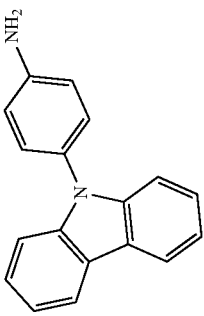 | 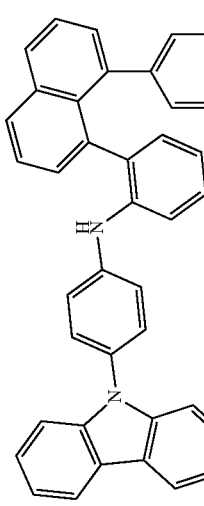 IM 2A-X | 75 |
| 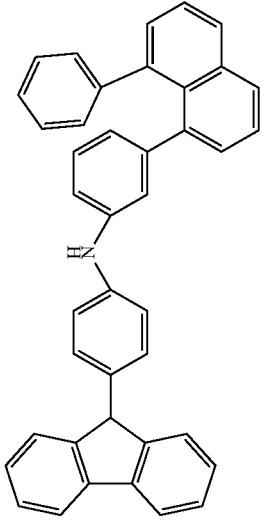 IM 1A-2 | 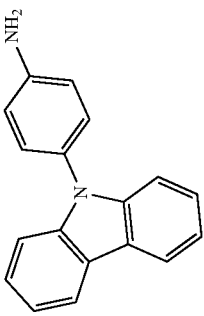 | 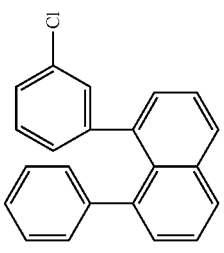 IM 2A-6 | 75 |
| 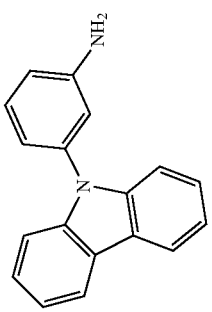 IM 1A-1 | 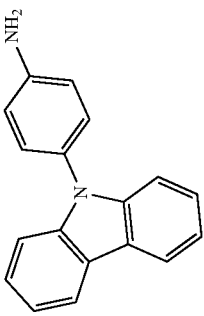 | 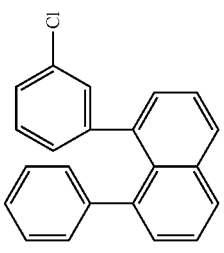 IM 2A-7 | 80 |
| | | 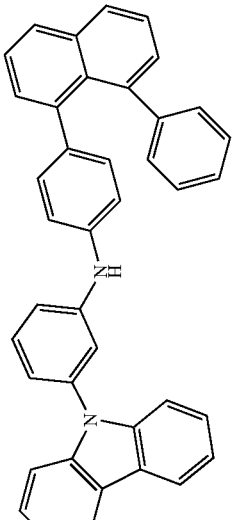 IM 2A-2 | |

TABLE 3-continued

| IM 1A-X | Raw material 4 | IM 2A-X | Yield/% |
|---|---|---|---|
| IM a-117 | | IM 2A-8 | 76 |
| IM a-134 | | IM 2A-9 | 72 |
| IM a-143 | | IM 2A-10 | 73 |

TABLE 3-continued

| IM 1A-X | Raw material 4 | IM 2A-X | Yield/% |
|---|---|---|---|
| | IM a-147 | IM 2A-11 | 74 |
| | | IM 2A-12 | 73 |
| | | IM 2A-13 | 75 |

TABLE 3-continued
| IM 1A-X | Raw material 4 | IM 2A-X | Yield/% |
|---|---|---|---|
| 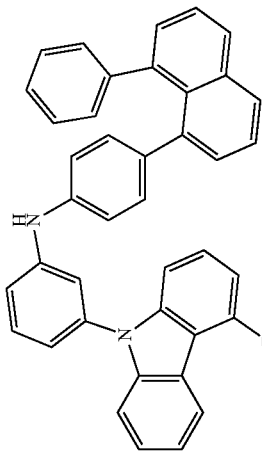 | 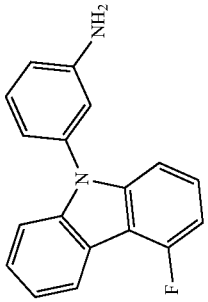 | 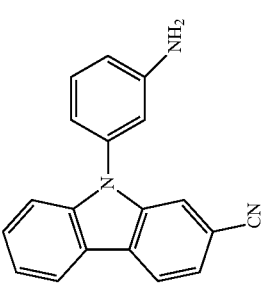 IM 2A-14 | 67 |
| | | 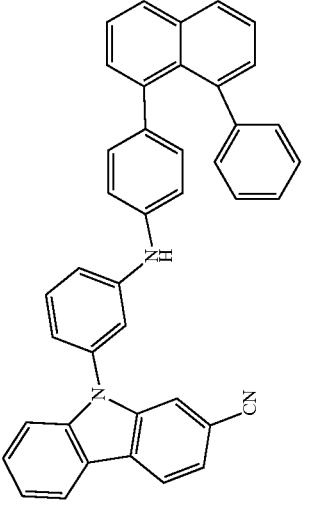 IM 2A-15 | 69 |

4. Synthesis of Compounds

Synthesis of a Compound 1

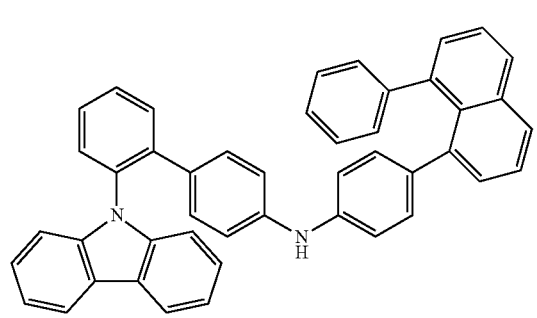

IM 2A-1

+

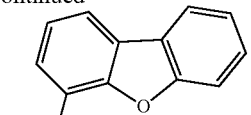

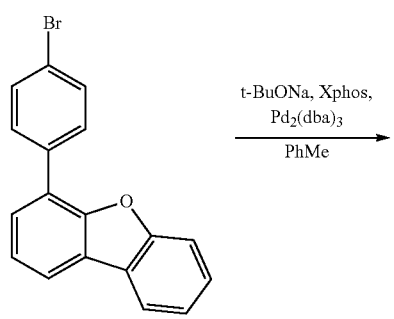

t-BuONa, Xphos,
Pd₂(dba)₃
⟶
PhMe

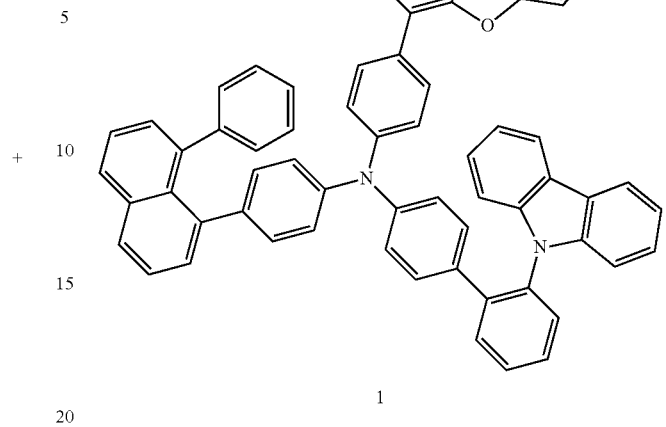

1

Under the protection of N₂, the IM 2A-1 (15.0 g, 24.50 mmol), 4-(4-bromophenyl)-dibenzofuran (7.92 g, 24.50 mmol), and toluene (150 mL) were added to a three-necked flask, and a resulting mixture was stirred and heated to reflux for 30 min and then cooled to 70° C. to 80° C.; sodium tert-butoxide (3.53 g, 36.75 mmol), 2-dicyclohexylphosphino-2,4,6-triisopropylbiphenyl (0.20 g, 0.49 mmol), and tris(dibenzylideneacetone) dipalladium (0.22 g, 0.25 mmol) were added, and after a stable reaction system was obtained, the reaction system was heated to reflux and stirred for 2 h, then cooled to room temperature, washed with water, dried with magnesium sulfate, and filtered; and a filtrate was concentrated in a vacuo for solvent removal to obtain a crude product, and the crude product was purified by recrystallization with a toluene system to obtain a white solid compound 1 (14.65 g, yield: 70%, MS: (m/z)=855.33 [M+H]⁺).

The compounds listed in Table 4 were each synthesized with reference to the synthesis method of the compound 1, except that IM 2A-X was used instead of the IM 2A-1 and a raw material 5 was used instead of the 4-(4-bromophenyl)-dibenzofuran. The main raw materials used and the structures and yields of the synthesized compounds were shown in Table 4.

TABLE 4
| IM 2A-X | Raw material 5 | Compound | Yield/% | MS (m/z) [M + H]+ |
|---|---|---|---|---|
| 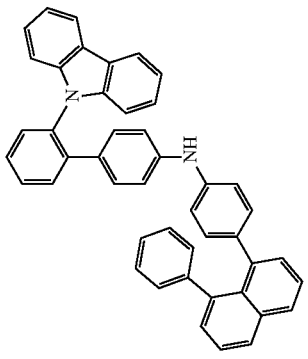 IM 2A-1 | 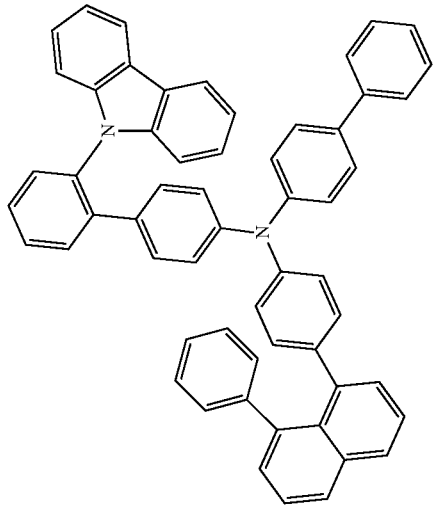 | 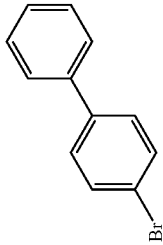 22 | 71 | 765.32 |
| 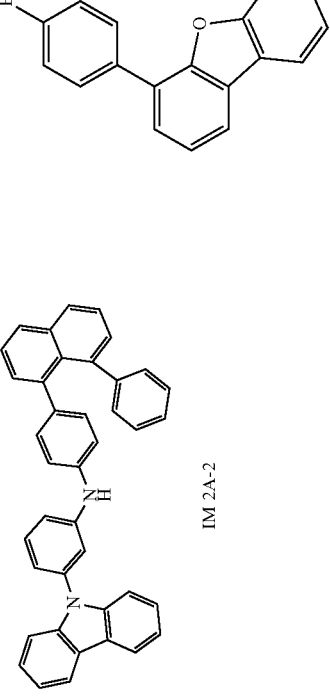 IM 2A-2 | | 2 | 70 | 779.30 |

TABLE 4-continued
| IM 2A-X | Raw material 5 | Compound | Yield/% | MS (m/z) [M + H]+ |
|---|---|---|---|---|
| | 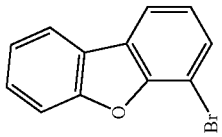 | 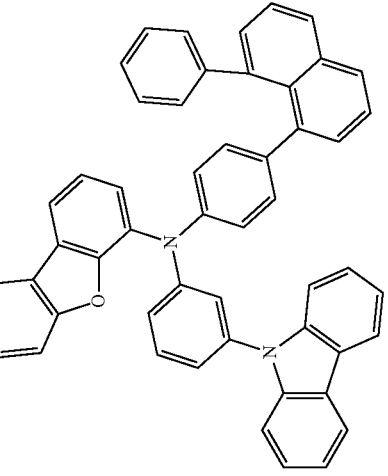 199 | 70 | 703.27 |
| | 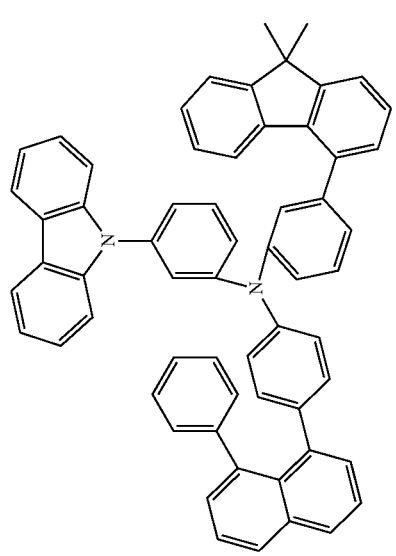 | 46 | 72 | 806.04 |

TABLE 4-continued

| IM 2A-X | Raw material 5 | Compound | Yield/% | MS (m/z)/ [M + H]+ |
|---|---|---|---|---|
| | Br-C6D5 (bromobenzene-d5) | 76 | 72 | 618.29 |
| | 4-bromofluorobenzene | 173 | 68 | 631.25 |

TABLE 4-continued
| IM 2A-X | Raw material 5 | Compound | Yield/% | MS (m/z) [M + H]+ |
|---|---|---|---|---|
| | 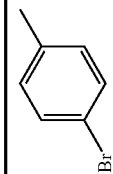 | 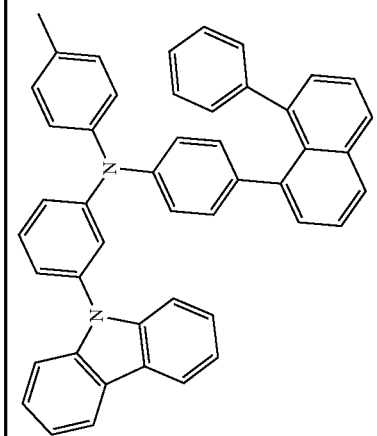 174 | 65 | 627.27 |
| | 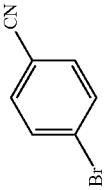 | 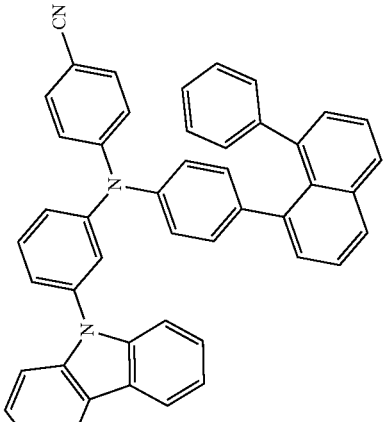 175 | 67 | 638.26 |

TABLE 4-continued
| Raw material 5 | Compound | Yield/% | MS (m/z)/ [M + H]+ |
|---|---|---|---|
| 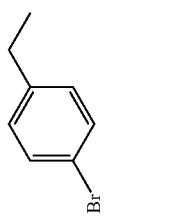 | 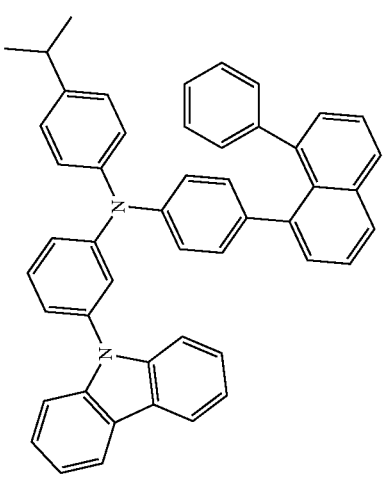<br>176 | 64 | 655.30 |
|  | 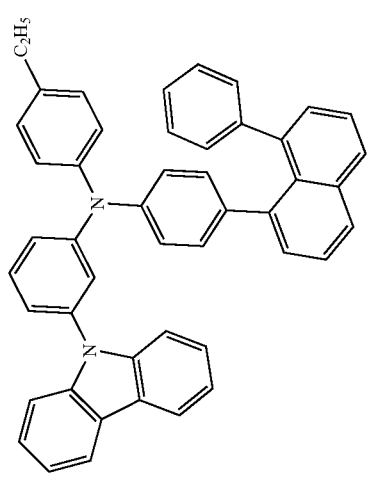<br>177 | 71 | 641.29 |
IM 2A-X TABLE 4-continued
| IM 2A-X | Raw material 5 | Compound | Yield/% | MS (m/z)/ [M + H]+ |
|---|---|---|---|---|
| | 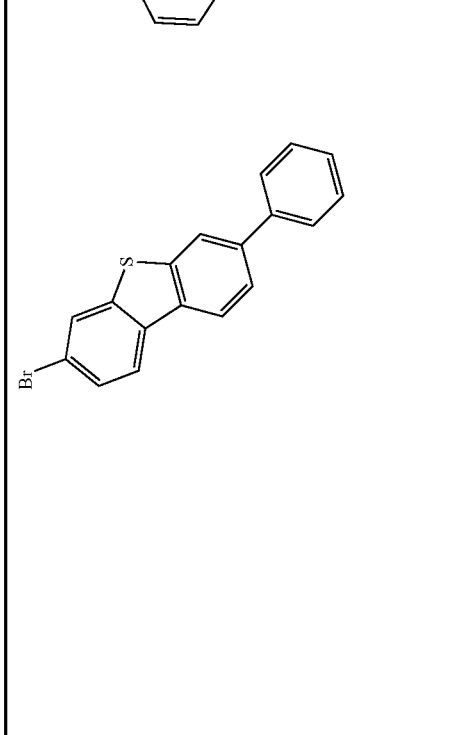 | 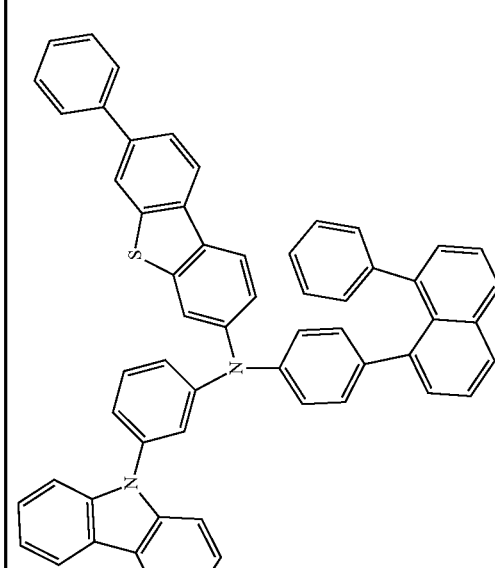 178 | 70 | 795.28 |

TABLE 4-continued
| IM 2A-X | Raw material 5 | Compound | Yield/% | MS (m/z)/ [M + H]+ |
|---|---|---|---|---|
| | | 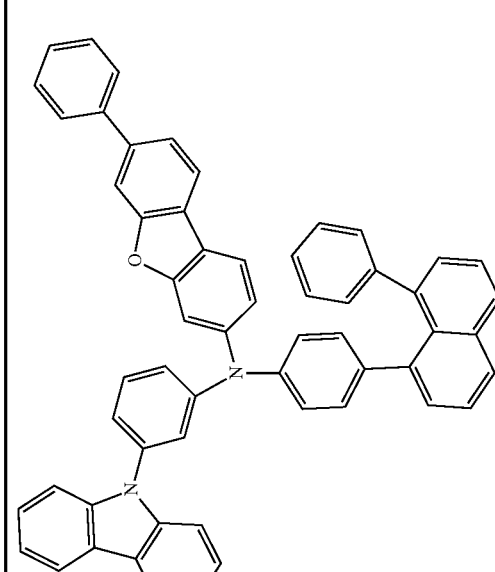 179 | 71 | 779.30 |

TABLE 4-continued
| IM 2A-X | Raw material 5 | Compound | Yield/% | MS (m/z) [M + H]+ |
|---|---|---|---|---|
| | 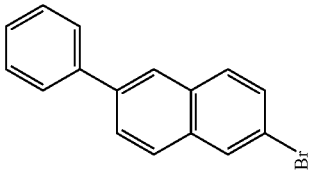 | 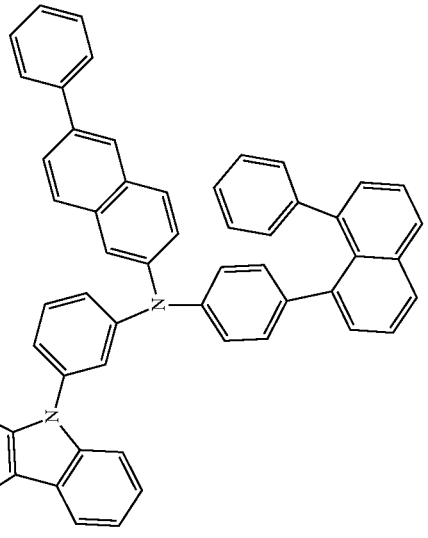 180 | 72 | 739.30 |
| | 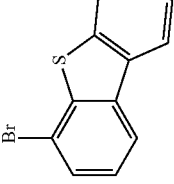 | 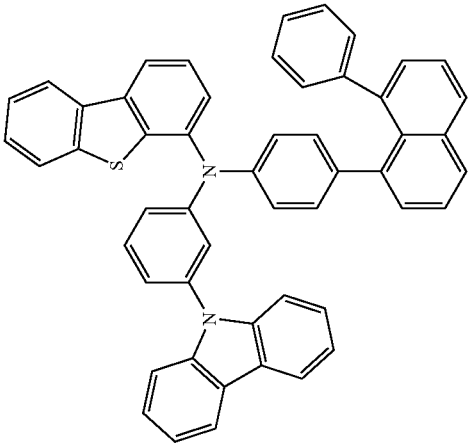 196 | 72 | 719.24 |

TABLE 4-continued

| IM 2A-X | Raw material 5 | Compound | Yield/% | MS (m/z) [M + H]⁺ |
|---|---|---|---|---|
| | | 202 | 73 | 729.32 |
| IM 2A-3 | | 3 | 73 | 795.28 |

TABLE 4-continued
| IM 2A-X | Raw material 5 | Compound | Yield/% | MS (m/z) [M + H]+ |
|---|---|---|---|---|
| | 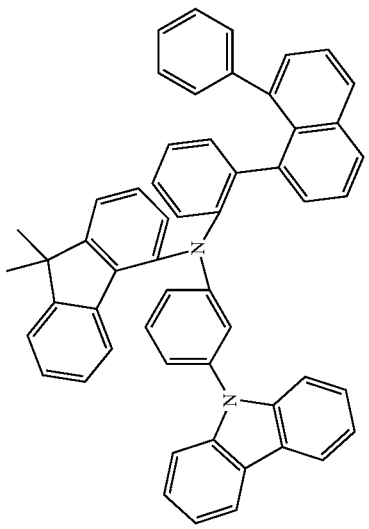 | 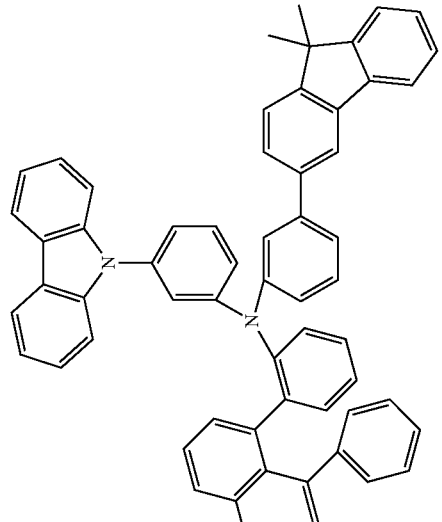 11 | 71 | 729.32 |
| | 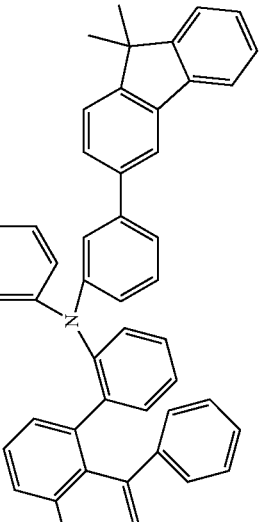 | 18 | 72 | 805.35 |

TABLE 4-continued

| IM 2A-X | Raw material 5 | Compound | Yield/% | MS (m/z) [M + H]+ |
|---|---|---|---|---|
| IM 2A-4 | | 8 | 74 | 854.35 |

TABLE 4-continued

| IM 2A-X | Raw material 5 | Compound | Yield/% | MS (m/z)/ [M + H]+ |
|---|---|---|---|---|
| IM 2A-5 | | 13 | 72 | 841.35 |

TABLE 4-continued

| IM 2A-X | Raw material 5 | Compound | Yield/% | MS (m/z)/ [M + H]+ |
|---|---|---|---|---|
| IM 2A-6 | | 17 | 75 | 789.32 |

TABLE 4-continued

| IM 2A-X | Raw material 5 | Compound | Yield/% | MS (m/z)/ [M + H]+ |
|---|---|---|---|---|
| IM 2A-7 | | 81 | 72 | 739.30 |

TABLE 4-continued
| IM 2A-X | Raw material 5 | Compound | Yield/% | MS (m/z) [M + H]+ |
|---|---|---|---|---|
| | 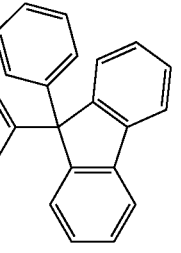 | 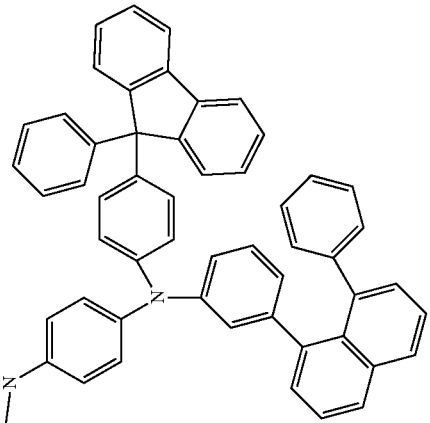 90 | 73 | 853.35 |

TABLE 4-continued

| IM 2A-X | Raw material 5 | Compound | Yield/% | MS (m/z) [M + H]+ |
|---|---|---|---|---|
| IM 2A-8 | | 117 | 72 | 855.37 |
| IM 2A-9 | | 134 | 70 | 943.36 |

TABLE 4-continued
| IM 2A-X | Raw material 5 | Compound | Yield/% | MS (m/z) [M + H]+ |
|---|---|---|---|---|
| IM 2A-10 | | 143 | 71 | 896.14 |
| IM 2A-11 | | 147 | 69 | 845.29 |
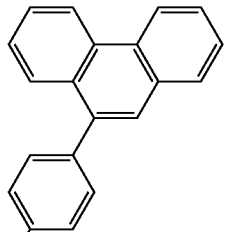

TABLE 4-continued
| IM 2A-X | Raw material 5 | Compound | Yield/% | MS (m/z) [M + H]⁺ |
|---|---|---|---|---|
| 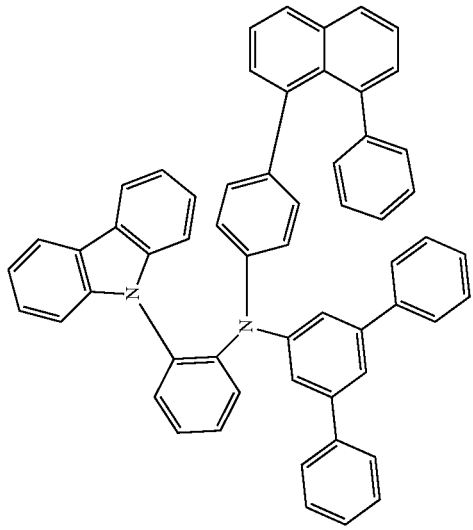<br>IM 2A-12 | 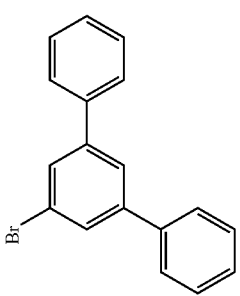 | 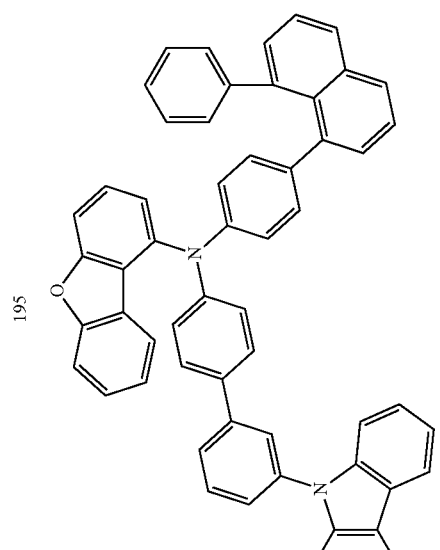<br>195 | 70 | 765.32 |
| 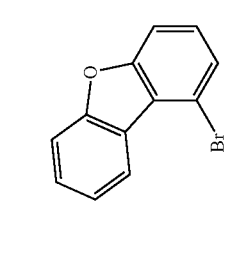<br>IM 2A-13 | 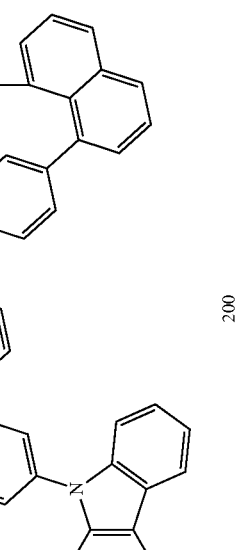 | <br>200 | 71 | 779.3 |

TABLE 4-continued

| IM 2A-X | Raw material 5 | Compound | Yield/% | MS (m/z) [M + H]+ |
|---|---|---|---|---|
| | (dibenzothiophene-Br) | 201 | 70 | 795.28 |
| | (9,9-dimethylfluorene-Br) | 203 | 72 | 805.35 |

TABLE 4-continued

| IM 2A-X | Raw material 5 | Compound | Yield/% | MS (m/z) [M + H]+ |
|---|---|---|---|---|
| IM 2A-14 | | 204 | 72 | 687.31 |
| IM 2A-15 | | 198 | 73 | 804.29 |

Nuclear Magnetic Resonance (NMR) Data of Some Compounds were Shown in Table 5 Below:

TABLE 5

| Compound | NMR data |
| --- | --- |
| Compound 1 | $^1$H-NMR(CD$_2$Cl$_2$, 400 MHZ): 7.99-7.92(m, 4H), 7.78(d, 2H), 7.65-7.59(m, 3H), 7.57-7.49(m, 6H), 7.46-7.23(m, 17H), 7.20-7.12(m, 3H), 7.01(t, 1H), 6.77(d, 2H), 6.67(d, 2H), 6.60(d, 2H). |
| Compound 22 | $^1$H-NMR(CD$_2$Cl$_2$, 400 MHZ): 7.94-7.92(m, 2H), 7.77(d, 2H), 7.63-7.50(m, 8H), 7.46-7.23(m, 18H), 7.20-7.12(m, 3H), 7.01(t, 1H), 6.77(d, 2H), 6.60(d, 2H), 6.51(d, 2H). |

Fabrication and Evaluation of OLEDs

Example 1

An OLED was fabricated through the following process: A substrate plated with an ITO/Ag/ITO (120 nm) electrode was cut into a size of 40 mm (length)×40 mm (width)×0.7 mm (thickness), then the substrate was processed through photolithography into an experimental substrate with cathode, anode, and insulating layer patterns, and the experimental substrate was subjected to a surface treatment with ultraviolet (UV)-ozone and O$_2$:N$_2$ plasma to increase a work function of the anode (experimental substrate) and remove scums.

A compound HAT-CN was vacuum-deposited on the experimental substrate (anode) to form an HIL with a thickness of 100 Å; and then NPB was vacuum-deposited on the HIL to form an HTL with a thickness of 1,100 Å.

The compound 1 was deposited on the HTL to form an EBL with a thickness of 100 Å.

The compounds α,β-ADN and BD-1 were deposited on the EBL in a weight ratio of 96%:4% to form an organic light-emitting layer (EML) with a thickness of 240 Å.

TPBi and LiQ were deposited on the EML in a weight ratio of 1:1 to form an ETL with a thickness of 350 Å.

Yb was deposited on the ETL to form an EIL with a thickness of 15 Å, and then argentum (Ag) and magnesium (Mg) were deposited on the EIL in a weight ratio of 8:2 to form a cathode with a thickness of 120 Å.

A compound CP-1 was deposited on the cathode to form an organic capping layer (CPL) with a thickness of 630 Å.

A device obtained after the deposition was encapsulated with a UV curing resin in a nitrogen glove box (with strictly-controlled water and oxygen contents).

Examples 2 to 34

OLEDs were each fabricated by the same method as in Example 1, except that the remaining compounds listed in Table 7 were each used instead of the compound 1 in the formation of the EBL.

Comparative Examples 1 to 4

OLEDs in Comparative Examples 1 to 4 were each fabricated by the same method as in Example 1, except that compounds A, B, C, and D were each used instead of the compound 1 as a material for the EBL.

The structures of the main materials used in the above examples and comparative examples were shown in Table 6.

TABLE 6

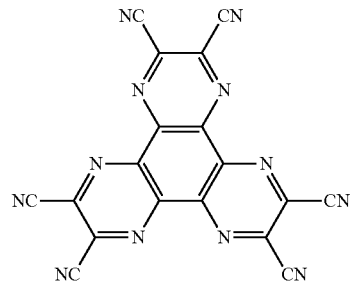 [SMILES: N#Cc1nc2c3nc(C#N)c(C#N)nc3c3nc(C#N)c(C#N)nc3c2nc1C#N]

HAT-CN

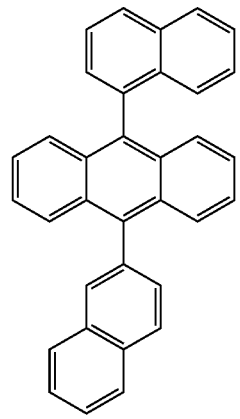 [SMILES: c1ccc2cc(-c3c4ccccc4c(-c4cccc5ccccc45)c4ccccc34)ccc2c1]

α,β-ADN

TABLE 6-continued
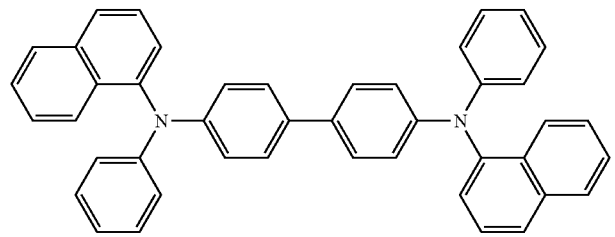 [SMILES: c1ccc(N(c2ccc(-c3ccc(N(c4ccccc4)c4cccc5ccccc45)cc3)cc2)c2cccc3ccccc23)cc1]
NPB
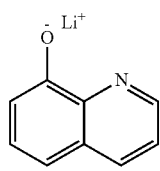 [SMILES: [Li+] ; Oc1cccc2cccnc12]
LiQ
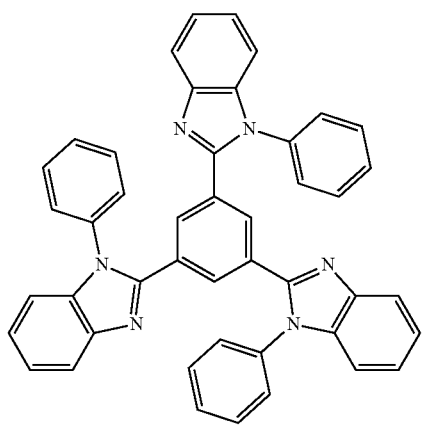 [SMILES: c1ccc(-n2c(-c3cc(-c4nc5ccccc5n4-c4ccccc4)cc(-c4nc5ccccc5n4-c4ccccc4)c3)nc3ccccc32)cc1]
TPBi
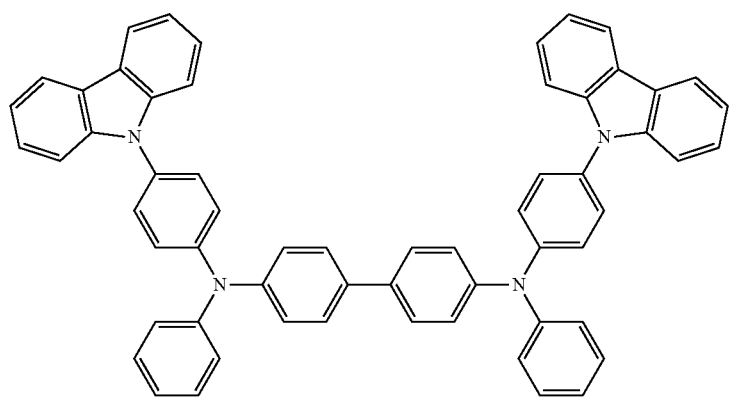 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
CP-1

TABLE 6-continued
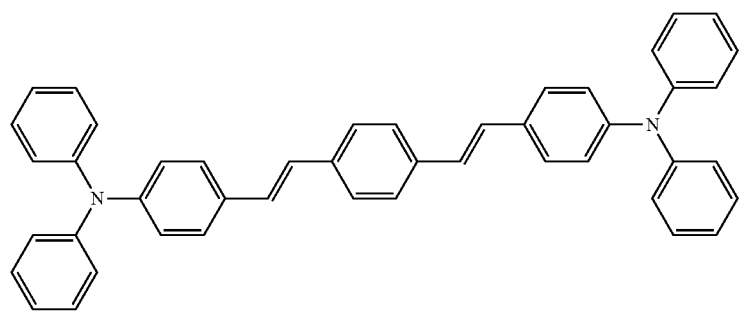 [SMILES: C(=C\c1ccc(N(c2ccccc2)c2ccccc2)cc1)/c1ccc(/C=C/c2ccc(N(c3ccccc3)c3ccccc3)cc2)cc1]
BD-1
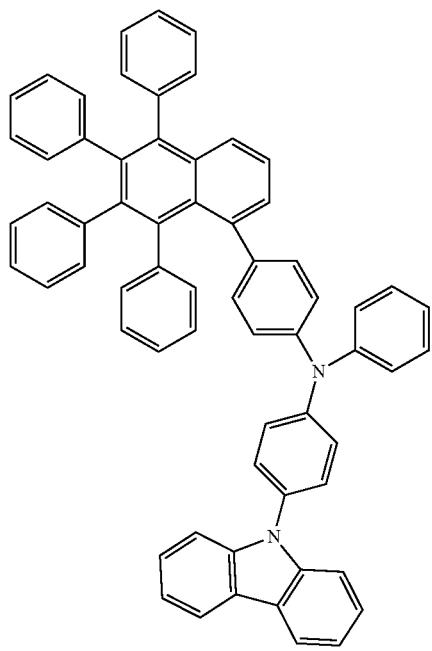 [SMILES: c1ccc(-c2c(-c3ccccc3)c(-c3ccccc3)c3c(-c4ccc(N(c5ccccc5)c5ccc(-n6c7ccccc7c7ccccc76)cc5)cc4)cccc3c2-c2ccccc2)cc1]
Compound A
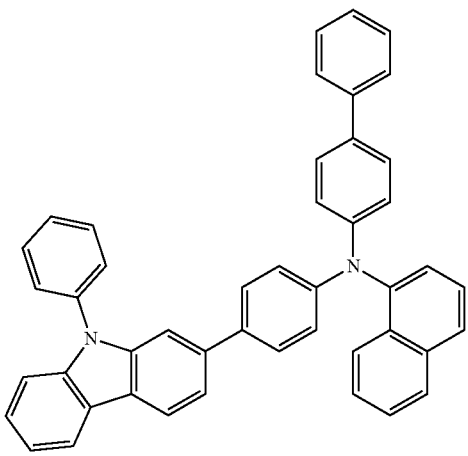 [SMILES: c1ccc(-c2ccc(N(c3ccc(-c4ccc5c6ccccc6n(-c6ccccc6)c5c4)cc3)c3cccc4ccccc34)cc2)cc1]
Compound B TABLE 6-continued

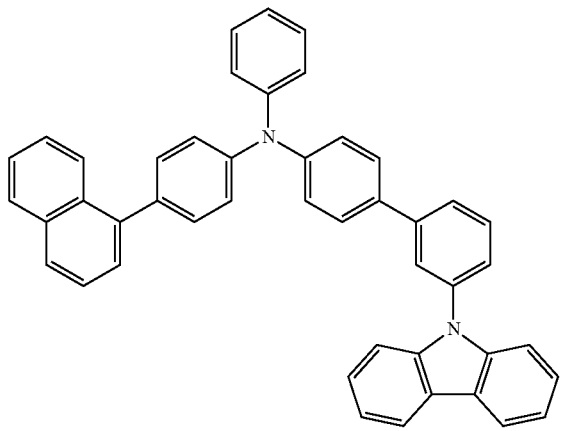 [SMILES: c1ccc(N(c2ccc(-c3cccc(-n4c5ccccc5c5ccccc54)c3)cc2)c2ccc(-c3cccc4ccccc34)cc2)cc1]

Compound C

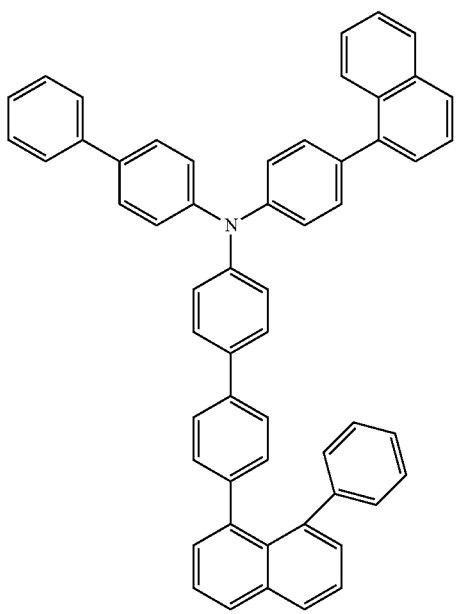 [SMILES: c1ccc(-c2ccc(N(c3ccc(-c4ccc(-c5cccc6cccc(-c7ccccc7)c56)cc4)cc3)c3ccc(-c4cccc5ccccc45)cc3)cc2)cc1]

Compound D

The performance of each of the OLEDs fabricated in the examples and comparative examples was shown in Table 7, wherein the driving voltage, efficiency, and chromaticity coordinates were tested at a constant current density of 10 mA/cm$^2$, and the T95 life span was tested at a constant current density of 20 mA/cm$^2$.

TABLE 7

| Example No. | EBL | Working voltage Volt (V) | Light-emitting efficiency (Cd/A) | EQE, % | Chromaticity coordinate CIEy | T95 (h) @20 mA/cm$^2$ |
|---|---|---|---|---|---|---|
| Example 1 | Compound 1 | 3.77 | 6.6 | 13.7 | 0.052 | 171 |
| Example 2 | Compound 2 | 3.82 | 6.4 | 13.3 | 0.052 | 175 |
| Example 3 | Compound 3 | 3.76 | 6.7 | 13.7 | 0.052 | 172 |
| Example 4 | Compound 8 | 3.75 | 6.5 | 13.4 | 0.052 | 175 |
| Example 5 | Compound 11 | 3.77 | 6.5 | 13.3 | 0.052 | 167 |
| Example 6 | Compound 13 | 3.82 | 6.7 | 13.7 | 0.052 | 166 |
| Example 7 | Compound 17 | 3.79 | 6.7 | 13.8 | 0.052 | 165 |
| Example 8 | Compound 18 | 3.80 | 6.4 | 13.5 | 0.052 | 172 |
| Example 9 | Compound 22 | 3.76 | 6.3 | 13.4 | 0.052 | 167 |
| Example 10 | Compound 46 | 3.76 | 6.4 | 13.2 | 0.052 | 170 |
| Example 11 | Compound 76 | 3.82 | 6.4 | 13.3 | 0.052 | 170 |
| Example 12 | Compound 81 | 3.79 | 6.3 | 13.4 | 0.052 | 174 |

TABLE 7-continued

| Example No. | EBL | Working voltage Volt (V) | Light-emitting efficiency (Cd/A) | EQE, % | Chromaticity coordinate CIEy | T95 (h) @20 mA/cm² |
|---|---|---|---|---|---|---|
| Example 13 | Compound 90 | 3.76 | 6.7 | 13.8 | 0.052 | 170 |
| Example 14 | Compound 117 | 3.80 | 6.4 | 13.4 | 0.052 | 173 |
| Example 15 | Compound 134 | 3.76 | 6.5 | 13.4 | 0.052 | 166 |
| Example 16 | Compound 143 | 3.82 | 6.4 | 13.5 | 0.052 | 169 |
| Example 17 | Compound 147 | 3.75 | 6.5 | 13.3 | 0.052 | 169 |
| Example 18 | Compound 173 | 3.82 | 6.8 | 13.9 | 0.052 | 175 |
| Example 19 | Compound 174 | 3.76 | 6.6 | 13.6 | 0.052 | 173 |
| Example 20 | Compound 175 | 3.82 | 6.6 | 13.6 | 0.052 | 174 |
| Example 21 | Compound 176 | 3.75 | 6.5 | 13.5 | 0.052 | 169 |
| Example 22 | Compound 177 | 3.78 | 6.6 | 13.6 | 0.052 | 174 |
| Example 23 | Compound 178 | 3.82 | 6.6 | 13.5 | 0.052 | 167 |
| Example 24 | Compound 179 | 3.81 | 6.7 | 13.8 | 0.052 | 167 |
| Example 25 | Compound 180 | 3.78 | 6.4 | 13.5 | 0.052 | 166 |
| Example 26 | Compound 195 | 3.77 | 6.5 | 13.5 | 0.052 | 168 |
| Example 27 | Compound 196 | 3.81 | 6.3 | 13.1 | 0.052 | 169 |
| Example 28 | Compound 198 | 3.79 | 6.5 | 13.3 | 0.052 | 172 |
| Example 30 | Compound 199 | 3.83 | 6.3 | 13.2 | 0.052 | 171 |
| Example 31 | Compound 200 | 3.82 | 6.4 | 13.2 | 0.052 | 166 |
| Example 32 | Compound 201 | 3.80 | 6.6 | 13.5 | 0.052 | 173 |
| Example 33 | Compound 202 | 3.82 | 6.5 | 13.5 | 0.052 | 168 |
| Example 34 | Compound 203 | 3.79 | 6.4 | 13.3 | 0.052 | 170 |
| Example 35 | Compound 204 | 3.78 | 6.7 | 13.7 | 0.052 | 170 |
| Comparative Example 1 | Compound A | 3.89 | 5.9 | 12.2 | 0.052 | 145 |
| Comparative Example 2 | Compound B | 3.86 | 6.1 | 12.6 | 0.052 | 140 |
| Comparative Example 3 | Compound C | 3.84 | 6.0 | 12.4 | 0.052 | 144 |
| Comparative Example 4 | Compound D | 3.94 | 5.5 | 11.4 | 0.052 | 143 |

It can be seen from the results in Table 7 that, compared with the OLEDs corresponding to well-known compounds fabricated in Comparative Examples 1 to 4, the OLEDs with the organic compound of the present application as an EBL fabricated in Examples 1 to 34 have a life span increased by at least 13.8%. It can be seen from the above data that, when the organic compound of the present application is used as an EBL of an electronic device, the light-emitting efficiency (Cd/A), EQE, and life span (T95) of the electronic device are all improved to some extent.

Those of ordinary skill in the art can understand that the above implementations are specific embodiments for implementing the present application; and in practical applications, various changes may be made in terms of forms and details without departing from the spirit and scope of the present application.

What is claimed is:
1. An organic compound is selected from the group consisting of the following compounds.

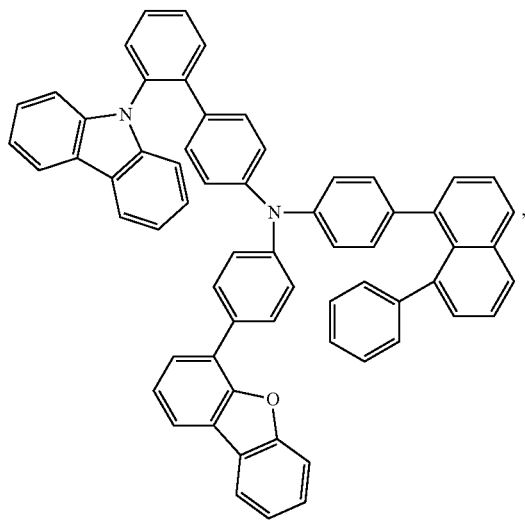

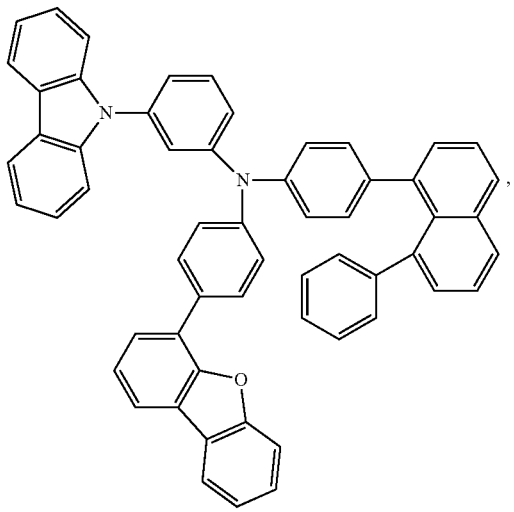
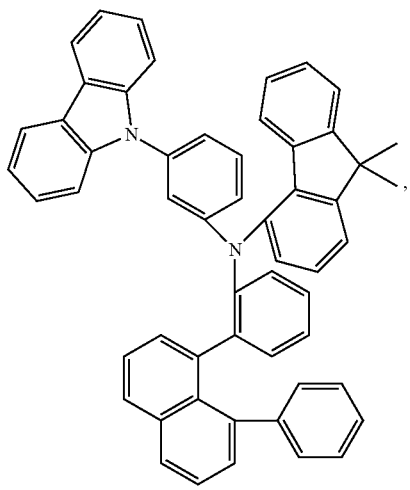
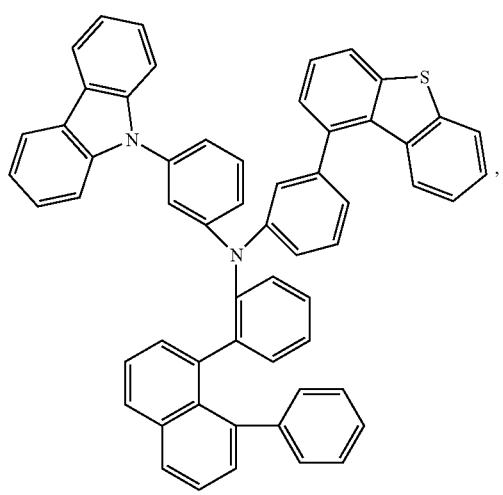
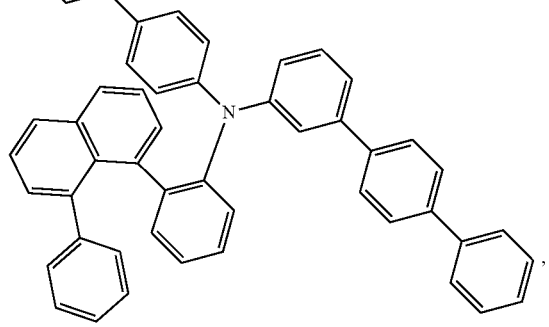
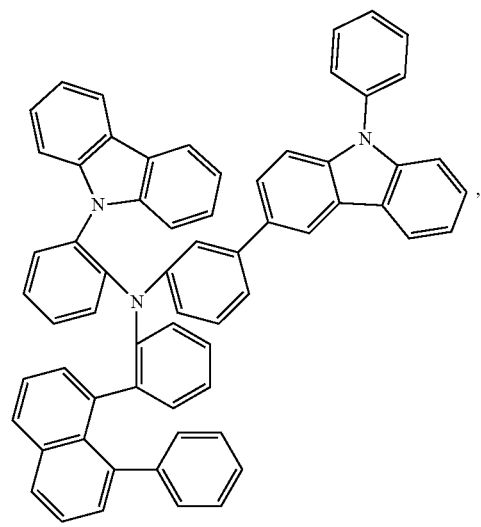
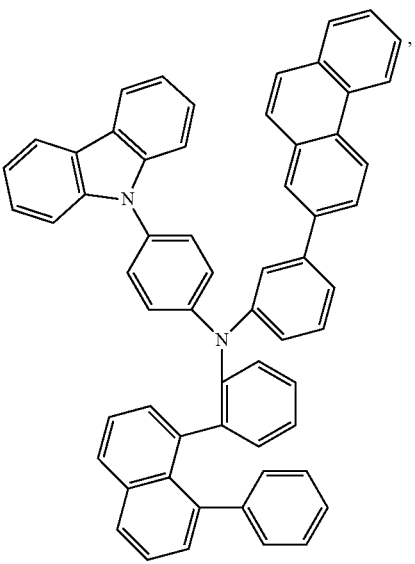

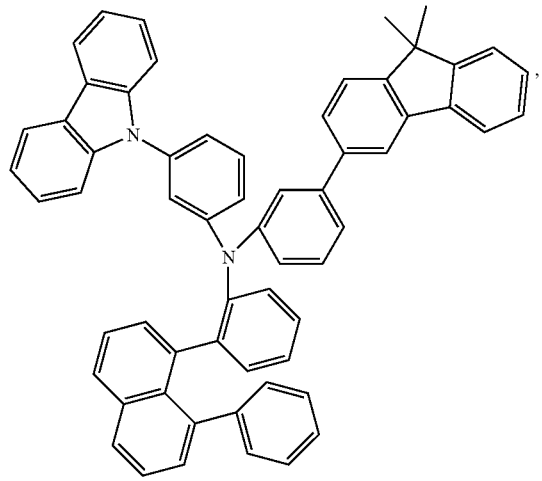
18
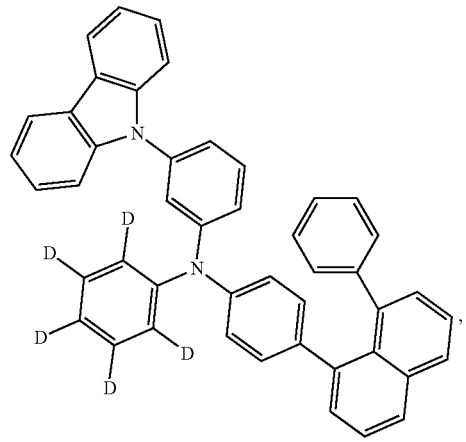
76
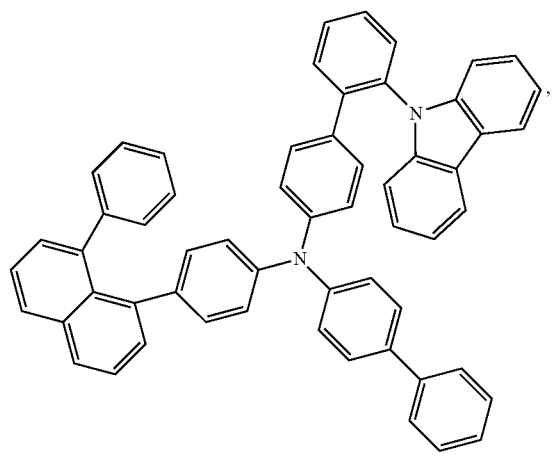
22
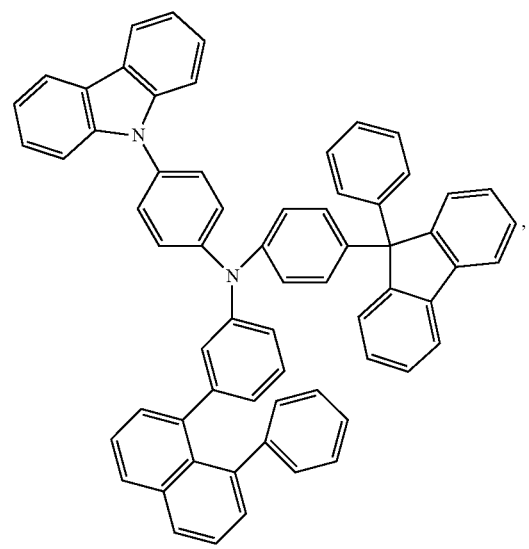
90
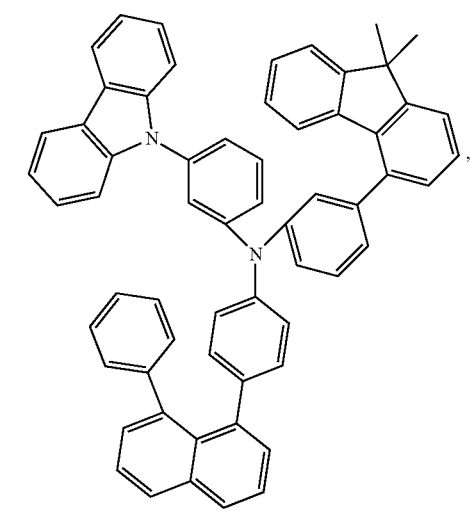
46
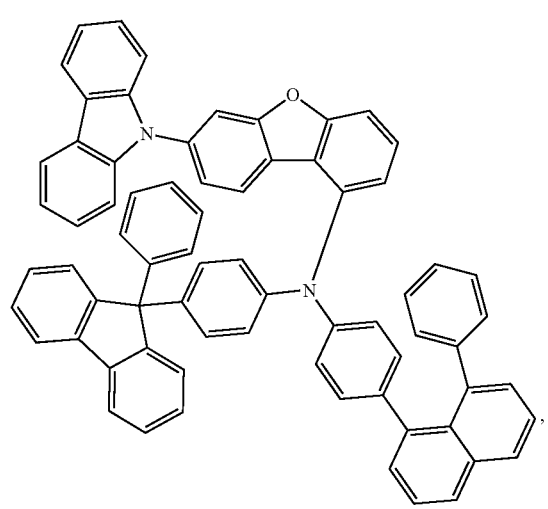
134

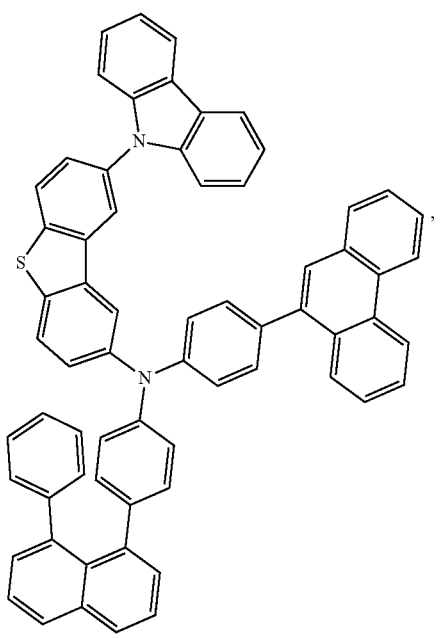
143
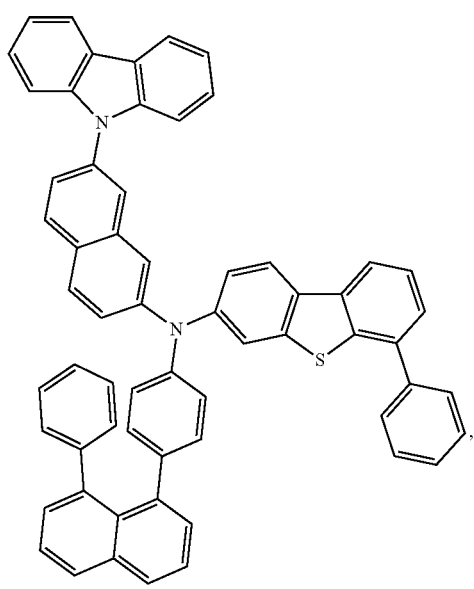
147
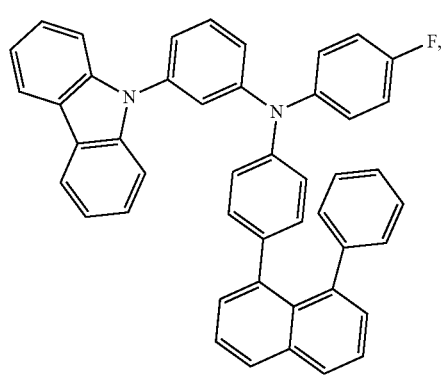
173
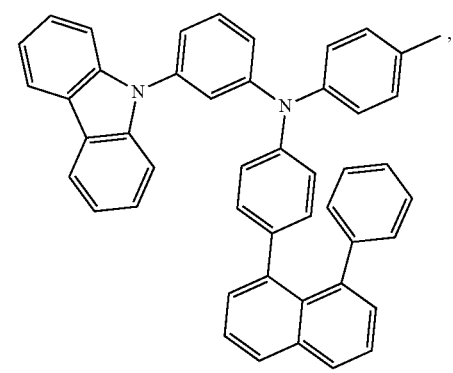
174
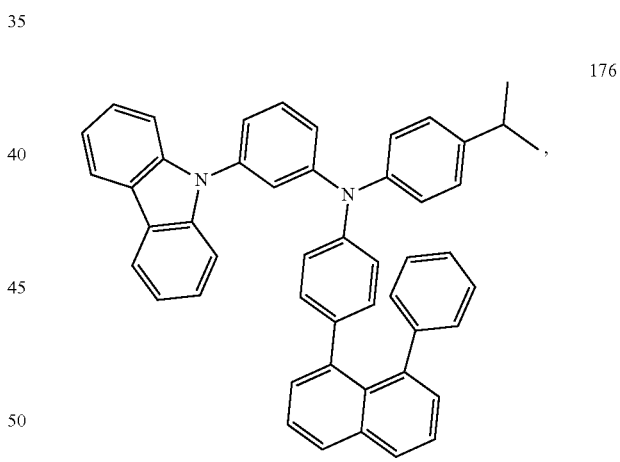
175
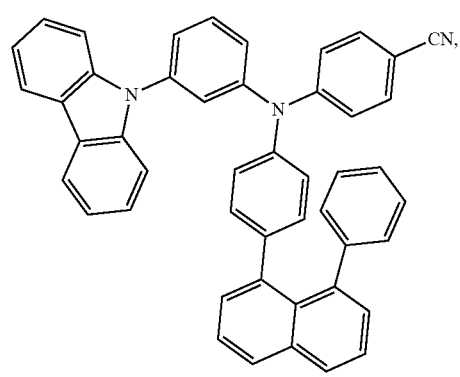
176
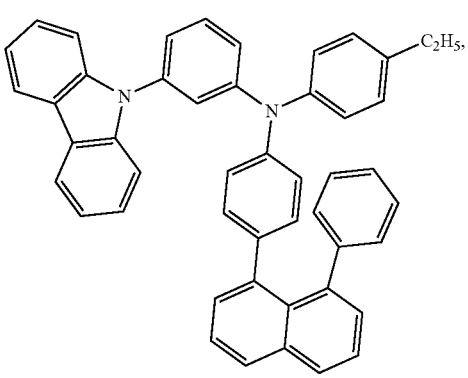
177

185
-continued
178
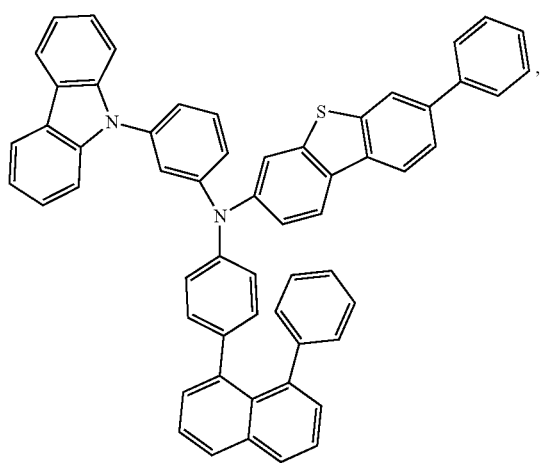
180
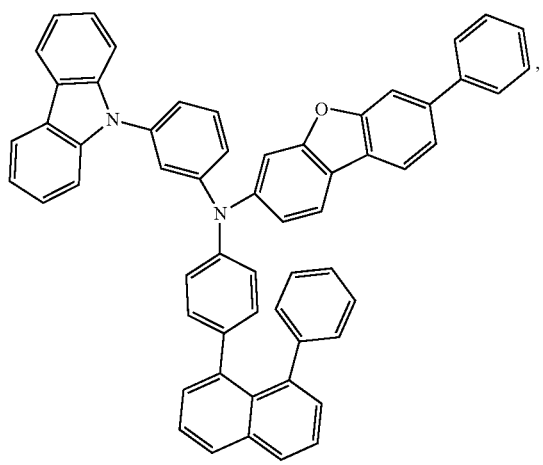
195
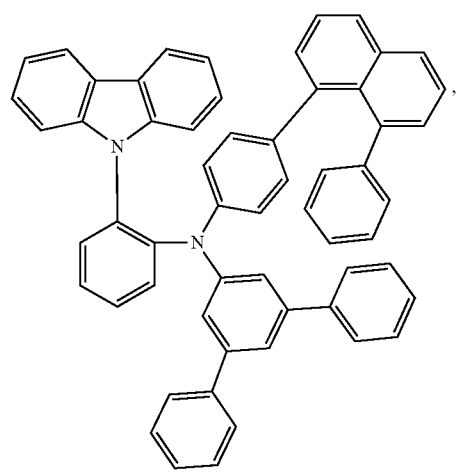
186
-continued
196
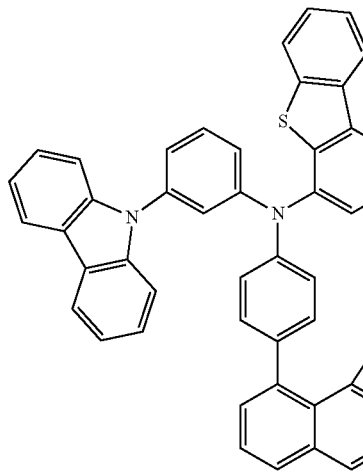
198
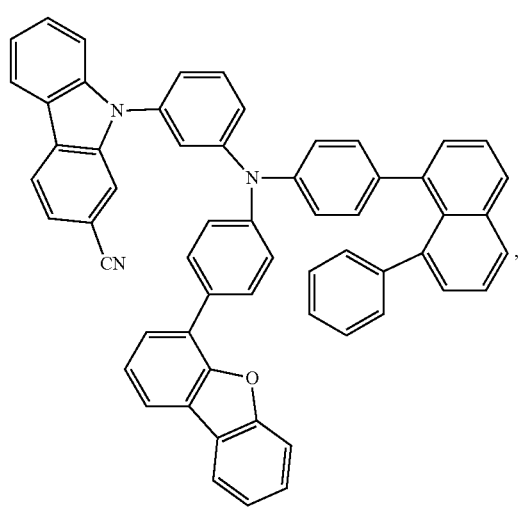
199
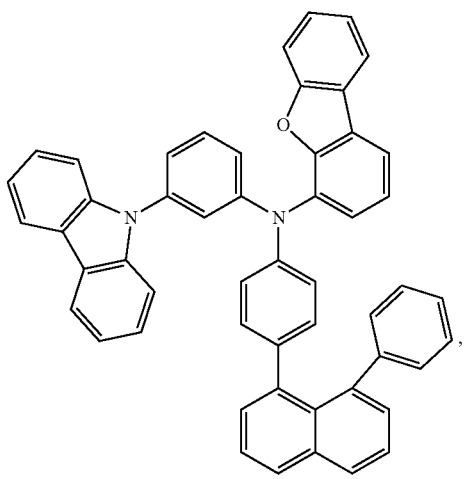

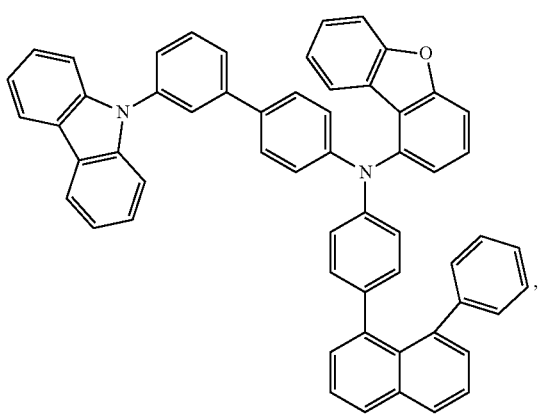

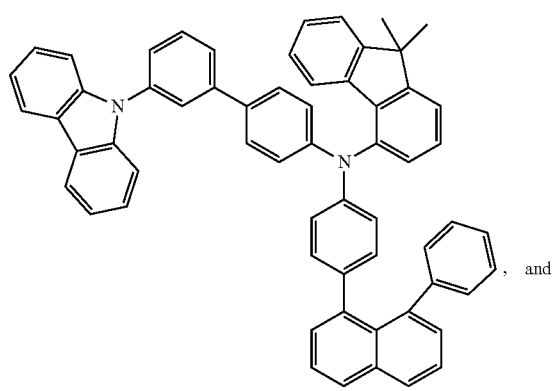

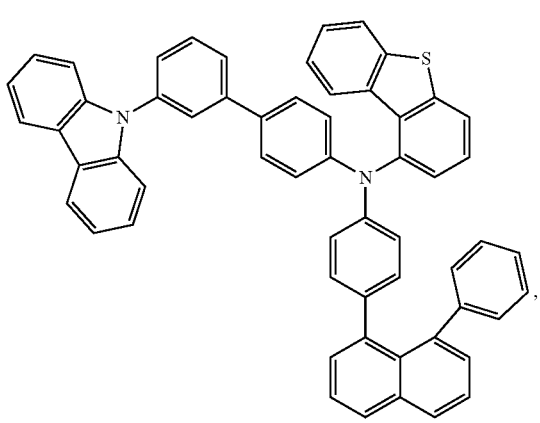

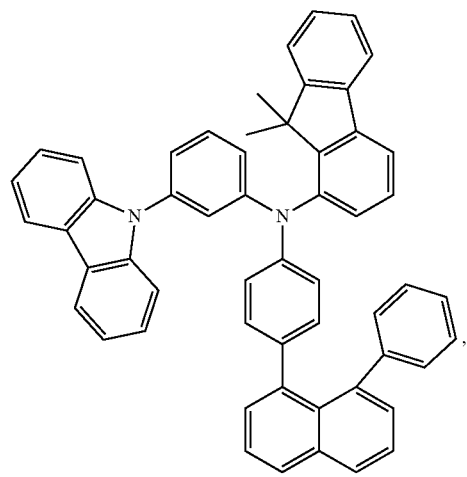

2. An electronic device, comprising: an anode and a cathode that are arranged oppositely, and a functional layer arranged between the anode and the cathode, wherein the functional layer comprises the organic compound according to claim 1.

3. The electronic device according to claim 2, wherein the functional layer comprises a hole transport layer (HTL) or an electron blocking layer (EBL), and the HTL or the EBL comprises the organic compound.

* * * * *